United States Patent
Bartsevich et al.

(10) Patent No.: US 11,680,254 B2
(45) Date of Patent: Jun. 20, 2023

(54) ENGINEERED MEGANUCLEASES SPECIFIC FOR RECOGNITION SEQUENCES IN THE PCSK9 GENE

(71) Applicant: Precision BioSciences, Inc., Durham, NC (US)

(72) Inventors: Victor Bartsevich, Durham, NC (US); Derek Jantz, Durham, NC (US); James Jefferson Smith, Morrisville, NC (US); Janel Lape, Wake Forest, NC (US)

(73) Assignee: PRECISION BIOSCIENCES, INC., Durham, NC (US)

(*) Notice: Subject to any disclaimer, the term of this patent is extended or adjusted under 35 U.S.C. 154(b) by 912 days.

(21) Appl. No.: 16/606,856

(22) PCT Filed: Apr. 20, 2018

(86) PCT No.: PCT/US2018/028607
§ 371 (c)(1),
(2) Date: Oct. 21, 2019

(87) PCT Pub. No.: WO2018/195449
PCT Pub. Date: Oct. 25, 2018

(65) Prior Publication Data
US 2020/0131489 A1    Apr. 30, 2020

Related U.S. Application Data

(60) Provisional application No. 62/516,966, filed on Jun. 8, 2017, provisional application No. 62/488,403, filed on Apr. 21, 2017.

(51) Int. Cl.
*C12N 9/22* (2006.01)
*C12N 15/86* (2006.01)
*A61K 48/00* (2006.01)

(52) U.S. Cl.
CPC .............. *C12N 9/22* (2013.01); *C12N 15/86* (2013.01); *A61K 48/00* (2013.01); *C12N 2750/14143* (2013.01); *C12N 2800/80* (2013.01)

(58) Field of Classification Search
CPC .................. C12N 9/22; C12N 2800/80; C12Y 304/21061
See application file for complete search history.

(56) References Cited

U.S. PATENT DOCUMENTS

2011/0263028 A1* 10/2011 Cabaniols .............. C12N 15/85
435/465
2016/0153005 A1*  6/2016 Zhang ................ A61K 48/0058
435/457

FOREIGN PATENT DOCUMENTS

| CA | 2 603 615 A1 | 3/2009 | |
|---|---|---|---|
| JP | 2006-516403 A | 7/2006 | |
| JP | 2009-511085 A | 3/2009 | |
| JP | 2011-501971 A | 1/2011 | |
| JP | 2011-527906 A | 11/2011 | |
| JP | 2016-524472 A | 8/2016 | |
| WO | WO 2004/067736 A2 | 8/2004 | |
| WO | WO 2004/067753 A2 | 8/2004 | |
| WO | WO 2007/047859 A2 | 4/2007 | |
| WO | WO 2009/059195 A2 | 5/2009 | |
| WO | WO 2010/009147 A1 | 1/2010 | |
| WO | WO 2014/204726 A1 | 12/2014 | |
| WO | WO 2015/175642 A2 | 11/2015 | |
| WO | WO-2015175642 A2 * | 11/2015 | ............. A61K 39/00 |
| WO | WO 2017/044649 A1 | 3/2017 | |

OTHER PUBLICATIONS

Gen Bank Accession No. NM_174936.3, publicly available May 10, 2014, printed as pp. 1/5-5/5. (Year: 2014).*
Taylor et al. Lahedes: the LAGLIDADG homing endonuclease database and engineering server. Nucleic Acids Research, vol. 40, W110-W116, May 8, 2012. (Year: 2012).*
International Search Report and Written Opinion for Application No. PCT/US2018/028607 dated Jun. 28, 2018.
International Preliminary Report on Patentability for Application No. PCT/US2018/028607 dated Oct. 31, 2019.
Ruiz de Galarreta et al., Therapeutic editing of hepatocyte genome in vivo. J Hepatol. Oct. 2017; 67(4):818-828. doi: 10.1016/j.jhep.2017.05.012. Epub May 17, 2017.
Wang et al., CRISPR-Cas9 Targeting of PCSK9 in Human Hepatocytes In Vivo—Brief Report. Arterioscler Thromb Vasc Biol. May 2016; 36(5):783-6. doi: 10.1161/ATVBAHA.116.307227. Epub Mar. 3, 2016.

* cited by examiner

*Primary Examiner* — Jennifer Dunston
(74) *Attorney, Agent, or Firm* — Womble Bond Dickinson (US) LLP

(57) ABSTRACT

The present invention encompasses engineered meganucleases which recognize and cleave a recognition sequence within the human PCSK9 gene. The present invention also encompasses methods for using such engineered meganucleases in a pharmaceutical composition and in methods for treating or reducing the symptoms of cholesterol-related disorders, such as hypercholesterolemia. Further, the invention encompasses pharmaceutical compositions comprising engineered meganuclease proteins, nucleic acids encoding engineered meganucleases, and the use of such compositions for treating cholesterol-related disorders, such as hypercholesterolemia.

8 Claims, 22 Drawing Sheets
Specification includes a Sequence Listing.

```
                    PCS7            PCS8
                    Half-Site       Half-Site
PCS 7-8             TGGACCTCTTTGCCCCAGGGGA    SEQ ID NO:4
Recognition Sequence ACCTGGAGAAACGGGGTCCCCT    SEQ ID NO:5
```

|  | Wild-Type or Indel Sequence | SEQ ID NO: | Indel Frequency | |
|---|---|---|---|---|
|  |  |  | RA1857 | RA1866 |
| Wild-type | TGGACCTCTTT-GCCCCAGGGGA | 4 | - | - |
|  |  |  |  |  |
| Top 8 most frequent indel sequences | TGGACCTCTTT-G---CAGGGGA | 33 | 3.41 | 1.88 |
| | TGGACC-CTTT-GCCCCAGGGGA | 34 | 1.83 | 1.45 |
| | TGGACCTCTTT-GC-CCAGGGGA | 35 | 1.73 | 1.03 |
| | TGGACCTCTTTTGCCCCAGGGGA | 36 | 1.46 | 0.84 |
| | TGGACCTCTTT-GC--CAGGGGA | 37 | 1.1 | 0.71 |
| | TGGACCTCTT----CCCAGGGGA | 38 | 0.98 | 0.64 |
| | TGGACCTCTTT----CCAGGGGA | 39 | 0.49 | 0.32 |
| | TGGACCTCTT-----CCAGGGGA | 40 | 0.4 | 0.29 |

M11657 (control)

B.

C.

D.

E.

C.

A.

B.

SEQUENCE LISTING

```
<160> NUMBER OF SEQ ID NOS: 40

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro
```

```
<210> SEQ ID NO 2
<211> LENGTH: 9
<212> TYPE: PRT
<213> ORGANISM: Chlamydomonas reinhardtii

<400> SEQUENCE: 2

Leu Ala Gly Leu Ile Asp Ala Asp Gly
1               5

<210> SEQ ID NO 3
<211> LENGTH: 25378
<212> TYPE: DNA
<213> ORGANISM: Homo sapiens

<400> SEQUENCE: 3
gtccgatggg gctctggtgg cgtgatctgc gcgccccagg cgtcaagcac ccacacccta      60
gaaggtttcc gcagcgacgt cgaggcgctc atggttgcag cgggcgccg  ccgttcagtt     120 cagggtctga gcctggagga gtgagccagg cagtgagact ggctcgggcg ggccgggacg     180
cgtcgttgca gcagcggctc ccagctccca gccaggattc cgcgcgcccc ttcacgcgcc     240
ctgctcctga acttcagctc ctgcacagtc ctccccaccg caaggctcaa ggcgccgccg     300
gcgtggaccg cgcacggcct ctaggtctcc tcgccaggac agcaacctct cccctggccc     360
tcatgggcac cgtcagctcc aggcggtcct ggtggccgct gccactgctg ctgctgctgc     420
tgctgctcct gggtcccgcg gcgcccgtg  cgcaggagga cgaggacggc gactacgagg     480
agctggtgct agccttgcgt tccgaggagg acggcctggc cgaagcaccc gagcacggaa     540
ccacagccac cttccaccgc tgcgccaagg tgcgggtgta gggatgggag gccggggcga     600
acccgcagcc gggacggtgc ggtgctgttt cctctcgggc tcagtttcc  ccccatgtaa     660 gagaggaagt ggagtgcagg tcgccgaggg ctcttcgctt ggcacgatct  tggggactgc     720
aggcaaggcg gcggggagg  acgggtagtg gggagcacgg tggagagcgg ggacggccgg     780
ctctttgggg acttgctggg gcgtgcggct gcgctattca gtgggaaggt tcgcggggtt     840
gggagacccg gaggccgagg aagggcgagc agagcactgc caggatatcc tgcccagatt     900
tcccagtttc tgcctcgccg cggcacaggt gggtgaagga gtgaatgcct ggaacgtact     960
gggaactgca ccaggcacag agaaagcggg cttgccatta tagtgggttc cgatttggtt    1020
tggaaaacat gggcagcgga gggtggaggg cctggagaga aggccctacc cgagacaggg    1080
gcggggtggg aaggacggca gatgctggga gcacgaggca atttctttat gacacagaac    1140
tcatgctcta gtattccatc tgtttcagcc gaagaaaaga accagctgaa ggggcagggg    1200 agaagggcgcg gaggtattct cgaggcccat tggcgtccctt taggactcag gcagggaagg    1260
gcccttggtg ctctggagcc ggaggtggtg cgcctggtac tgggaccccg gagctgagcc    1320
cggcgcctca gcccacctgg ctgtctgccg accgtgtgcg gggcgagttt gctcaacaac    1380
tctgccagct tctggccctc aggctgtggg aagcttcttc ccggggcgag accactagct    1440 tttctaagt  attaccagcc caggacttgg ctgaggttct gtgtccccca gcttggagtc    1500
agatgtgggt ttgaatcttg gcttcctctc actagctgtg gtgcttgaca agtcacttat    1560
ccttgagcct ccattgccta atctttaaaa gggaggtgac aatcgtccct acggctcagt    1620
ggcagcagat ggggagatga agggaaagtt ctgttgacca tgagtgaact tacaatgcaa    1680 gccccgggg  gatcacttgc agttttgtcc ctgtctgcag tgtgacctgt tggtgacatt    1740
gtctttgctc caaaccacag ctcctggggc agaggggaaa attctgccac tcacagctgc    1800
```

```
ctgcccacgc ttctgtctga gtgtgctggg tggcaggatg gcaagtcctt actcagctca   1860
gtatagccct cttccttgtt ccctgagcct ttgactttct cgagggatgt tgtggggttg   1920
tggccaggat aagaaagggc atttcaagtt accactgctc caaaacaact gttctggaaa   1980
tagtgagtac cccatcctga gaggtgagta agcagaggct gtatgaccac ctgaaccaag   2040
cccttgagga tgtttcttct ctggtggaag tttggaacag gagcctcctc aagttcattt   2100
attcattcat tcaatggtta ttttgtggga atcgaattta gaatgaaaat atttttggc   2160 aagcagaaaa taattttag accaatcctt ttcttttagt catgagaaac tgaggcccag   2220
agagaggagg tcaccccagg tgcattagaa ctgggtttcc agaactgaca ctccactgca   2280
cagagtactc tcccaattca ttcaatttt atttagcgga aggcattttc agatgggtct   2340
ttgaagcatt agtaggagtt cagcgatgat ggtgtcatga gaattttatt ctaggattag   2400
gaggtaccat gaacaaagat acagagctgg gaaaaccaga ggtggaagat aaggagcaca   2460
tgtccacagt tctttttctt ttttttttga gatggagttt cgctcttgtt gcccaggctg   2520
gagtgcaatg gtgcagtctc agctcactgc aacatctgtc tcccgggttc aagtggttct   2580
cctgcctcag cctcccaaga gctgggatt acaggtacct gccaccacgc ccggctaatt   2640
tttgtatttt tagtagagaa ggggtttcac cacgttggcc aggctagtcg caaactcctg   2700
acctcctcag tggatccgag gaggtgatcc tcccgcctca gcctcccaaa gtgctcgaat   2760
tacaggtgtg agccaccacg cctggcctcc acagttcttt atccaccgtc tgaaatgtaa   2820
aatgttacga aaaccaaaag tttttttgt gatttatttg atggtagcac ctgacgtgaa   2880
ctgacatgag attatttta atttagttgt gtgaatatgc atattcatat attttgctgc   2940
atagattaca gtatgcagct ccagattctt ccaagcagac tctgattgcc cattactgcc   3000
tttctaaaat ccaaacaagt tctgaggttc aaaaccgttt tggccctaag gctttgggta   3060 aaggggggtgg actctgttct actctgactg gagtccaaga tgcatatata cagagatatg   3120
ggtgatgggg ctgcaaggta ggttgaggta ggggccaagg aggagcatgg agtttggact   3180
tgattcatga ggctgtgggg agccagtgaa ggttcttaag caggtatgtc tgcctgagag   3240
cagttggagc agacaagagc taaaaaccaa acaaatcacc atagatagtg gctgctataa   3300
tttgtttgtc ccctccaaat ctcatgtgga aatttggtcc tcagtgttgg aagtggggcc   3360
taatgggagg tgtttgggtc atggggagg aaccctgtg aaaggcttgg tgccgtcctt   3420
gtgataatga gtaagttctc ccgctatgat ttcccttgaa ggctgattat taaaagagc   3480 ttggcaccctc cctctcttct ctcttgcttc ttctcttgcc atgtgattga tctctgcaca   3540
tgtaggctcc ccttcacctt ctgccatcag tgaaagcagc ttaaggccct caccagaagc   3600
agatgctggt gccatgcttc ctggagagct tgcagaatca tgagctgaat aaatcccttt   3660
tccttgtaaa ttactcacct tcaggtattc ctttatatag caacacaaaa ggactaagac   3720
agtggccttg acttttctct ctctttaaga agtgttgcct ttgctcactt agtcatccct   3780
tctgcctgca tttgtagagc atctggatgg gagatttata taaccgtcac tcttgacttt   3840
cccagcaggc ctatgtcata ggtactgtgg tctctacaat acagcagagg tatctgaggc   3900
tccgagaggt tgagtgactt gctcatggct gcacaaccag taaatattgg agctggaatt   3960
caggtccacg gtttcctggc tccaaagccc atgattttt ccctcaattt attctgactg   4020
gggcatgggg gagggggtgg cctttgggca gggccaccag gagcgaccag gcccgtagag   4080
agctgggtgc aggtacagag gaaaacctgt tgtcgagtgt ggcccgtagt tcccattttt   4140
```

-continued

```
gcctgaatgg cacatttgaa agtgttatat aaccatgtga ataataatag ttggcctata    4200
tgagttcttt aatttgcttt ttggtccgca tttggtaact tctttatcat ctactatact    4260
ctgttgtgtc tcttttgttg taatttgtaa gtaggggtga gataaagtac acctagggtt    4320
tgctgggttt cttccatgtc atcatgttcc tccttgcatg gggccaggat ccgtggaggt    4380
tgcctggcac ctacgtggtg gtgctgaagg aggagaccca cctctcgcag tcagagcgca    4440
ctgcccgccg cctgcaggcc caggctgccc gccggggata cctcaccaag atcctgcatg    4500
tcttccatgg ccttcttcct ggcttcctgg tgaagatgag tggcgacctg ctggagctgg    4560
tgagccaccc ttttggggaa tggcacttcc tgatagggct gggccactgc atatacactg    4620
gggactgtgc ttagtaggcc cattgctgaa aatcagaagg ggacagcaag tatgtattga    4680
gcacttatcg ggtaccaagc acagtaacta ctggctttct gtatagaatt ccctttaagc    4740
ctggccatgc cccagtggta cgtctatctt catttgaaag acgaggagac tgaagttcag    4800
aggggaccac acagacagct aggggtgagg cctggatcaa acccattggt ctgcctgcca    4860
gccattcttg tgccaatgca tctgctgcct acggaaacct gtaggacaa ggccctggga    4920
tgttcagtgg agcctgagtc atttttataaa aaagcatgac tctagggtcc aaaattcctt    4980
tgaagctgtt gctatccaga gtgaagtccc ttctttagga caggtggcc ctcctccctc    5040
ctggatgtca catcttcggt ggaggggcag aaagggact gggtattctc ctcaccctgg    5100
ccctagtgct tcaaatctta aaaaacgtt tttatttgtg cttctgcacc accttctagc    5160
ccacctcgtt tcctggcctc taacttgatg agagcgtgtg tcattttcac actgattctc    5220
cacatggcag gcggtgcttc ttagcctcct gcagacagtg aggccccacg gtcttgtcca    5280
aggtcacaca gcgtgtaatg ggcagggtca gagtctggag tctggacctg ggtctcctag    5340
ctgcactgca ctgctgcccc atgggttaat cagctcagca taccgtggct gaacagctac    5400
ctcataccaa ggcctgtggc gccatgacag ggattgacag ggtccctgcc ttggaaaccc    5460
gtagtctaag tagaggagac tgacaagtca atgccttcca tcagtctgct caacacacgt    5520
ttaccaagtg cctactgtgt gctgcagagg cgaagatgac acagctcagg ccttttccctt    5580
gagcttacag ttcaggagga gagactgacc agtgactgcc agtacagttg actatgggac    5640
aatgtgctca gccttgggga gagacgaaga aggtacccgt atagcaccag atgacaggca    5700
cgagccccac aggccagggc agctgctcag aggagagtag gccaagcaga aggcaaacag    5760
aaggctgcag gcatttgcca tcgagagctg gacttcaaac tgggcatcat accagcctgg    5820
gttcgagtcc tgcccagccc cttattggct gtctaaccct gagcaaatcc cttcacctct    5880
ctgagcctca ttcctctatc tgtaaaccag ttataataat tggaacattc atttaaggac    5940
taaatgaggt cgtgaagcat tcagcagatg ctaggtacgg aaactcgctg aagtgggggc    6000
aggttaagaa gcctctgggg atacgaaggc atccagggac tagttgtggc aggaggctgt    6060
taccacttag gtctgaaggg taaggagagg gaatagcttt ccctctgccc agttggagcc    6120
ggtggcatgg aggagaggct gcctgtgggg aatcacccga gggttcaccg ctgccatgcg    6180
cagggagtca ggaggtaggg agggagtggg gcagatgcac accatttttt ttttttttg    6240
agactctgtt gccagactg gagtgcagtg gtgccatatc tgcacctctg cctcccgggt    6300
tcaagctcac tgcaacctct gcctcccggg ttcaagcgat tctcctgcct cagcctcccg    6360
agtagctggg actacaggtg tgtgccacca tgcctggcta ttttttgtat ttttaataga    6420
gatgggtttt caccatgttg gccaggctgg tctcgaactc tcgacctcag gtgatccccc    6480
acctcggcct cccaaagtgc tgggattaca ggcgtgagtc accgctccca gctgctgatg    6540
```

-continued

```
cactcttgtc cttctaactc ctgctagtgc ctcccattgg ctgagcccaa ctggaagctt   6600
tgcaagggag ctggtgctgc agtttgcact gagcaggctg gagaaggctg gagaatagac   6660 tagggggacaa accgaattgc cagtgctgtt atgtcatgat ttaggcatgg agtccagggc   6720
ctgagcttca ctccatgtcc atcctgccca gagccttggc acagcctggc tcccagacaa   6780
gatgtcaagt tcagaatcct tcctaaaagg aatcctctat gccagaccgt gttgcaggga   6840
tatgggagtg ctgggctccc agcctgatca aggagcgaga aaactcaggc tcctagtctg   6900
tcctccgggg cactagcagg gacaaggtgg gaggctgctg ggctgggatg tggggacagg   6960
tttgatcagg taaggccagg ctgtggctgt gtttgctgct gtccaaatgg cttaagcaga   7020
gtcccccggc ctctctggct tctgcaggcc ttgaagttgc cccatgtcga ctacatcgag   7080
gaggactcct ctgtctttgc ccagagcatc ccgtggaacc tggagcggat tacccctcca   7140
cggtaccggg cggatgaata ccagcccccc ggtaagaccc ccatctgtgc cctgcccac    7200 cccatctgag ctgaatccat ttgctctgcc ctggcctggc ctccctgctg gtggtttcca   7260
cttctcgggg ggctttggga ctcagcacct ccactgaccc cttttttct gtcccatccc    7320 catcccctgc agcccccact gcctgccttc ctgttgcccc acaaatgcaa aagtcttgcc   7380
ttaaatgatc ctctttttcct tcttttctct tgttttcctt ttctcaccat ttggaatggc   7440
ccagcaggct gcacttacct tggaaggagg gttcatctga tggtgactct acctagggcc   7500
cccaggcctc tataactccc agtgccctgc agactggacc agatccttta atgggataga   7560
cacaaccctg tctgggatgc ctctgcctac cttcctgttt tgctgctcca cctgcctcca   7620
gctccgtttg gcttcctggg gctccctgcc tgggccactt tgtgtcttcc ctctaggcct   7680
ttctttccac tgttccctct gcctggtgtg gcctggctat ggaagggagg gaggaggagc   7740
ggccatggaa aacggtctgc attctagcag ggacttgcag gtggcaattc agtcggggaa   7800
gactctagat gcacctggcc tgaggagaga atgaagggtt ctagttggac tgtgttaagt   7860
ttgaggtgcc catggtgtga ggtctggagc tcagcgcaga gatgatgcaa tgtggtgggt   7920
ccatgcaaca tggtgccagg acgcagagct tggggtgaac tcagctttca cccccttaccg  7980 gttctcgtgg gatcttggga agccacttc ttctatgagc tttgtcgttc ttgtctgtaa    8040
aatgggcaca taaccctgtc cctgtccttc tcacaggttg ctgtgagact ccaatgagtt   8100
gaaggatgtg cagatgcttt tggaagtgaa aagttggggg gctactgtgt gactttgcat   8160
acacccaaac tgtgtgacct tgcatatgtc tgagttgctg ccattgcaac agatcagagc   8220
tggtgggctg ggtgtggaga aagggtttgt gtggggaca tcctctggca agggtggcag    8280
cagcagaagt gaggggcctg gtcggtcatg tgtgctgacc cggcctgggc agcctgtggc   8340
cagggagagg acagctcctc tgtaggaaga gcctgttcct ttccaaccag gtgagacctc   8400
ttcagtggag ccctggagcc cctgtactc cacatcagtg cctcagggac ctcccggagc    8460
aggctaatat cagagaccaa gagggacact ggcagaggat cacagagacc ccagtccagg   8520
cagggactga aagatcttg cccctaagt tagtttccta gcactgctgt gacaaattac     8580
caccccctcg gttggaacaa gttgattctc tgcagtcctg gaggccagaa gcctgaatca   8640
gtgtcggcag gaccactttc tcccgggggg ctccaggag aagcttctct tgcctcttcc    8700
gtgtcccaac agcggcagca caccaatccc agcctctgtc ttcacacagc cttctctgtg   8760
tctctctcct cttcattgtc tcataaggac acttgtcatt ggatttaggg cccactggat   8820
cctccaggat gatctcatgt ggggaacctt aaccacatct gcaaggaccc ttttccaaa    8880
```

```
taaggtcaca gccacaggtt gtggggggtta ggatgtgagt gtatctcttt ggcagccact    8940
gttccctcct ctcccttggg ccagaagcag acgtggggcc cttcttccc cataggatgc    9000 ccatggattg ccccccttcc cgcttccccc gagtgtctgt gggaggtggc aggaatggca    9060
ggcaggggtg tggaaccccct tctggagtca tatcaagggc ttggctggag gaagtcctcc    9120
tggagctgtt gggctggcat ggggcaggct ggctgggccc agcagcagct tcttcattca    9180
tggggaggcc acaagcatgg gccctagagc tggctgccgc cctcaaaccc agaccctgca    9240
ctcttaactg tgtgaccttg catacgtcac tcaccctctc tgatcttcag gttcctctgc    9300
aaaagggagg taatgataac cctcactctg ggggctgtt tggagggtta aatcagttat    9360
tgctgtagca tgcatttctc tgtcaggtat tgagtgaggt gctgtgattt tagccctgca    9420
ttttttcttt cttaccattc aataataacg ttttgagcac ccactgtgcg ccaggcacca    9480
tattaggtgc tggggataca aatgtgaatg aaatgaatgt ggtctcttcc cccaacagtg    9540
tatccagaag attaatccat tccttaaaca aatgctactt gacacagatt agttctggat    9600
aggctgagag ctctgaagga gtgcaggcag ctgcagcct gtgtatccag cagaaggatc    9660
aggaaaggat tcctggagga agcgctgttc tagccaagac ctacggggc attattaacc    9720 aggcaaaggg gacggtgtcc aagcagtgga atgaacgtgg attgaagctg tgaggcagga    9780
gggagtgtgg cctgtgcaga agggaccgag gctggtgaga ccaggagggc ctgggtggcc    9840
tccaggtcag atgtgaaagg aagaacttgg ccacagtctg agcttctcag gcgtatggca    9900
gggctgcctg gtgagaggga atgagctccc tgctctggag gtatgcaagc aggactgggc    9960
tctcacctgc cagaggccac agagctttcc agaggctgga agaggccact ccaaggcctc   10020 tttgccccctg agagtggtgg ctcttcttga ggccaccttg ccacgctgtc acagggaact   10080 agcagccct gcctcacccg ggggtttgga agatagaggg aggcctagga agggccctgt   10140
gtctcatccg agctgggccc ctttccagcc tctcactgga aggaagccca aggatgttcc   10200
tgtgggggct tttaccaggc ccacctgccc tctgctggcc atgcttgcag cctcctgacc   10260
ctgtcccagc aggacagtgg gctggtgtga gcgggcagga accgctgca cttagaaggt   10320 gtgggctgc ctccccgagc ttccatctgc cgctggggcc acaccccagg cccagggatg   10380
ggaccccaca gtggtcacat catcttgcag cagaacccag gtacagctcc tggagcagat   10440
ggtggtccca agcacgggtg ggaccagaaa ggactctcac ctgggctaac tcagctgcag   10500
cctcagttcc ctcctcacac acgacgagga acatggactg gaagcctgcc cagcaggcct   10560
tctgctcgat gtgcgttgtg tggcttacgt ccagggaggg aagcagcctc tgtgctgtct   10620
tctagataag cctgtattcc ccgggctgtc tgccaatgta tccagttgtc ccgtcagcct   10680
ggaagctctg agggaaaaacc ttgggctgct tcctgagcac ctgtatcccc tgcagccagc   10740
ccggggcctc tgctaggagc agactgagca tggcttatgg gcctggcacc atctggcctc   10800
tgcccacctt gctggccttg tcttgtgtct gcccccttcga cattccatag cccagctcaa   10860
tatctagtgg ttcctctagg gtggcgagca ctgtttggtc tccagatgtc ttcaggtcgg   10920
agctcacagc gctctcagcc acccccttccc agtgtagcac cgggcacatg gtagatgcct   10980
attgatgagt gaaagctcct aacacactca gagagcaagg actccgcctc atcccacagc   11040
ctgggaggag aggcagactg ccaaggacct gctcagcatg ctacagaaga aaccaaagtg   11100
cccacgggac tgatcagtgg agcttcctgc cgagactgga ggcctagggg cagggtagac   11160
agtgtgtgtg caggctgggg actcacagtt cggactgtgc ccagacctac tagcatagtg   11220
ggtgggtggg aggatgcggg actgggggcc gaccttgcct gaaattcatg tgggatctca   11280
```

```
gagcagccac tgaattgctc tgtaggggc taaatagtgg ccccacaga tacacacacc   11340 cagacagagc ctgtgagcca gaccttattt ggagaaaagg tctttgtaga tgtaattaag   11400
catctcaaga tggcatcatc tggattatgc ggtgggctgt aagtcctgtg atgtgtcttt   11460
atgagagaaa ggcagaggga gatttgacac acacaggagg ggccacgtgg agacagaggt   11520
ggagattgga gaaatgtggc cacaagccag ggaacaccag cagccaccag aagccggaag   11580
acgtgaggca gggttcttcc cagagccttc gctgctgagt ctgggaattt gtgaccgaag   11640
ccataagaag tgggtacacg ccctgagcct cccacacttg ctcacctgtc ctgagatgag   11700
aatctctact ctgcagcata tttggaggat cactgcgggg gccacagagg tgctgttcag   11760
atggcacttc agaagactca ggagaccctg gggcaggagc agtttgactg acagcccaga   11820
gggctgccct ctgattccac ctgaggccct gcttttcctg gctgcagggg ttccagggcc   11880
aggccatttc cgctggcgca ggactctgct agcagcaacc tgcctgaagt cttcctttgg   11940
cctggctgag agtttctgag acctgcgctg gagcggaggt gcttccttcc ttgcttcctt   12000
tcttcctctc tcccttctcc atccagcagg ctggacctgc ctggcatctg tgagctctcc   12060
ctactttctc ctatacccta acctttgtcc tgcatgggcg actcccccag tgagtctctt   12120
gcagctttta ccccagtgcc tgcttcttgg agaatccaaa ctgatccagt tagggatgat   12180
aaagtgtagg gtaggcgctc ggtgactgtt ttctctgagg ttgtgactcg tgtgaggcag   12240
aagcagtccc cgtgagccct cctggtatct tgtggagtgg agaacgcttg gacctggagc   12300
caggaggccc agacatacat cctgtccgag ctgcagcttc ctgtctctaa aatgagccgg   12360
ccagcgcagg tggccagaca tcactgttat tctcctttga gtctttaaat cttgttgtct   12420
ttcttgcaga ctcggtgagc tgtgaaaggc tataataggg gctttatttt acactttgat   12480 actattttt gaacattcat attattgtta gatattgata ttcatatgaa ggagcaggat   12540
gacttgggtc cttcttggca gtagcattgc cagctgatgg ccttggacag ttacctgccc   12600
tctctaggcc tcccttttcct tgtctatgaa atacattata gaataggatg tagtgtgtga   12660
ggattttttg gaggttaaac gagtgaatat atttaaggcg cttttcaccag tgcctgggat   12720 gtgctctgta gtttctgtgt gttaactata aggttgactt tatgctcatt ccctcctctc   12780
ccacaaatgt cgccttggaa agacggaggc agcctggtgg aggtgtatct cctagacacc   12840
agcatacaga gtgaccaccg ggaaatcgag ggcagggtca tggtcaccga cttcgagaat   12900
gtgcccgagg aggacgggac ccgcttccac agacaggtaa gcacggccgt ctgatgggag   12960
ggctgcctct gcccatatcc ccatcctgga ggtgggtggg gactgccacc ccagagcgtt   13020
gcagctgtac tcctgggttg cacccccccc agctgtcact gtcccctccc tgccatcagt   13080
tgtgggaagg gcgttcatcc atccagccac ctgctgattt gttatagggt ggaggggggg   13140
tctttctcat gtggtccttg tgttcgtcga gcaggccagc aagtgtgaca gtcatggcac   13200
ccacctggca ggggtggtca gcggccggga tgccggcgtg gccaagggtg ccagcatgcg   13260
cagcctgcgc gtgctcaact gccaagggaa gggcacggtt agcggcaccc tcataggtaa   13320
gtgatggccc cagacgctgg tctctctcca tctggacctg gcctgggagg tggcttgggc   13380
tgggcccagg gagagctaat gtctcctaac caagaatgct gtggcagcct ctgccgcaga   13440
gccagagaac cagagtgcca aggctggcag ggttcccagt ggccacgagt gcagatgaag   13500
aaacccaggc cccaagaggg tcatgcaggt agcccaggga gttcagcctt gaccctgggt   13560
caatgacctt tccacagttc cacactgctc ccctttttaaa atccggtgat gtctttatgt   13620
```

```
cttttgttat gttatcttca atgtggaggg actcgaggtg atctaagcaa acttttttcta    13680 tcttctgctt gcatacctct gagaccaggg gactcactca cttgcatgac tgggccctgc    13740
aggtcacact ggccaggcag atgtggtgga ggaactggca gaggactttt tctagactgt    13800
gactacattt agtccaccca gcggcccccc tatgaagtcc agttgagaac taggactctg    13860
ggggccggtg gacagagaag agggagggtt ctctcccctta ctgacttcct tctgtggcca    13920
gacattgagc aaggcctctg tacagcatgt cctggggctg gccttgccgt agctgctaaa    13980
tagttgacga aaccagtcca gagaggggag gtgactgcca gggtcgcaca gctcaagctg    14040
gggaactcgc tgggaaaact gtcagctctg ggcagcagct tgacttccac tgtaagcccc    14100
agcccccagg gtcaaacact ggctctggtg ctggcagagg cagcccacta gcctgtttca    14160
aaggctgaga aggcccagga gtctgccctg tgctccacca gttctgccct gagactttcc    14220
tacagagtac aggttttgat gttcagtttt aaaggcaaga atcaataacc ttctgcccca    14280
tcaggtgacc ccttgtgcct gtcccacccc tttattgact gacctcggct cagtcaggtc    14340
agttcctgaa ggtcagtgtg tggaggggag gctgttcttt cccagaaagg ccttcccccag    14400 gcctggtgct ctggcctctg gaggacttcc tggagaagtc ccttctttgg ggtcccagtc    14460
agtgtatggg aagcccttat tgcatgacct ggcacggggc aggggctcaa cagtcactat    14520
tgccttcctt gccactgcca tttcctcctc tgtaagcagg tgattgtgtg tccagtctga    14580
gcacagagat aagcacacag caggtgctta ataactagca gctgtaggct gggcgcggtg    14640
gctcatgcct gtaatcccag cactttggga ggccgaggtg ggcagatcac ctgaggtcag    14700
gagttcgaga ccagcctgtt caacatggtg aaaccccgtc tctactaaaa atacaaaaat    14760
tagccaggca tggtggtggg tgtctgtatc ccagctactt gggaggctaa ggcaggagaa    14820
tcgcttgaac ccaggaggtg gaggttgcag tgagctgaga tcgtgccact gcaatccagc    14880
ctgagtgata gagcgagatt ccatctcaaa aataaataag taaataacta gcagctgtaa    14940
atgtggctgt tgttcttcac ctccacactc agtgccactc cactccctcc ctccgtggtg    15000
tgaggggcct cactagctgt ctcctaggag gagcatggct gtgagattcc agctccatcc    15060
ttggccacgg ctcctggaga catcttagag gccaggatcc agaaggctcc cacacctcat    15120
ttgacagggg agaagctgtc agttccaggt ccccttgcac atcagggcca gagctgcgtt    15180
aggcctccag tctccaggcc actgggccag agctcacagg ctggcagagg gttagaactg    15240
ttactggtgg ctgggtgcag tggctcacgc ctgtaatctt agcactttgg gagggcaagg    15300
cgggaggatc atgaggtcag gacatcgaga ccatccttgc taaacacggtg aagcccgtc    15360 tctactaaaa ctacaaaaaa ttagccgggc gtggtggcag gcgcctgtag tcccagctac    15420
tcaggaggct gaggcaggag aatggcgtga acccgggagg cggagcttgc agtgagccga    15480
gattgcgcca ctgcactcca gcctgggcaa tagagcgaga ctccgtctgg aaagaaaaaa    15540 aaaaaaaga gctgttactg ttgacagtag catgaggtag accatggcct gcaccaaaat    15600
gggggagtgg agtgccactg aggccagaag gaaccacacc ctcaagggtg gggagttatg    15660
gtatgggggg tcctaggcat ggagtctttt aattctttag acaatcctgg gagcaactgt    15720
ccctgtttca cagagggcgg ggccacacag ctggtgagtg ggcagccaag actctgttca    15780
agtttgtgtg gtccaacac ttgcggccac ggtggagggg catctgagcc aggcctcaga    15840
gagtggcggg ggaagttggg tggggaagtg tgcccttctc attcctctga ggctcatcct    15900
cttggtgcct ctctttcatg gaaagggata ataaggttat tgtgaggatc ccctgagttc    15960
gtatattcag acgcttagac agagccaggc acagagaagg gcccggggtt ggctagtttg    16020
```

```
attgctggtg taattgctaa tatcttccag tttgtattgg tcaaggttct gcagagaagc    16080
agaaccagta ggatgtatat attaagagtt tcaagctcat gtgaccgtgc gggctggcaa    16140
gtctgaaatc cgcagggcag gccaggcagg ctggcaattc ctgcagaatt tgatgttgca    16200
atactgagtc ctaaggcagt cctggggcag aattccttct tccctgggag gcctcagtct    16260
gttctcttaa ggccttcaac tgattaaatg aggcctgccc aagttataga gagtaacctg    16320
ccttactccg tcttctgatt taaatgttag tcacatctaa aaaatatttt cgcagcagca    16380
tttccactgg cttttgacca aacatcaggc cacaaagttg atccccaaaa ttaaccatca    16440
ctctgtgcct gtaagggagg ggctgggaaa ggggagcagg tctccccaag gggtgacctt    16500
ggctttgttc ctcccaggcc tggagtttat tcggaaaagc cagctggtcc agcctgtggg    16560
gccactggtg gtgctgctgc cctggcgggt gggtacagc cgcgtcctca acgccgcctg    16620
ccagcgcctg gcgagggctg gggtcgtgct ggtcaccgct gccggcaact tccgggacga    16680
tgcctgcctc tactcccag cctcagctcc cgaggtaggt gctggggctg ctgccccaag    16740
gcgcgggtag ggggcggagg gcggagggcg gagggagggc gggcgggcag gcgggcttct    16800
tgtggcacgt gggcttcttg tggcacgttc ctggaggccg aacccttctg ctttggaag    16860
gagtcgtcag agaccccgc catgcgggag gctggggagg aaggggctcg aaacctccat    16920
catcgcagag tctgaatagc agtggccccg ccatgcgccc acgtagcggc gcctacgtag    16980
ccacgccccc acacccgtc ctggccactc tccctcctga aggtcttctg gtacccgccc    17040
cctccccatc tccatcccca ggccctgcgt cctctgccca atactctttg ggcctccctg    17100
ttgtccagct ctctccgcgg ctccatgact gacaacttga gcaaggctaa tgtgaatggg    17160
agcggttgag ggctcagacc tctcacccga ggaacatcca cagagtgtgc cgcatgcccg    17220
gtgcagtgtg gctgcgggga cacagacacg gagcctcggc cctgaggagc tgggggggcag   17280
tgaccgtccc tcctctgacc caccactcct ccagtgtcag gacactgcgg gtatctaggg    17340
gaaggaatct tgttccactt caagtctgga acttcaagtc tgtgtgtgtg cgtgcgcgcg    17400
cgcgcgttgg gggtgggggt tgcagagcag atgcgtacct gacagcggta acctaggtcc    17460
cccctggcct atcaaggctt ccctggcggc cgaatttaaa ggcatcaagc aaacaaagcc    17520
caacacatct ctgccttgtc ctctcagttt cccccgtgg cacttagaac cacttgatac     17580
accgaatagt ttcctatctc ccccactagg atgtaaactc cacaggggca ttgggaatgc    17640
tgcctggcta tggtagggac agaggggagc accagggcgg ggcaggggtg ccagagttct    17700
gcctgggcag tcagattttc cttaggaggg gacatttgag tgggacccaa acaggtgtat    17760
agcagttgtc cagcccagct ggcaaggcct gagtctgcct ctgcaacccc tctcttgggc    17820
tcctttctct gccacccacc tcctcacctt tccaggtcat cacagttggg gccaccaatg    17880
cccaagacca gccggtgacc ctggggactt tggggaccaa cttggccgc tgtgtggacc    17940
tctttgcccc aggggaggac atcattggtg cctccagcga ctgcagcacc tgctttgtgt    18000
cacagagtgg gacatcacag gctgctgccc acgtggctgg taagtcacca ccccactgcc    18060
tcggccaccg tgatgctaac agccccttg gcagtcaggg tctgtgccgg gacctccagt    18120
gccaggctct gtgcaggggg accagagatg aagtaggcct gatggtgcct tcaaggacac    18180
tcagtctgat gagggaggcg agtgcacaga ggaaacacga ggtcagggct gtattagagg    18240
gagcccagag gaggcacctg cccagcccga gggtcagaga aggcatcttg gaggagggac    18300
atttgatcgg gagcttgatg gatgaatagg agttcacctg gccgataaga cagcaactac    18360
```

```
caaggcttag aggtgtgaga ggaggctgtc ttacctcact gagtaaggac tgcaggcggc    18420
ttaccttcga gaagagagct tagtgtctgt gtgcacgtgt gtttgtgtgt atgtgtgtgc    18480
gtgtgtgcac tggcaggagt cccctgctgg ggcaggaggg ccgggccatc accatctttc    18540
accattcacc cctgcaccag gcattgcagc catgatgctg tctgccgagc cggagctcac    18600
cctggccgag ttgaggcaga gactgatcca cttctctgcc aaagatgtca tcaatgaggc    18660
ctggttccct gaggaccagc gggtactgac ccccaacctg gtggccgccc tgcccccag    18720
cacccatggg gcaggtaagc aggatggcag ggtgggcaag tccaggctgg ggcttgggag    18780
gtctgtgtga ccttgacagt ctctcccttc tcccttgtct gtgtaaggag gatgacgcca    18840
ccttaaatag gattaaatga gaatgggcgt ctgaaagggc tgtgcaatat tttcataacg    18900
tgtttttata gagacagttg agtatgttct ttaagccctc ctctctccta ccatgaacta    18960
aagatttctg tggaggtccc ctcactccca gcacccctc ctcatcccag gccttttg    19020
caggttggca gctgtttgc aggactgtat ggtcagcaca ctcggggcct acacggatgg    19080
ccacagccgt cgcccgctgc gccccagatg aggagctgct gagctgctcc agtttctcca    19140
ggagtgggaa gcggcggggc gagcgcatgg aggtgactgt acccctcctt cgtgtgtgtg    19200
tgtgtgtgtg tgtgtgtgtg tgtgtgtgtg tgtgtgtgtg tgtcagtgct gggccctcag    19260
ggaccccag caagccctc catcctccag actccagctc ttctgtaagc ttacagggct    19320
ggccagacca ggagtggggc actcctcact tcacgcggct gggggctgct ggagagagcc    19380
acagcgggaa gggtttccta gaggctgcag gacagtgctg gatggatttt caatgctcac    19440
ctgggtgtga gcgtgcggca gggccgcgtg agggtcagcg atctgctact ctggactcag    19500
ccatctctag gcccctctca ctcaggtgct ccatggttct gggagctgag aaatctcaaa    19560
ccagcaaaaa agtggaattg atgttgatgc tacaggatag tgcacagatg ccatctggtt    19620
gcagcatttt ggtggaaggg cagtgcccag ctaggagagt gaggaggggc aggcatttct    19680
ggcttgagga gatgggtct taatgctcgt gtgagaggca gagtgggtgg agtggagctg    19740
gctggatcct tgctttggcc tcctggattt ctctctatct ccatttgaa accactctgt    19800
gtttggaaga acttttgagt attcagagct gcccactggc agaacagtct tccttgggca    19860
ggagtgagct ccttgtcccc agaaggctgg gtctggctgg ccctggcag ggacactgat    19920
gagggtgctt gagttgatcc tgtctagtcc cttctgtgt tttcaaagcc cattctaaag    19980
cagattccca tttccgtctt tgactctaag gcccaagggg gcaagctggt ctgccgggcc    20040
cacaacgctt tgggggtga gggtgtctac gccattgcca ggtgctgcct gctaccccag    20100
gccaactgca gcgtccacac agctccacca gctgaggcca gcatggggac ccgtgtccac    20160
tgccaccaac agggccacgt cctcacaggt aggaggctgg gcttgccctg gggtgaggag    20220
gggtctcttt ctccttatgc acccactgcc cgcgaggctt ggtcctcaca agtgtgatcc    20280
atgagactca agcctgactt gcagttccat actctggttc tgccacttcc atgccctttg    20340
agcctgggca ggtgaccta cttctcctca tctcagcttc ctcctccata agagggaaaa    20400
aggtattacc tgcctcattg tgttgcaagg agatgggcag catctagggc actggcctgg    20460
agtatcgcag gtgctttgcc taaggtggtg cagtccagga gaggcagctc cagagagagg    20520
cccccggctg gggctgaaag gagggcagac ctcggtttga atttcaccct gccgctctat    20580
agctgtgtga cttgggcaaa ttacttaaca tctctgtatg aggaaatgat gagtgctaag    20640
cacttagctt agtgccggga caatataaat tctagctatc gttactattg ttttcatcac    20700
ccgttgcttt aaaatccagc ctctggtata ggcaactatt gacgggctac cctgtgtcga    20760
```

```
aaacatgccc aggcaggtag caggaagtca cagatgggga cctcttgggg catcaaggga   20820
tggtgccctg aggctgagct gttctggttg ggtggagcat gagaggtctg ggaagacagt   20880
gggactccag cctggaataa gaggctcaga gttgattctc gtctgagcac gtccagggga   20940
accactgagg gtttgggaac aggagagtga gggtgagaac ctggttctgg gcacagcagg   21000
ctggcatgta ggatggatgt tcaggaaaga tgagcatagt caggtggctg gtgcccttgt   21060
ccaggggaga ggctccgtca ggttcagggg tcctggcttg gagggaagtc cgccatgctc   21120
taatcacgct cccctttgga agtgctcagc cgatgagctc acaggcacat gtcagtttga   21180
agtcatggaa tctgactcca tgaagcgcac ctcaaagagc accattttgc agctaaggga   21240
actgcaggct ggacatgctg agtggctgcc ccgagccctt gcagctagga catagagaat   21300
gctagtaacc acaaccctac catgttcaga gcacatgcca ggctccatgc tgggcttcg    21360
cacgtgtcat cttcacagtg tccctgtgag taggtgtggt ttctctttcc atcttacaaa   21420
tgagtaaaca gagcctcagt gtagctaagt aaccactatt ttaggtttct tagccaatgg   21480
gtgtgtctga ctcctaagcc catggagggc attctgaggt ggttcagaca daccccggct   21540
tacccttgaa cttctgcctg ctggctgcat agggaggggc tggggggagt ttgagcatct   21600
caggccatag agccctgcc tcactgtctc catctctggg tggaaagatg gtgttttccc    21660
tgagaaacta aggctcagag aggttgaatg gctctcccaa ggtcacacag ctggtcagct   21720
gcagagttga gaacacagga gtcctggtgc tcaggccagc atctctttt ttctttgagt    21780
tgtttctagg tttcctagct cttgcctcag accttaaaga gagagggtct gatggggatg   21840
ggcactggag acggagcatc ccagcatttc acatctgagc tggcttttcct ctgccccagg   21900
ctgcagctcc cactgggagg tggaggacct tggcacccac aagccgcctg tgctgaggcc   21960
acgaggtcag cccaaccagt gcgtgggcca cagggaggcc agcatccacg cttcctgctg   22020
ccatgcccca ggtctggaat gcaaagtcaa ggagcatgga atcccggccc tcaggagca    22080
ggtgaagagg cccgtgaggc cgggtgggtg gggtgctgcg tgtctctcct gcacagcttt   22140
tctgtgtcag tttgtgccac caccataccg ccatgcatca gggtggcggt ttgccaggta   22200
gatgctgtgg gcagcttccg ccattgtgtg gacagcatgt atatgtgtct ctgtgtggct   22260
gggtctgttt ttgcttttgt ccagatcagt aaggtttgct acctgggtac cccactccac   22320
ttggagtaga atgtgcataa atatggcata agaaatgca atatgcatgc atttattgat    22380
tgatctattt ttttctgaga tggggtcttg ctgtgttgcc caggctggtc tcaaattcct   22440
gggctcaagc aatcctctgg tctcagcctc cccaagtgtt gggattatag gcatgagccg   22500
ctgcacctgg cctctctgat ctatttaaca aacctgctgg gagggtctca gggtcaggag   22560
cagcactggg ctctgaggac acagagctca ctcagccgtg acccagaggg ggtgcctgag   22620
ctgcatgctg aaggttgtta gcatgaccag caaggcaaga aaaggccctg ccgagattag   22680
caaggcatgt gccaagccct ggaatgtgac agccgggcct tctagaaacc tgagtgtata   22740
actctcctta aaagccagta ggagctcctc aaaaggcagc cctaaggagt ccactcttaa   22800
atgaactcag agtcagttt aaaatgcaag tctgtgttga ttctggtctg gatggtgcat    22860
tcctcgagag caaaagacag tcttggtctt ggatccactt gccctgggta cactgagggc   22920
tgctaggttc caggtgctct tcctggcact ggggagggat acaggcccaa gagacatgct   22980
gttctccctc ctggagcatc tatttagtg gaggaagaca gaaaacaaac cattaatata    23040
gagtactgaa aagatgcgat ggagaaaact atagcaagga agggaatggg gtgggagaga   23100
```

-continued

```
ggtcaggaga ggtctcgctg acaaggtgga cgaaacaggc catgaggcag agaacatgtt    23160
ccaggcaaag caaaggcccc caggtgggga tgtgcaggga gtaccaggaa accagagagg    23220
tgggaatagt tatgagatgg ggggtgcctc agaggggaca gggccaagtc aggtgagacc    23280
tgagggtcac agtcagcagt gagctggggc catgcagggg tctggcctca gaggagtgtg    23340
gtctggcctg gatctgaacc tctcactgtg gcctagctgc tgagctgaga agagatgaca    23400
aggaccttgg gcagaagcag ggagactgga ggaggcggt ggagggtcca ggcgttgggg     23460
cggggctcag gctggagtct gaagggagcc tgcaggcctg gtgggtggat gtgggtggga    23520 gaggggagg atggcaccaa ggctcgggcc cctggacaga tggagttgcc attaagtggg     23580
atggggcagg ctatggggcc atcagtttca gagggatgag tttggcactg gcatggtagg    23640
catctgtcta tctccacggc cctcaaacca ggcatgaagc aggagctcac gtgtttggtc    23700
agccatggtg cagaaccgcc tgggtgggag gtgcggggtg ggagatacac ggttgtgtcc    23760
caaatgggct ctgagccagc gagggccgtc tgcactttgg cctcacagaa ggatgtcgga    23820
gggagaaatg aagtgtgggt gggggtcccg ggccacgcta gacatgtgct ttcttttcct    23880
cgggctctgg caggtgaccg tggcctgcga ggagggctgg accctgactg gctgcagtgc    23940
cctccctggg acctcccacg tcctgggggc ctacgccgta gacaacacgt gtgtagtcag    24000
gagccgggac gtcagcacta caggcagcac cagcgaaggg gccgtgacag ccgttgccat    24060
ctgctgccga agccggcacc tggcgcaggc ctcccaggag ctccagtgac agccccatcc    24120
caggatgggt gtctggggag ggtcaagggc tggggctgag ctttaaaatg gttccgactt    24180
gtccctctct cagccctcca tggcctggca cgaggggatg gggatgcttc cgcctttccg    24240
gggctgctgg cctggccctt gagtggggca gcctccttgc ctggaactca ctcactctgg    24300
gtgcctcctc cccaggtgga ggtgccagga agctccctcc ctcactgtgg ggcatttcac    24360
cattcaaaca ggtcgagctg tgctcgggtg ctgccagctg ctcccaatgt gccgatgtcc    24420
gtgggcagaa tgacttttat tgagctcttg ttccgtgcca ggcattcaat cctcaggtct    24480
ccaccaagga ggcaggattc ttcccatgga taggggaggg ggcggtaggg gctgcaggga    24540
caaacatcgt tgggggtga gtgtgaaagg tgctgatggc cctcatctcc agctaactgt     24600
ggagaagccc ctgggggctc cctgattaat ggaggcttag cttttctggat ggcatctagc   24660 cagaggctgg agacaggtgc gccgcctggtg gtcacaggct gtgccttggt ttcctgagcc   24720
acctttactc tgctctatgc caggctgtgc tagcaacacc caaaggtggc ctgcggggag    24780
ccatcaccta ggactgactc ggcagtgtgc agtggtgcat gcactgtctc agccaacccg    24840
ctccactacc cggcagggta cacattcgca ccctacttc acagaggaag aaacctggaa     24900
ccagaggggg cgtgcctgcc aagctcacac agcaggaact gagccagaaa cgcagattgg    24960
gctggctctg aagccaagcc tcttcttact tcacccggct gggctcctca ttttacgggg    25020
taacagtgag gctgggaagg ggaacacaga ccaggaagct cggtgagtga tgcagaacg     25080 atgcctgcag catggaact ttttccgtta tcacccaggc ctgattcact ggcctggcgg     25140
agatgcttct aaggcatggt cgggggagag ggccaacaac tgtccctcct tgagcaccag    25200
ccccacccaa gcaagcagac atttatcttt tgggtctgtc ctctctgttg ccttttaca    25260 gccaactttt ctagacctgt tttgcttttg taacttgaag atatttattc tgggttttgt    25320 agcatttta ttaatatggt gacttttaa aataaaaaca aacaaacgtt gtcctaac       25378
```

<210> SEQ ID NO 4
<211> LENGTH: 22

```
<212> TYPE: DNA
<213> ORGANISM: Homo sapiens

<400> SEQUENCE: 4
tggacctctt tgccccaggg ga                                              22

<210> SEQ ID NO 5
<211> LENGTH: 22
<212> TYPE: DNA
<213> ORGANISM: Homo sapiens

<400> SEQUENCE: 5
tcccctgggg caaagaggtc ca                                              22

<210> SEQ ID NO 6
<211> LENGTH: 354
<212> TYPE: PRT
<213> ORGANISM: Artificial Sequence
<220> FEATURE:
<223> OTHER INFORMATION: Synthesized

<400> SEQUENCE: 6

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Lys Pro Ser Gln Arg
            20                  25                  30

Ser Lys Phe Lys His Lys Leu His Leu Val Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Leu Asp Ser Gly Ser Val Ser Phe Tyr Ser Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Lys Pro Val Gln Arg Ala
    210                 215                 220

Lys Phe Lys His Glu Leu Val Leu Gly Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Lys Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
```

```
            275                 280                 285
Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 7
<211> LENGTH: 354
<212> TYPE: PRT
<213> ORGANISM: Artificial Sequence
<220> FEATURE:
<223> OTHER INFORMATION: Synthesized

<400> SEQUENCE: 7

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Leu Pro Ser Gln Arg
            20                  25                  30

Ser Lys Phe Lys His Lys Leu Arg Leu Val Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Leu Asp Ser Gly Ser Val Ser Phe Tyr Ser Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Lys Pro Val Gln Arg Ala
    210                 215                 220

Lys Phe Lys His Glu Leu Ala Leu Gly Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Lys Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
        275                 280                 285
```

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 8
<211> LENGTH: 354
<212> TYPE: PRT
<213> ORGANISM: Artificial Sequence
<220> FEATURE:
<223> OTHER INFORMATION: Synthesized

<400> SEQUENCE: 8

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Lys Pro Ser Gln Arg
            20                  25                  30

Ser Lys Phe Lys His Lys Leu His Leu Val Phe Cys Val Tyr Gln His
            35                  40                  45

Thr Gly Arg Arg Trp Phe Leu Asp Lys Leu Val Asp Glu Ile Gly Val
            50                  55                  60

Gly Tyr Val Ile Asp Ser Trp Ser Cys Ser Phe Tyr Ser Leu Ser Glu
65                  70                  75                  80

Ile Lys Pro Leu His Asn Phe Leu Thr Gln Leu Gln Pro Phe Leu Lys
            85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
            130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Arg Ile Lys Pro Val Gln Arg Ala
            210                 215                 220

Lys Phe Lys His Glu Leu Val Leu Gly Phe Asp Val Thr Gln Lys Thr
225                 230                 235                 240

Gln Arg Arg Trp Phe Leu Asp Lys Leu Val Asp Glu Ile Gly Val Gly
            245                 250                 255

Tyr Val Tyr Asp Lys Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
            275                 280                 285

```
Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 9
<211> LENGTH: 354
<212> TYPE: PRT
<213> ORGANISM: Artificial Sequence
<220> FEATURE:
<223> OTHER INFORMATION: Synthesized

<400> SEQUENCE: 9

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Val Pro Ser Gln Arg
            20                  25                  30

Ser Lys Phe Lys His Lys Leu Arg Leu Val Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Leu Asp Ser Gly Ser Val Ser Phe Tyr Ser Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Lys Pro Val Gln Arg Ala
    210                 215                 220

Lys Phe Lys His Glu Leu Arg Leu Gly Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Lys Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
```

290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 10
<211> LENGTH: 354
<212> TYPE: PRT
<213> ORGANISM: Artificial Sequence
<220> FEATURE:
<223> OTHER INFORMATION: Synthesized

<400> SEQUENCE: 10

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Lys Pro Ser Gln Arg
            20                  25                  30

Ser Lys Phe Lys His Lys Leu Leu Leu Val Phe Ala Val Tyr Gln Lys
        35                  40                  45

Thr Gln Arg Arg Trp Phe Leu Asp Lys Leu Val Asp Glu Ile Gly Val
50                  55                  60

Gly Tyr Val Leu Asp Ser Gly Ser Val Ser Phe Tyr Ser Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Arg Ile Lys Pro Val Gln Arg Ala
        210                 215                 220

Lys Phe Lys His Glu Leu Val Leu Gly Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Lys Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

```
Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 11
<211> LENGTH: 354
<212> TYPE: PRT
<213> ORGANISM: Artificial Sequence
<220> FEATURE:
<223> OTHER INFORMATION: Synthesized

<400> SEQUENCE: 11

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Val Pro Ser Gln Arg
            20                  25                  30

Ser Lys Phe Lys His Lys Leu Arg Leu Val Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Leu Asp Ser Gly Ser Val Ser Phe Tyr Ser Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Arg Pro Val Gln Arg Ala
    210                 215                 220

Lys Phe Lys His Glu Leu Arg Leu Gly Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Lys Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300
```

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
        340                 345                 350

Ser Pro

<210> SEQ ID NO 12
<211> LENGTH: 354
<212> TYPE: PRT
<213> ORGANISM: Artificial Sequence
<220> FEATURE:
<223> OTHER INFORMATION: Synthesized

<400> SEQUENCE: 12

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Val Pro Ser Gln Arg
            20                  25                  30

Ser Lys Phe Lys His Lys Leu Arg Leu Val Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Leu Asp Ser Gly Ser Val Ser Phe Tyr Ser Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Arg Pro Val Gln Arg Ala
    210                 215                 220

Lys Phe Lys His Glu Leu Val Leu Gly Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Ala Tyr Asp Lys Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val

```
            305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 13
<211> LENGTH: 354
<212> TYPE: PRT
<213> ORGANISM: Artificial Sequence
<220> FEATURE:
<223> OTHER INFORMATION: Synthesized

<400> SEQUENCE: 13

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Lys Pro Ser Gln Arg
                20                  25                  30

Ser Lys Phe Lys His Lys Leu Asn Leu Val Phe Ala Val Tyr Gln Lys
                35                  40                  45

Thr Gln Arg Arg Trp Phe Leu Asp Lys Leu Val Asp Glu Ile Gly Val
            50                  55                  60

Gly Tyr Val Leu Asp Ser Gly Ser Val Ser Phe Tyr Ser Leu Ser Glu
65              70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
            130                 135                 140

Ser Glu Thr Val Arg Ala Val Leu Asp Ser Leu Pro Gly Ser Val Gly
145             150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Tyr Ala Arg Ile Lys Pro Val Gln Arg Ala
            210                 215                 220

Lys Phe Lys His Glu Leu Val Leu Gly Phe Asp Val Thr Gln Lys Thr
225             230                 235                 240

Gln Arg Arg Trp Phe Leu Asp Lys Leu Val Asp Glu Ile Gly Val Gly
                245                 250                 255

Tyr Val Tyr Asp Lys Gly Ser Val Ser Ala Tyr Arg Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305             310                 315                 320
```

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 14
<211> LENGTH: 354
<212> TYPE: PRT
<213> ORGANISM: Artificial Sequence
<220> FEATURE:
<223> OTHER INFORMATION: Synthesized

<400> SEQUENCE: 14

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Val Pro Lys Gln Arg
            20                  25                  30

Ser Lys Phe Lys His Ser Leu Arg Leu Phe Phe Ala Val Phe Gln Lys
        35                  40                  45

Thr Gln Arg Arg Trp Phe Leu Asp Lys Leu Val Asp Glu Ile Gly Val
50                  55                  60

Gly Tyr Val Gln Asp Ser Gly Ser Val Ser Tyr Tyr Asn Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Lys Pro Val Gln Arg Ala
210                 215                 220

Lys Phe Lys His Glu Leu Ala Leu Gly Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Lys Gly Ser Val Ser Ala Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

```
Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 15
<211> LENGTH: 147
<212> TYPE: PRT
<213> ORGANISM: Artificial Sequence
<220> FEATURE:
<223> OTHER INFORMATION: Synthesized

<400> SEQUENCE: 15

Lys Glu Phe Leu Leu Tyr Leu Ala Gly Phe Val Asp Gly Asp Gly Ser
1               5                   10                  15

Ile Phe Ala Arg Ile Lys Pro Ser Gln Arg Ser Lys Phe Lys His Lys
            20                  25                  30

Leu His Leu Val Phe Ala Val Tyr Gln Lys Thr Gln Arg Arg Trp Phe
        35                  40                  45

Leu Asp Lys Leu Val Asp Glu Ile Gly Val Gly Tyr Val Leu Asp Ser
    50                  55                  60

Gly Ser Val Ser Phe Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 16
<211> LENGTH: 147
<212> TYPE: PRT
<213> ORGANISM: Artificial Sequence
<220> FEATURE:
<223> OTHER INFORMATION: Synthesized

<400> SEQUENCE: 16

Lys Glu Phe Leu Leu Tyr Leu Ala Gly Phe Val Asp Gly Asp Gly Ser
1               5                   10                  15

Ile Phe Ala Arg Ile Leu Pro Ser Gln Arg Ser Lys Phe Lys His Lys
            20                  25                  30

Leu Arg Leu Val Phe Ala Val Tyr Gln Lys Thr Gln Arg Arg Trp Phe
        35                  40                  45

Leu Asp Lys Leu Val Asp Glu Ile Gly Val Gly Tyr Val Leu Asp Ser
    50                  55                  60

Gly Ser Val Ser Phe Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 17
<211> LENGTH: 147
<212> TYPE: PRT
<213> ORGANISM: Artificial Sequence
<220> FEATURE:
<223> OTHER INFORMATION: Synthesized

<400> SEQUENCE: 17

Lys Glu Phe Leu Leu Tyr Leu Ala Gly Phe Val Asp Gly Asp Gly Ser
1               5                   10                  15

Ile Phe Ala Arg Ile Lys Pro Ser Gln Arg Ser Lys Phe Lys His Lys
            20                  25                  30

Leu His Leu Val Phe Cys Val Tyr Gln His Thr Gly Arg Arg Trp Phe
        35                  40                  45

Leu Asp Lys Leu Val Asp Glu Ile Gly Val Gly Tyr Val Ile Asp Ser
    50                  55                  60

Trp Ser Cys Ser Phe Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 18
<211> LENGTH: 147
<212> TYPE: PRT
<213> ORGANISM: Artificial Sequence
<220> FEATURE:
<223> OTHER INFORMATION: Synthesized

<400> SEQUENCE: 18

Lys Glu Phe Leu Leu Tyr Leu Ala Gly Phe Val Asp Gly Asp Gly Ser
1               5                   10                  15

Ile Phe Ala Arg Ile Val Pro Ser Gln Arg Ser Lys Phe Lys His Lys
            20                  25                  30

Leu Arg Leu Val Phe Ala Val Tyr Gln Lys Thr Gln Arg Arg Trp Phe
        35                  40                  45

Leu Asp Lys Leu Val Asp Glu Ile Gly Val Gly Tyr Val Leu Asp Ser
    50                  55                  60

Gly Ser Val Ser Phe Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 19
<211> LENGTH: 147
<212> TYPE: PRT
<213> ORGANISM: Artificial Sequence
<220> FEATURE:
<223> OTHER INFORMATION: Synthesized

<400> SEQUENCE: 19

Lys Glu Phe Leu Leu Tyr Leu Ala Gly Phe Val Asp Gly Asp Gly Ser
1               5                   10                  15

Ile Phe Ala Arg Ile Lys Pro Ser Gln Arg Ser Lys Phe Lys His Lys
            20                  25                  30

Leu Leu Val Phe Ala Val Tyr Gln Lys Thr Gln Arg Arg Trp Phe
        35                  40                  45

Leu Asp Lys Leu Val Asp Glu Ile Gly Val Gly Tyr Val Leu Asp Ser
    50                  55                  60

Gly Ser Val Ser Phe Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 20
<211> LENGTH: 147
<212> TYPE: PRT
<213> ORGANISM: Artificial Sequence
<220> FEATURE:
<223> OTHER INFORMATION: Synthesized

<400> SEQUENCE: 20

Lys Glu Phe Leu Leu Tyr Leu Ala Gly Phe Val Asp Gly Asp Gly Ser
1               5                   10                  15

Ile Phe Ala Arg Ile Val Pro Ser Gln Arg Ser Lys Phe Lys His Lys
            20                  25                  30

Leu Arg Leu Val Phe Ala Val Tyr Gln Lys Thr Gln Arg Arg Trp Phe
        35                  40                  45

Leu Asp Lys Leu Val Asp Glu Ile Gly Val Gly Tyr Val Leu Asp Ser
    50                  55                  60

Gly Ser Val Ser Phe Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser

Pro Asp Lys Phe Leu Glu Val Cys Thr Trp Val Asp Gln Ile Ala Ala
         115                 120                 125

Leu Asn Asp Ser Lys Thr Arg Lys Thr Thr Ser Glu Thr Val Arg Ala
    130                 135                 140

Val Leu Asp
145

<210> SEQ ID NO 21
<211> LENGTH: 147
<212> TYPE: PRT
<213> ORGANISM: Artificial Sequence
<220> FEATURE:
<223> OTHER INFORMATION: Synthesized

<400> SEQUENCE: 21

Lys Glu Phe Leu Leu Tyr Leu Ala Gly Phe Val Asp Gly Asp Gly Ser
1               5                   10                  15

Ile Phe Ala Arg Ile Val Pro Ser Gln Arg Ser Lys Phe Lys His Lys
            20                  25                  30

Leu Arg Leu Val Phe Ala Val Tyr Gln Lys Thr Gln Arg Arg Trp Phe
        35                  40                  45

Leu Asp Lys Leu Val Asp Glu Ile Gly Val Gly Tyr Val Leu Asp Ser
    50                  55                  60

Gly Ser Val Ser Phe Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 22
<211> LENGTH: 147
<212> TYPE: PRT
<213> ORGANISM: Artificial Sequence
<220> FEATURE:
<223> OTHER INFORMATION: Synthesized

<400> SEQUENCE: 22

Lys Glu Phe Leu Leu Tyr Leu Ala Gly Phe Val Asp Gly Asp Gly Ser
1               5                   10                  15

Ile Phe Ala Arg Ile Lys Pro Ser Gln Arg Ser Lys Phe Lys His Lys
            20                  25                  30

Leu Asn Leu Val Phe Ala Val Tyr Gln Lys Thr Gln Arg Arg Trp Phe
        35                  40                  45

Leu Asp Lys Leu Val Asp Glu Ile Gly Val Gly Tyr Val Leu Asp Ser
    50                  55                  60

Gly Ser Val Ser Phe Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 23
<211> LENGTH: 147
<212> TYPE: PRT
<213> ORGANISM: Artificial Sequence
<220> FEATURE:
<223> OTHER INFORMATION: Synthesized

<400> SEQUENCE: 23

Lys Glu Phe Leu Leu Tyr Leu Ala Gly Phe Val Asp Gly Asp Gly Ser
1               5                   10                  15

Ile Phe Ala Arg Ile Val Pro Lys Gln Arg Ser Lys Phe Lys His Ser
            20                  25                  30

Leu Arg Leu Phe Phe Ala Val Phe Gln Lys Thr Gln Arg Arg Trp Phe
        35                  40                  45

Leu Asp Lys Leu Val Asp Glu Ile Gly Val Gly Tyr Val Gln Asp Ser
    50                  55                  60

Gly Ser Val Ser Tyr Tyr Asn Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 24
<211> LENGTH: 147
<212> TYPE: PRT
<213> ORGANISM: Artificial Sequence
<220> FEATURE:
<223> OTHER INFORMATION: Synthesized

<400> SEQUENCE: 24

Lys Glu Phe Leu Leu Tyr Leu Ala Gly Phe Val Asp Gly Asp Gly Ser
1               5                   10                  15

Ile Tyr Ala Arg Ile Lys Pro Val Gln Arg Ala Lys Phe Lys His Glu
            20                  25                  30

Leu Val Leu Gly Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Lys
    50                  55                  60

Gly Ser Val Ser Ala Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 25
<211> LENGTH: 147
<212> TYPE: PRT
<213> ORGANISM: Artificial Sequence
<220> FEATURE:
<223> OTHER INFORMATION: Synthesized

<400> SEQUENCE: 25

Lys Glu Phe Leu Leu Tyr Leu Ala Gly Phe Val Asp Gly Asp Gly Ser
1               5                   10                  15

Ile Tyr Ala Arg Ile Lys Pro Val Gln Arg Ala Lys Phe Lys His Glu
            20                  25                  30

Leu Ala Leu Gly Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Lys
    50                  55                  60

Gly Ser Val Ser Ala Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 26
<211> LENGTH: 147
<212> TYPE: PRT
<213> ORGANISM: Artificial Sequence
<220> FEATURE:
<223> OTHER INFORMATION: Synthesized

<400> SEQUENCE: 26

Lys Glu Phe Leu Leu Tyr Leu Ala Gly Phe Val Asp Gly Asp Gly Ser
1               5                   10                  15

Ile Tyr Ala Arg Ile Lys Pro Val Gln Arg Ala Lys Phe Lys His Glu
            20                  25                  30

Leu Val Leu Gly Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Lys
    50                  55                  60

Gly Ser Val Ser Ala Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
```

```
                    85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 27
<211> LENGTH: 147
<212> TYPE: PRT
<213> ORGANISM: Artificial Sequence
<220> FEATURE:
<223> OTHER INFORMATION: Synthesized

<400> SEQUENCE: 27

Lys Glu Phe Leu Leu Tyr Leu Ala Gly Phe Val Asp Gly Asp Gly Ser
1               5                   10                  15

Ile Tyr Ala Arg Ile Lys Pro Val Gln Arg Ala Lys Phe Lys His Glu
            20                  25                  30

Leu Arg Leu Gly Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Lys
    50                  55                  60

Gly Ser Val Ser Ala Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 28
<211> LENGTH: 147
<212> TYPE: PRT
<213> ORGANISM: Artificial Sequence
<220> FEATURE:
<223> OTHER INFORMATION: Synthesized

<400> SEQUENCE: 28

Lys Glu Phe Leu Leu Tyr Leu Ala Gly Phe Val Asp Gly Asp Gly Ser
1               5                   10                  15

Ile Tyr Ala Arg Ile Lys Pro Val Gln Arg Ala Lys Phe Lys His Glu
            20                  25                  30

Leu Val Leu Gly Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Lys
    50                  55                  60

Gly Ser Val Ser Ala Tyr Arg Leu Ser Gln Ile Lys Pro Leu His Asn
65                  70                  75                  80
```

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 29
<211> LENGTH: 147
<212> TYPE: PRT
<213> ORGANISM: Artificial Sequence
<220> FEATURE:
<223> OTHER INFORMATION: Synthesized

<400> SEQUENCE: 29

Lys Glu Phe Leu Leu Tyr Leu Ala Gly Phe Val Asp Gly Asp Gly Ser
1               5                   10                  15

Ile Tyr Ala Arg Ile Arg Pro Val Gln Arg Ala Lys Phe Lys His Glu
            20                  25                  30

Leu Arg Leu Gly Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Lys
    50                  55                  60

Gly Ser Val Ser Ala Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 30
<211> LENGTH: 147
<212> TYPE: PRT
<213> ORGANISM: Artificial Sequence
<220> FEATURE:
<223> OTHER INFORMATION: Synthesized

<400> SEQUENCE: 30

Lys Glu Phe Leu Leu Tyr Leu Ala Gly Phe Val Asp Gly Asp Gly Ser
1               5                   10                  15

Ile Tyr Ala Arg Ile Arg Pro Val Gln Arg Ala Lys Phe Lys His Glu
            20                  25                  30

Leu Val Leu Gly Phe Asp Val Thr Gln Lys Thr Gln Arg Arg Trp Phe
        35                  40                  45

Leu Asp Lys Leu Val Asp Glu Ile Gly Val Gly Tyr Ala Tyr Asp Lys
    50                  55                  60

Gly Ser Val Ser Ala Tyr Arg Leu Ser Gln Ile Lys Pro Leu His Asn
65                  70                  75                  80
```

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 31
<211> LENGTH: 147
<212> TYPE: PRT
<213> ORGANISM: Artificial Sequence
<220> FEATURE:
<223> OTHER INFORMATION: Synthesized

<400> SEQUENCE: 31

Lys Glu Phe Leu Leu Tyr Leu Ala Gly Phe Val Asp Gly Asp Gly Ser
1               5                   10                  15

Ile Tyr Ala Arg Ile Lys Pro Val Gln Arg Ala Lys Phe Lys His Glu
            20                  25                  30

Leu Val Leu Gly Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Lys
    50                  55                  60

Gly Ser Val Ser Ala Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 32
<211> LENGTH: 147
<212> TYPE: PRT
<213> ORGANISM: Artificial Sequence
<220> FEATURE:
<223> OTHER INFORMATION: Synthesized

<400> SEQUENCE: 32

Lys Glu Phe Leu Leu Tyr Leu Ala Gly Phe Val Asp Gly Asp Gly Ser
1               5                   10                  15

Ile Tyr Ala Arg Ile Lys Pro Val Gln Arg Ala Lys Phe Lys His Glu
            20                  25                  30

Leu Ala Leu Gly Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Lys
    50                  55                  60

Gly Ser Val Ser Ala Tyr Arg Leu Ser Gln Ile Lys Pro Leu His Asn
```

```
                65                  70                  75                  80
           Phe Leu Thr Gln Leu Gln Pro Phe Leu Lys Leu Lys Gln Lys Gln Ala
                            85                  90                  95

Asn Leu Val Leu Lys Ile Ile Glu Gln Leu Pro Ser Ala Lys Glu Ser
                           100                 105                 110

Pro Asp Lys Phe Leu Glu Val Cys Thr Trp Val Asp Gln Ile Ala Ala
                    115                 120                 125

Leu Asn Asp Ser Lys Thr Arg Lys Thr Thr Ser Glu Thr Val Arg Ala
               130                 135                 140

Val Leu Asp
           145

<210> SEQ ID NO 33
<211> LENGTH: 19
<212> TYPE: DNA
<213> ORGANISM: Artificial Sequence
<220> FEATURE:
<223> OTHER INFORMATION: Gene-edited Homo sapiens sequence

<400> SEQUENCE: 33
tggacctctt tgcagggga                                                    19

<210> SEQ ID NO 34
<211> LENGTH: 21
<212> TYPE: DNA
<213> ORGANISM: Artificial Sequence
<220> FEATURE:
<223> OTHER INFORMATION: Gene-edited Homo sapiens sequence

<400> SEQUENCE: 34
tggacccttt gccccagggg a                                                 21

<210> SEQ ID NO 35
<211> LENGTH: 21
<212> TYPE: DNA
<213> ORGANISM: Artificial Sequence
<220> FEATURE:
<223> OTHER INFORMATION: Gene-edited Homo sapiens sequence

<400> SEQUENCE: 35
tggacctctt tgcccagggg a                                                 21

<210> SEQ ID NO 36
<211> LENGTH: 23
<212> TYPE: DNA
<213> ORGANISM: Artificial Sequence
<220> FEATURE:
<223> OTHER INFORMATION: Gene-edited Homo sapiens sequence

<400> SEQUENCE: 36
tggacctctt ttgccccagg gga                                               23

<210> SEQ ID NO 37
<211> LENGTH: 20
<212> TYPE: DNA
<213> ORGANISM: Artificial Sequence
<220> FEATURE:
<223> OTHER INFORMATION: Gene-edited Homo sapiens sequence

<400> SEQUENCE: 37
tggacctctt tgccagggga                                                   20

<210> SEQ ID NO 38
```

```
<211> LENGTH: 19
<212> TYPE: DNA
<213> ORGANISM: Artificial Sequence
<220> FEATURE:
<223> OTHER INFORMATION: Gene-edited Homo sapiens sequence

<400> SEQUENCE: 38
tggacctctt cccagggga                                                        19

<210> SEQ ID NO 39
<211> LENGTH: 19
<212> TYPE: DNA
<213> ORGANISM: Artificial Sequence
<220> FEATURE:
<223> OTHER INFORMATION: Gene-edited Homo sapiens sequence

<400> SEQUENCE: 39
tggacctctt tccagggga                                                        19

<210> SEQ ID NO 40
<211> LENGTH: 18
<212> TYPE: DNA
<213> ORGANISM: Artificial Sequence
<220> FEATURE:
<223> OTHER INFORMATION: Gene-edited Homo sapiens sequence

<400> SEQUENCE: 40
tggacctctt ccagggga                                                         18
```

ENGINEERED MEGANUCLEASES SPECIFIC FOR RECOGNITION SEQUENCES IN THE PCSK9 GENE

RELATED APPLICATIONS

This application is a national stage filing under 35 U.S.C. § 371 of international application number PCT/US2018/028607, filed Apr. 20, 2018, which claims the benefit of U.S. provisional application No. 62/516,966, filed Jun. 8, 2017 and U.S. provisional application No. 62/488,403, filed Apr. 21, 2017, each of which is herein incorporated by reference in its entirety.

FIELD OF THE INVENTION

The invention relates to the fields of molecular biology and recombinant nucleic acid technology. In particular, the invention relates to engineered meganucleases having specificity for a recognition sequence within the PCSK9 gene. Such engineered meganucleases are useful in methods for treating cardiovascular diseases and hypercholesterolemia, including autosomal dominant familial hypercholesterolemia.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 21, 2019, is named P109070022US02-SEQ-MJT, and is 89,660 bytes in size.

BACKGROUND OF THE INVENTION

Cardiovascular diseases related to high levels of low-density lipoprotein cholesterol (LDL-C) are a leading cause of death in developed countries, and elevated levels of LDL-C are a major risk factor for coronary artery disease (CHD) and the development of atherosclerotic plaques. For example, familial hypercholesterolemia (FH) is a genetic disorder characterized by high cholesterol levels, particularly high levels of LDL-C, and the development of early-onset CHD. Heterozygous FH patients are typically treated with lipid lowering agents, such as statins, that reduce total cholesterol levels and specifically LDL-C levels. Indeed, the administration of statins has greatly diminished the risk of cardiovascular disease in certain populations of patients. However, some patient populations, particularly those with homozygous forms of FH, are unable to achieve normal LDL-C levels in response to medical treatment, including high-dose statins.

A significant advance in the lipid-lowering field has been the development of therapies targeting proprotein convertase subtilisin/kexin type 9 (PCSK9). The human PCSK9 gene is located on chromosome 1p32.3 and is 25,378 bps in length. It contains 12 exons that encode 692 amino acids. The PCSK9 protein contains a signal peptide, a pro-domain, a catalytic domain, and a C-terminal cysteine-histidine-rich domain that is composed of 3 modules (M1, M2, and M3).

The synthesis, secretion, and expression of PCSK9 occur primarily in the liver, although PCSK9 is expressed at low levels in the gastrointestinal tract, kidneys, and central nervous system (CNS). The molecular weight of the PCSK9 precursor protein is 75 kDa. After autocatalytic cleavage in the endoplasmic reticulum (ER), the PCSK9 pro-domain is separated from the 62 kDa mature PCSK9 protein. The separated pro-domain remains non-covalently bound to the mature PCSK9 protein, forming a prosegment-PCSK9 complex that forces the PCSK9 catalytic domain into an inactive conformation. The cleaved complex is then transported from the ER to the Golgi apparatus and released. In hepatic cells, secreted PCSK9 binds to LDL receptors on the hepatocellular membrane. This binding is mediated by the interaction of the PCSK9 catalytic domain and prodomain with the epidermal growth factor-like repeat homology domain-A (EGF-A) and β-propeller domain, respectively, of the LDL receptor.

LDL receptors typically transport fat molecules in the extracellular fluid (including cholesterol) into cells, thus reducing circulating LDL concentrations. In the absence of PCSK9, an LDL receptor-ligand complex undergoes a conformational change which allows for intracellular delivery of the LDL and recycling of the LDL receptor back to the cell surface. However, binding of PCSK9 to the LDL receptor prevents this conformational change of the complex, and directs the receptor to lysosomes for degradation. As a result, fewer LDL receptors are present on the cell surface, which in turn increases circulating LDL cholesterol levels in the bloodstream. In addition to the LDL receptor, PCSK9 has been shown to mediate the degradation of other lipid receptors in the same family, including the very low-density lipoprotein (VLDL) receptor, the apolipoprotein E receptor 2, and LDL receptor-related protein 1.

PCSK9 was the third gene to be linked to the auto somal dominant form of FH, along with genes encoding the LDL receptor and apolipoprotein B. In autosomal dominant FH, gain-of-function mutations in the PCSK9 gene further decrease LDL receptor localization at the cell surface, and have been correlated with elevated levels of LDL cholesterol. Interestingly, it has been observed that loss-of-function mutations in PCSK9 were found in subjects who had lower LDL cholesterol levels and a significantly reduced incidence of cardiovascular events. Moreover, PCSK9 loss-of-function patients have been shown to have a heightened response to statin therapy.

Thus, targeting of PCSK9 is a promising therapeutic approach for the treatment of cardiovascular diseases and hypercholesterolemia, including autosomal dominant FH. Research in this field has heavily focused on inhibiting the interaction of PCSK9 with the LDL receptor using a number of therapeutics. These blocking approaches include the use of monoclonal antibodies against PCSK9, which include alirocumab (REGN727/SAR236553), evolocumab (AMG 145), and bococizumab (RN316). However, antibody approaches have been subject to neurocognitive adverse effects as well as problems that are typical of antibody therapies, including hypersensitivity reactions and immunogenicity. Blocking approaches have also been explored using adnectins and mimetic peptides. Thus far, the use of small molecule inhibitors of PCSK9, which are desirable from a therapeutic standpoint, have been largely unsuccessful.

Other approaches that have been pursued include the inhibition of PCSK9 expression. Such strategies include the use of antisense oligonucleotides or siRNAs to downregulate gene expression. Notably, gene editing approaches have also been pursued to permanently alter the PCSK9 gene and knockout protein expression. For example, Ding et al. utilized an adenoviral CRISPR/Cas9 system to target PCSK9 in mouse liver, finding that the mutagenesis rate of PCSK9 in mouse liver was >50% on days three through four, PCSK9 levels were reduced, hepatic LDL receptor levels were increased, and plasma cholesterol levels were reduced by 35%-40% (Ding et al. (2014), *Circ Res* 115(5): 488-492). In a further study by Wang et al. using Fah$^{-/-}$Rag2$^{-/-}$Il2rg$^{-/-}$ (FRG KO) mice, which have chimeric, humanized livers, treatment with CRISPR-Cas9 targeting the human PCSK9 gene induced high levels of on-target mutagenesis of PCSK9, resulting in a 52% decrease in the level of human PCSK9 protein in the blood (Wang et al. (2016), *Arteriosclerosis Thromb Vasc Biol* 36: 783-786). However, there is currently a notable lack of evidence in the art that a CRISPR/Cas system can successfully be utilized to modify and/or knockout genes specifically in primate livers, including human livers, which is necessary for a PCSK9-focused human gene therapy.

I-CreI (SEQ ID NO: 1) is a member of the LAGLIDADG (SEQ ID NO: 2) family of homing endonucleases which recognizes and cuts a 22 base pair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). Methods for rationally-designing mono-LAGLIDADG (SEQ ID NO: 2) homing endonucleases were described which are capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009), *Nucleic Acids Res.* 37:1650-62; Grizot et al. (2009), *Nucleic Acids Res.* 37:5405-19). Thus, a functional "single-chain" meganuclease can be expressed from a single transcript.

The use of engineered meganucleases could be a promising approach for targeting the PCSK9 gene and reducing PCSK9 expression, thus lowering circulating LDL and total cholesterol levels in patients with cholesterol-related diseases.

SUMMARY OF THE INVENTION

The present invention depends, in part, upon the development of site-specific, rare-cutting endonucleases that are engineered to recognize DNA sequences within the PCSK9 gene. The inventors have identified a specific recognition sequence in the PCSK9 gene that can reduce the expression and/or activity of PCSK9, and subsequently reduce the total and LDL cholesterol level in primates, such as humans.

Thus, the methods and compositions disclosed herein are useful in treating or reducing the symptoms of cholesterol-related disorders, such as hypercholesterolemia, including autosomal dominant FH in subjects. Accordingly, the present invention fulfills a need in the art for further gene therapy approaches to cholesterol-related disorders in primates The present invention provides engineered meganucleases useful for the treatment of cholesterol-related disorders, such as hypercholesterolemia, including autosomal dominant FH in subjects. The engineered meganucleases of the invention recognize and cleave a recognition sequence within the PCSK9 gene (SEQ ID NO: 3). Cleavage at such a recognition sequence by an engineered meganuclease disclosed herein can disrupt expression and/or activity of PCSK9 due to non-homologous end joining (NHEJ) at the cleavage site. NHEJ can result in insertions, deletions, or result in a frameshift mutation that can interfere with gene expression. Accordingly, by interrupting normal gene expression, PCSK9 expression and/or activity can be reduced or eliminated according to the methods disclosed herein. The present invention also provides pharmaceutical compositions and methods for treatment of cholesterol-related disorders which utilize an engineered meganuclease having specificity for a recognition sequence positioned within the PCSK9 gene. The present invention further provides methods for delivering the engineered meganucleases disclosed herein to a subject having a cholesterol-related disorder in order to reduce total cholesterol and/or LDL cholesterol level, and/or reduce symptoms associated with the cholesterol-related disorder.

Thus, in one aspect, the invention provides an engineered meganuclease that recognizes and cleaves a recognition sequence within the PCSK9 gene. The engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the recognition sequence can comprise SEQ ID NO: 4 (i.e., the PCS 7-8 recognition sequence). In some embodiments, wherein the recognition sequence comprises SEQ ID NO: 4, the HVR1 region can comprise an amino acid sequence having at least 80%, at least 85%, at least 90%, at least 95%, or more, sequence identity to an amino acid sequence corresponding to residues 24-79 of any one of SEQ ID NOs: 6-14. In some such embodiments, the HVR1 region can comprise residues corresponding to residues 24, 26, 28, 30, 32, 33, 38, 40, 42, 44, 46, 68, 70, 75, and 77 of any one of SEQ ID NOs: 6-14. In certain embodiments, the HVR1 region can further comprise residues corresponding to residues 48, 50, 71, and 73 of SEQ ID NO: 8. In particular embodiments, the HVR1 region can comprise residues 24-79 of any one of SEQ ID NOs: 6-14.

In some such embodiments, wherein the recognition sequence comprises SEQ ID NO: 4, the HVR2 region can comprise an amino acid sequence having at least 80%, at least 85%, at least 90%, at least 95%, or more, sequence identity to an amino acid sequence corresponding to residues 215-270 of any one of SEQ ID NOs: 6-14. In some such embodiments, the HVR2 region can comprise residues corresponding to residues 215, 217, 219, 221, 223, 224, 229, 231, 233, 235, 237, 259, 261, 266, and 268 of any one of SEQ ID NOs: 6-14. In such embodiments, the HVR2 region can further comprise a residue corresponding to residue 258 of SEQ ID NO: 12. In particular embodiments, the HVR2 region can comprise residues 215-270 of any one of SEQ ID NOs: 6-14.

In such embodiments, wherein the recognition sequence comprises SEQ ID NO: 4, the first subunit can comprise an amino acid sequence having at least 80%, at least 85%, at least 90%, at least 95%, or more, sequence identity to residues 7-153 of any one of SEQ ID NOs: 6-14, and the second subunit can comprise an amino acid sequence having at least 80%, at least 85%, at least 90%, at least 95%, or more, sequence identity to residues 198-344 of any one of SEQ ID NOs: 6-14. In certain embodiments, the first subunit comprises an D, E, Q, N, K, R, and S residue at a position corresponding to residue 80 of any one of SEQ ID NOs: 6-14. In certain embodiments, the second subunit comprises an D, E, Q, N, K, R, and S residue at a position corresponding to residue 271 of any one of SEQ ID NOs: 6-14. In certain embodiments, the first subunit comprises a residue corresponding to residue 80 of any one of SEQ ID NOs: 6-14. In certain embodiments, the second subunit comprises a residue corresponding to residue 271 of any one of SEQ ID NOs: 6-14. In some embodiments, the first subunit can comprise residues 7-153 of any one of SEQ ID NOs: 6-14. Likewise, in some embodiments, the second subunit can comprise residues 198-344 of any one of SEQ ID NOs: 6-14.

In certain such embodiments, wherein the recognition sequence comprises SEQ ID NO: 4, the engineered meganuclease can comprise a linker, wherein the linker covalently joins the first subunit and the second subunit. In particular embodiments, the engineered meganuclease can comprise the amino acid sequence of any one of SEQ ID NOs: 6-14.

In another aspect, the invention provides a polynucleotide comprising a nucleic acid sequence encoding any engineered meganuclease disclosed herein. In a particular embodiment, the polynucleotide can be an mRNA.

In further embodiments, the mRNA can be a polycistronic mRNA encoding one or more engineered meganucleases described herein. In further embodiments, a polycistronic mRNA of the invention can encode one or more engineered meganucleases described herein and one or more additional proteins that induce a therapeutically beneficial effect in a subject with a cholesterol-related disorder.

In another aspect, the invention provides a recombinant DNA construct comprising a nucleic acid sequence which encodes any engineered meganuclease of the invention. In some embodiments, the recombinant DNA construct comprises a cassette comprising a promoter and a nucleic acid sequence encoding an engineered meganuclease described herein.

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell.

In a particular embodiment, the recombinant DNA construct encodes a viral vector comprising a nucleic acid sequence encoding any engineered meganuclease disclosed herein. In such an embodiment, the viral vector can be a retrovirus, a lentivirus, an adenovirus, or an adeno-associated virus (AAV) vector. In a particular embodiment, the viral vector can be a recombinant AAV vector.

In some embodiments, the viral vector comprises a cassette comprising a promoter and a nucleic acid sequence encoding an engineered meganuclease described herein. In other embodiments, the viral vector comprises two or more cassettes, wherein each cassette comprises a promoter and a nucleic acid sequence encoding an engineered meganuclease described herein.

In other embodiments, the viral vector comprises one cassette comprising a promoter and a polycistronic nucleic acid sequence, wherein the promoter drives expression of the polycistronic nucleic acid sequence to generate a polycistronic mRNA described herein in a target cell.

In another aspect, the invention provides a viral vector comprising a nucleic acid sequence which encodes any engineered meganuclease of the invention. In some embodiments, the viral vector can be a retrovirus, a lentivirus, an adenovirus, or an adeno-associated virus (AAV) vector. In a particular embodiment, the viral vector can be a recombinant AAV vector. In some embodiments, the viral vector comprises a cassette comprising a promoter and a nucleic acid sequence encoding an engineered meganuclease described herein.

In further embodiments, the viral vector comprises one cassette comprising a promoter and a polycistronic nucleic acid sequence, wherein the promoter drives expression of the polycistronic nucleic acid sequence to generate a polycistronic mRNA described herein in a target cell.

In another aspect, the invention provides a pharmaceutical composition comprising a pharmaceutically acceptable carrier and: (a) a nucleic acid encoding an engineered meganuclease described herein; or (b) an engineered meganuclease protein described herein; wherein the engineered meganuclease has specificity for a recognition sequence within PCSK9, such as SEQ ID NO: 4.

In one embodiment, the nucleic acid sequence of the pharmaceutical composition encoding an engineered meganuclease disclosed herein can be an mRNA described herein. In some such embodiments, the mRNA can be a polycistronic mRNA described herein, such that two or more engineered meganucleases described herein are expressed in the target cell in vivo.

In another embodiment, the pharmaceutical composition comprises a recombinant DNA construct described herein comprising a nucleic acid sequence encoding an engineered meganuclease disclosed herein. In some such embodiments, the recombinant DNA construct comprises a cassette comprising a promoter and a nucleic acid sequence encoding an engineered meganuclease of the invention.

In other embodiments, the recombinant DNA construct of the pharmaceutical composition comprises a cassette comprising a promoter and a polycistronic nucleic acid sequence, wherein the promoter drives expression of the polycistronic nucleic acid sequence to generate a polycistronic mRNA described herein in the target cell in vivo, such that two or more engineered meganucleases described herein are expressed in the target cell.

In another embodiment, the pharmaceutical composition comprises a viral vector comprising a nucleic acid sequence encoding an engineered meganuclease disclosed herein. In one such embodiment, the viral vector can be a retrovirus, a lentivirus, an adenovirus, or an AAV. In a particular embodiment, the viral vector can be a recombinant AAV vector.

In some such embodiments, the viral vector comprises a cassette comprising a promoter and a nucleic acid sequence encoding an engineered meganuclease described herein.

In other such embodiments, the viral vector comprises one cassette comprising a promoter and a polycistronic nucleic acid sequence, wherein the promoter drives expression of the polycistronic nucleic acid sequence to generate a polycistronic mRNA described herein in the target cell in vivo, such that two or more engineered meganucleases described herein are expressed in the target cell.

In one embodiment, the pharmaceutical composition can comprise an engineered meganuclease disclosed herein which recognizes and cleaves SEQ ID NO: 4. In particular embodiments, the engineered meganuclease can comprise the amino acid sequence of any one of SEQ ID NOs: 6-14.

In some embodiments, the pharmaceutical composition can comprise one or more mRNAs described herein encapsulated within lipid nanoparticles. In particular embodiments, the lipid nanoparticles of the pharmaceutical composition can comprise two or more mRNAs described herein, each encoding an engineered meganuclease of the invention. In some embodiments, the lipid nanoparticles have a composition which enhances delivery and uptake in the liver, and specifically within hepatocytes.

In another aspect, the invention provides a method of treatment for reducing the expression or activity of PCSK9 in a subject. Likewise, provided herein is a method for treating a cholesterol-related disorder, such as hypercholesterolemia, including autosomal dominant FH, or reducing the symptoms associated with a cholesterol-related disorder. The methods comprise delivering to a target cell in the subject: (a) an effective amount of a nucleic acid encoding an engineered meganuclease, wherein the engineered meganuclease is expressed in the target cell; or (b) an effective amount of an engineered meganuclease protein; wherein the engineered meganuclease has specificity for a recognition sequence in PCSK9, such as SEQ ID NO: 4.

In some embodiments of the method, the subject has a cholesterol-related disorder. In specific embodiments, the subject has hypercholesterolemia. In some embodiments, the hypercholesterolemia of the subject is familial hypercholesterolemia or autosomal dominant familial hypercholesterolemia. In particular embodiments, the subject is a human or non-human primate.

In particular embodiments of the method, the subject is administered a pharmaceutical composition disclosed herein. The pharmaceutical composition can include a recombinant AAV vector disclosed herein. In certain embodiments, the pharmaceutical composition can include mRNA disclosed herein encoding an engineered meganuclease. In particular embodiments, the mRNA can be encapsulated within lipid nanoparticles.

In some embodiments of the method, the engineered meganuclease, or the nucleic acid encoding the engineered meganuclease, can be delivered to a target hepatic cell. The target hepatic cell can be a hepatocyte cell, such as a primary hepatocyte cell.

In some embodiments of the method, display of LDL receptors on the cell surface of hepatic cells in the subject is increased by the treatment when compared to the baseline LDL receptor level. Display of LDL receptors on the cell surface can increase about 5%, 10%, 20%, 30%, 40%, 50%, 60%, 70%, 80%, 90%, 95%, 100%, 150%, 250%, 500%, 1000%, or more, when compared to the baseline LDL receptor level.

In certain embodiments of the method, the total serum cholesterol level in the subject is reduced by the treatment. Total serum cholesterol levels can be reduced by: (a) at least about 5%, 10%, 20%, 30%, 40%, 50%, 60%, 70%, 80%, 90%, 95%, or up to 100%, or (b) by 5-15 mg/dL, 10-20 mg/dL, 10-30 mg/dL, 15-30 mg/dL, 20-30 mg/dL, 25-35 mg/dL, 25-40 mg/dL, 25-50 mg/dL, 40-60 mg/dL, 50-70 mg/dL, 60-80 mg/dL, or 70-100 mg/dL, when compared to the baseline total serum cholesterol level.

In certain embodiments, the serum LDL cholesterol level in the subject is reduced by the treatment. Serum LDL cholesterol levels can be reduced by: (a) at least about 5%, 10%, 20%, 30%, 40%, 50%, 60%, 70%, 80%, 90%, 95%, or up to 100%, or (b) 5-15 mg/dL, 10-20 mg/dL, 10-30 mg/dL, 15-30 mg/dL, 20-30 mg/dL, 25-35 mg/dL, 25-40 mg/dL, 25-50 mg/dL, 40-60 mg/dL, 50-70 mg/dL, or 60-80 mg/dL, when compared to the baseline serum LDL cholesterol level.

In particular embodiments of the methods, the first recognition sequence can comprise SEQ ID NO: 4. In some such embodiments, the engineered meganuclease can be any engineered meganuclease of the invention which recognizes and cleaves SEQ ID NO: 4. In particular embodiments, the engineered meganuclease can comprise the amino acid sequence of any one of SEQ ID NOs: 6-14.

In another aspect, the invention provides an engineered meganuclease described herein for use as a medicament. The invention further provides the use of an engineered meganuclease described herein as a medicament for treating a cholesterol-related disorder, such as hypercholesterolemia, including autosomal dominant FH, for reducing the activity or expression of PCSK9, or for reducing the symptoms associated with a cholesterol-related disorder. In particular embodiments, the invention provides the use of an engineered meganuclease described herein as a medicament for reducing the total cholesterol level and/or LDL cholesterol level in a subject.

In another aspect, the invention provides an isolated polynucleotide for use as a medicament, wherein the isolated polynucleotide comprises a nucleic acid sequence encoding an engineered meganuclease disclosed herein. The invention further provides the use of an isolated polynucleotide as a medicament for treating a cholesterol-related disorder, such as hypercholesterolemia, including autosomal dominant FH, for reducing the activity or expression of PCSK9, or for reducing the symptoms associated with a cholesterol-related disorder, wherein the isolated polynucleotide encodes an engineered meganuclease disclosed herein. In particular embodiments, the invention provides the use of an isolated polynucleotide encoding an engineered meganuclease described herein as a medicament for reducing the total cholesterol level and/or LDL cholesterol level in a subject.

In another aspect, the invention provides a recombinant AAV vector for use as a medicament, wherein the recombinant AAV vector comprises an isolated polynucleotide, and wherein the isolated polynucleotide comprises a nucleic acid sequence encoding an engineered meganuclease disclosed herein. The invention further provides the use of a recombinant AAV vector as a medicament for treating a cholesterol-related disorder, such as hypercholesterolemia, including autosomal dominant FH, for reducing the activity or expression of PCSK9, or for reducing the symptoms associated with a cholesterol-related disorder, wherein the recombinant AAV vector comprises an isolated polynucleotide, and wherein the isolated polynucleotide comprises a nucleic acid sequence encoding an engineered meganuclease disclosed herein. The invention further provides the use of a recombinant AAV vector as a medicament for reducing the total cholesterol level and/or LDL cholesterol level in a subject, wherein the recombinant AAV vector comprises an isolated polynucleotide, and wherein the isolated polynucleotide comprises a nucleic acid sequence encoding an engineered meganuclease disclosed herein.

The foregoing and other aspects and embodiments of the present invention can be more fully understood by reference to the following detailed description and claims. Certain features of the invention, which are, for clarity, described in the context of separate embodiments, may also be provided in combination in a single embodiment. All combinations of the embodiments are specifically embraced by the present invention and are disclosed herein just as if each and every combination was individually and explicitly disclosed. Conversely, various features of the invention, which are, for brevity, described in the context of a single embodiment, may also be provided separately or in any suitable sub-combination. All sub-combinations of features listed in the embodiments are also specifically embraced by the present invention and are disclosed herein just as if each and every such sub-combination was individually and explicitly disclosed herein. Embodiments of each aspect of the present invention disclosed herein apply to each other aspect of the invention mutatis mutandis.

BRIEF DESCRIPTION OF THE FIGURES

FIG. 1. The engineered meganuclease recognition sequence in the human PCSK9 gene. The recognition sequence targeted by an engineered meganuclease of the invention comprises two recognition half-sites. Each recognition half-site comprises 9 base pairs, and the two half-sites are separated by a 4 base pair central sequence. The PCS 7-8 recognition sequence (SEQ ID NO: 4) comprises two recognition half-sites referred to as PCS7 and PCS8.

FIGS. 4A-4C show meganucleases targeting the PCS 7-8 recognition sequence. FIG. 4A shows PCS 7-8x.88 and PCS 7-8x.66. FIG. 4B shows PCS 7-8L.197, PCS 7-8L.204, PCS 7-8L.209, PCS 7-8L.261, PCS 7-8L.262, and PCS 7-8L.268. FIG. 4C shows PCS 7-8L.197 and PCS 7-8L.367.

FIG. 5A shows the PCS 7-8x.88 and PCS 7-8x.66 meganucleases targeting the PCS 7-8 recognition sequence. FIG. 5B shows the PCS 7-8x.88 and PCS 7-8L.197 meganucleases targeting the PCS 7-8 recognition sequence. FIG. 5C shows the PCS 7-8L.367 meganuclease targeting the PCS 7-8 recognition sequence.

FIG. 8A shows LDL levels measured over time in each subject.

FIG. 8B shows total cholesterol, HDL, LDL, and triglyceride levels in subject RA1866.

FIG. 8C shows total cholesterol, HDL, LDL, and triglyceride levels in subject RA1857.

FIG. 8D shows total cholesterol, HDL, LDL, and triglyceride levels in subject RA1829.

FIG. 8E shows total cholesterol, HDL, LDL, and triglyceride levels in subject RA2334.

FIG. 10. Frequency of insertions and deletions (indels) observed at the PCS 7-8 recognition sequence in hepatic cells in vivo. Liver biopsies were taken at day 17 after administration of the AAV8.TBG.PI.PCS7-8x.88.WPRE.bGH vector, and examined for the presence of indels at the PCS 7-8 recognition sequence. Indels were detected by the use of PCR primers flanking the recognition sequence, amplification of the intervening region of the genome, and sequencing of the resulting PCR products.

FIG. 11A shows a mock treatment of biopsied cells from another subject M11657 which was performed as a control without oligo probes. FIG. 11B shows biopsy samples from subject RA1866. FIG. 11C shows biopsy samples from subject RA1857. FIG. 11D shows biopsy samples from subject RA1829.

FIG. 11E shows biopsy samples from subject RA2334.

FIG. 15A shows biopsy samples from subject RA2125. FIG. 15B shows biopsy samples from subject RA2343.

BRIEF DESCRIPTION OF THE SEQUENCES

Figure 2:
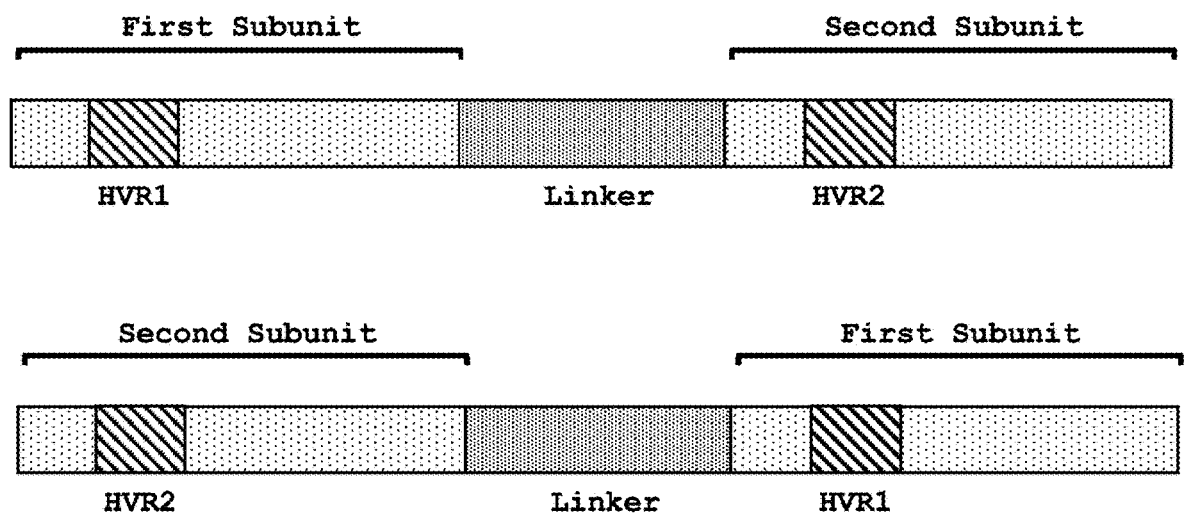
FIG. 2. The engineered meganucleases of the invention comprise two subunits, wherein the first subunit comprising the HVR1 region binds to a first recognition half-site (e.g., PCS7) and the second subunit comprising the HVR2 region binds to a second recognition half-site (e.g., PCS8). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

SEQ ID NO: 1 sets forth the amino acid sequence of the wild-type I-CreI meganuclease.

SEQ ID NO: 2 sets forth the amino acid sequence of LAGLIDADG.

SEQ ID NO: 3 sets forth the nucleic acid sequence of the human PCSK9 gene.

SEQ ID NO: 4 sets forth the nucleic acid sequence of the PCS 7-8 recognition sequence (sense).

SEQ ID NO: 5 sets forth the nucleic acid sequence of the PCS 7-8 recognition sequence (antisense).

SEQ ID NO: 6 sets forth the amino acid sequence of the PCS 7-8L.197 meganuclease.

SEQ ID NO: 7 sets forth the amino acid sequence of the PCS 7-8x.88 meganuclease.

SEQ ID NO: 8 sets forth the amino acid sequence of the PCS 7-8L.367 meganuclease.

SEQ ID NO: 9 sets forth the amino acid sequence of the PCS 7-8L.204 meganuclease.

SEQ ID NO: 10 sets forth the amino acid sequence of the PCS 7-8L.209 meganuclease.

SEQ ID NO: 11 sets forth the amino acid sequence of the PCS 7-8L.261 meganuclease.

SEQ ID NO: 12 sets forth the amino acid sequence of the PCS 7-8L.262 meganuclease.

SEQ ID NO: 13 sets forth the amino acid sequence of the PCS 7-8L.268 meganuclease.

SEQ ID NO: 14 sets forth the amino acid sequence of the PCS 7-8x.66 meganuclease.

SEQ ID NO: 15 sets forth the amino acid sequence of the PCS 7-8L.197 meganuclease PCS7-binding subunit.

SEQ ID NO: 16 sets forth the amino acid sequence of the PCS 7-8x.88 meganuclease PCS7-binding subunit.

SEQ ID NO: 17 sets forth the amino acid sequence of the PCS 7-8L.367 meganuclease PCS7-binding subunit.

SEQ ID NO: 18 sets forth the amino acid sequence of the PCS 7-8L.204 meganuclease PCS7-binding subunit.

SEQ ID NO: 19 sets forth the amino acid sequence of the PCS 7-8L.209 meganuclease PCS7-binding subunit.

SEQ ID NO: 20 sets forth the amino acid sequence of the PCS 7-8L.261 meganuclease PCS7-binding subunit.

SEQ ID NO: 21 sets forth the amino acid sequence of the PCS 7-8L.262 meganuclease PCS7-binding subunit.

SEQ ID NO: 22 sets forth the amino acid sequence of the PCS 7-8L.268 meganuclease PCS7-binding subunit.

SEQ ID NO: 23 sets forth the amino acid sequence of the PCS 7-8x.66 meganuclease PCS7-binding subunit.

SEQ ID NO: 24 sets forth the amino acid sequence of the PCS 7-8L.197 meganuclease PCS8-binding subunit.

SEQ ID NO: 25 sets forth the amino acid sequence of the PCS 7-8x.88 meganuclease PCS8-binding subunit.

SEQ ID NO: 26 sets forth the amino acid sequence of the PCS 7-8L.367 meganuclease PCS8-binding subunit.

SEQ ID NO: 27 sets forth the amino acid sequence of the PCS 7-8L.204 meganuclease PCS8-binding subunit.

SEQ ID NO: 28 sets forth the amino acid sequence of the PCS 7-8L.209 meganuclease PCS8-binding subunit.

SEQ ID NO: 29 sets forth the amino acid sequence of the PCS 7-8L.261 meganuclease PCS8-binding subunit.

SEQ ID NO: 30 sets forth the amino acid sequence of the PCS 7-8L.262 meganuclease PCS8-binding subunit.

SEQ ID NO: 31 sets forth the amino acid sequence of the PCS 7-8L.268 meganuclease PCS8-binding subunit.

SEQ ID NO: 32 sets forth the amino acid sequence of the PCS 7-8x.66 meganuclease PCS8-binding subunit.

SEQ ID NO: 33 sets forth the nucleic acid sequence of an indel observed in vivo following treatment with PCS 7-8x.88.

SEQ ID NO: 34 sets forth the nucleic acid sequence of an indel observed in vivo following treatment with PCS 7-8x.88.

SEQ ID NO: 35 sets forth the nucleic acid sequence of an indel observed in vivo following treatment with PCS 7-8x.88.

SEQ ID NO: 36 sets forth the nucleic acid sequence of an indel observed in vivo following treatment with PCS 7-8x.88.

SEQ ID NO: 37 sets forth the nucleic acid sequence of an indel observed in vivo following treatment with PCS 7-8x.88.

SEQ ID NO: 38 sets forth the nucleic acid sequence of an indel observed in vivo following treatment with PCS 7-8x.88.

SEQ ID NO: 39 sets forth the nucleic acid sequence of an indel observed in vivo following treatment with PCS 7-8x.88.

SEQ ID NO: 40 sets forth the nucleic acid sequence of an indel observed in vivo following treatment with PCS 7-8x.88.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes which cleave a phosphodiester bond within a polynucleotide chain.

As used herein, the term "meganuclease" refers to an endonuclease that binds double-stranded DNA at a recognition sequence that is greater than 12 base pairs. Preferably, the recognition sequence for a meganuclease of the invention is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859). A meganuclease as used herein binds to double-stranded DNA as a heterodimer. A meganuclease may also be a "single-chain meganuclease" in which a pair of DNA-binding domains are joined into a single polypeptide using a peptide linker. The term "homing endonuclease" is synonymous with the term "meganuclease." Meganucleases of the invention are substantially non-toxic when expressed in cells without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251 and 9,434,931. In some embodiments, a linker may have an amino acid sequence comprising residues 154-195 of any one of SEQ ID NOs: 6-14.

As used herein, with respect to a protein, the term "recombinant" or "engineered" means having an altered amino acid sequence as a result of the application of genetic engineering techniques to nucleic acids which encode the protein, and cells or organisms which express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refer to a DNA sequence that is bound and cleaved by an endonuclease. In the case of a meganuclease, a recognition sequence comprises a pair of inverted, 9 base pair "half sites" which are separated by four basepairs. In the case of a single-chain meganuclease, the N-terminal domain of the protein contacts a first half-site and the C-terminal domain of the protein contacts a second half-site. Cleavage by a meganuclease produces four base pair 3' "overhangs". "Overhangs", or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 base pair recognition sequence.

As used herein, the term "target site" or "target sequence" refers to a region of the chromosomal DNA of a cell comprising a recognition sequence for a nuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, $K_d$. As used herein, a nuclease has "altered" binding affinity if the $K_d$ of the nuclease for a reference recognition sequence is increased or decreased by a statistically significant ($p<0.05$) amount relative to a reference nuclease.

As used herein, the term "specificity" means the ability of a meganuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific meganuclease is capable of cleaving only one or a very few recognition sequences. Specificity can be determined by any method known in the art. As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2x, or 2x-10x) relative to a reference meganuclease.

As used herein, the term "homologous recombination" or "HR" refers to the natural, cellular process in which a double-stranded DNA-break is repaired using a homologous DNA sequence as the repair template (see, e.g., Cahill et al. (2006), *Front. Biosci.* 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g., Cahill et al. (2006), *Front. Biosci.* 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered meganucleases can be used to effectively knock-out a gene in a population of cells.

As used herein, the term "reduced" refers to any reduction in the symptoms or severity of a cholesterol-related disease, or any reduction in protein expression or activity of PCSK9. In any situation, such a reduction may be up to 5%, 10%, 20%, 30%, 40%, 50%, 60%, 70%, 80%, 90%, 95%, or up to 100%. Accordingly, the term "reduced" encompasses both a partial reduction and a complete reduction of a disease state, protein expression, protein activity, or PCSK9 binding to an LDL receptor.

As used herein, the term "increased" refers to any increase in the display of LDL receptor on the surface of a cell. Such an increase may be up to 5%, 10%, 20%, 30%, 40%, 50%, 60%, 70%, 80%, 90%, 95%, 100%, 150%, 250%, 500%, 1000%, or more. Any method can be used to measure an increase in the surface display of the LDL receptor.

As used herein, the term "hypercholesterolemia" refers to a condition in which cholesterol levels are elevated above a desired level. In certain embodiments, the LDL-cholesterol level is elevated above the desired level. In certain embodiments, the serum LDL-cholesterol levels are elevated above the desired level. As used herein, the term "familial hypercholesterolemia" or "FH" refers to an genetic disorder characterized by elevated levels of low density lipoprotein (LDL)-associated cholesterol in the plasma. Compared with LDL cholesterol levels in normal patients (e.g., <130 mg/dL), levels in heterozygous and homozygous FH patients often rise to 350-550 mg/dL and to >600 mg/dL, respectively. Elevation in LDL cholesterol at these levels in patients or subjects with FH leads to cholesterol deposition within tissues and an increased risk for cardiovascular disease at a young age.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=-11; gap extension penalty=-1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule which is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 6-14. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 6-14. In certain embodiments, variable residues within a hypervariable region also correspond to one or more of positions 48, 50, 71, and 73 of SEQ ID NO: 8. In other embodiments, variable residues within a hypervariable region correspond to one or more of positions 215, 217, 219, 221, 223, 224, 229, 231, 233, 235, 237, 259, 261, 266, and 268 of any one of SEQ ID NOs: 6-14. In further embodiments, a variable residue within a hypervariable region may also correspond to residue 258 of SEQ ID NO: 12.

The terms "recombinant DNA construct," "recombinant construct," "expression cassette," "expression construct," "chimeric construct," "construct," and "recombinant DNA fragment" are used interchangeably herein and are nucleic acid fragments. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA which comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the terms "treatment" or "treating a subject" refers to the administration of a engineered meganuclease of the invention, or a nucleic acid encoding an engineered meganuclease of the invention, to a subject having a disease characterized by increased levels of fat and/or cholesterol circulating in the blood, such as a cholesterol-related disorder. For example, the subject can have cardiovascular disease, hypercholesterolemia, including autosomal dominant FH, hypertriglyceridemia, and other cholesterol-related disorders. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. Accordingly, treating the disease and/or disorder refers to altering (e.g., slowing) the progression of a disease and/or disorder, reducing total cholesterol and/or low-density lipoprotein (LDL) cholesterol level, improving Crigler-Najjar syndrome, restoring hepcidin and/or hemochromatosis type 2 function to regulate iron uptake, restoring bile acid metabolism, reducing coronary heart disease risk for familial hypercholesterolemia, and preventing hyperkeratotic plaques and corneal clouding which may heal hyperkeratotic plaques on the hands and/or feet. In some aspects, an engineered meganuclease of the invention, or a nucleic acid encoding the same, is administered during treatment in the form of a pharmaceutical composition of the invention.

As used herein, a "cholesterol-related disorder" includes any one or more of the following: hypercholesterolemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using an engineered meganuclease disclosed herein, either alone, or in combination with one or more other agents, include metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apolipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. The engineered meganucleases disclosed herein can also be useful in preventing or treating atherosclerotic diseases, such as, for example, coronary heart disease, coronary artery disease, peripheral arterial disease, stroke (ischaemic and hemorrhagic), angina pectoris, or cerebrovascular disease and acute coronary syndrome, myocardial infarction.

The term "proprotein convertase subtilisin kexin type 9" or "PCSK9" refers to a polypeptide encoded by a PCSK9 gene, such as the human PCSK9 gene set forth in SEQ ID NO: 3 (and variants thereof which encode active PCSK9 polypeptides), or fragments thereof, as well as related polypeptides, which include, but are not limited to, allelic variants, splice variants, derivative variants, substitution variants, deletion variants, and/or insertion variants including the addition of an N-terminal methionine, fusion polypeptides, and interspecies homologs. In certain embodiments, a PCSK9 polypeptide includes terminal residues, such as, but not limited to, leader sequence residues, targeting residues, amino terminal methionine residues, lysine residues, tag residues and/or fusion protein residues. "PCSK9" has also been referred to as FH3, NARC1, HCHOLA3, proprotein convertase subtilisin/kexin type 9, and neural apoptosis regulated convertase 1. The PCSK9 gene encodes a proprotein convertase protein that belongs to the proteinase K subfamily of the secretory subtilase family. The term "PCSK9" denotes both the proprotein and the product generated following autocatalysis of the proprotein. When only the autocatalyzed product is being referred, the protein can be referred to as the "mature," "cleaved", "processed" or "active" PCSK9. When only the inactive form is being referred to, the protein can be referred to as the "inactive", "pro-form", or "unprocessed" form of PCSK9. The term PCSK9 as used herein also includes naturally occurring alleles, such as the mutations D374Y, S127R and F216L. The term PCSK9 also encompasses PCSK9 molecules incorporating post-translational modifications of the PCSK9 amino acid sequence, such as PCSK9 sequences that have been glycosylated, PEGylated, PCSK9 sequences from which its signal sequence has been cleaved, PCSK9 sequence from which its pro domain has been cleaved from the catalytic domain but not separated from the catalytic domain The term "PCSK9 activity" includes any biological effect of PCSK9. In certain embodiments, PCSK9 activity includes the ability of PCSK9 to interact or bind to a substrate or receptor. In some embodiments, PCSK9 activity is represented by the ability of PCSK9 to bind to a LDL receptor (LDLR). In some embodiments, PCSK9 binds to and catalyzes a reaction involving LDLR. For example, PCSK9 activity includes the ability of PCSK9 to alter (e.g., reduce) the availability of LDLR. Thus, in some embodiments, PCSK9 activity includes the ability of PCSK9 to increase the amount of LDL in a subject. In particular embodiments, PCSK9 activity includes the ability of PCSK9 to decrease the amount of LDLR that is available to bind to LDL. Accordingly, by decreasing PCSK9 activity, the amount of LDLR that is displayed on the surface and able to find LDL in a subject is increased. In some embodiments, "PCSK9 activity" includes any biological activity resulting from PCSK9 signaling. Exemplary activities include, but are not limited to, PCSK9 binding to LDLR, PCSK9 enzyme activity that cleaves LDLR or other proteins, PCSK9 binding to proteins other than LDLR that facilitate PCSK9 action, PCSK9 altering APOB secretion (Sun et al. (2005), *Human Molecular Genetics* 14: 1161-1169, and Ouguerram et al. (2004), *Arterioscler thromb Vasc Biol.* 24: 1448-1453), the role of PCSK9 in liver regeneration and neuronal cell differentiation (Seidah et al., *PNAS* 100: 928-933, 2003), and the role of PCSK9 in hepatic glucose metabolism (Costet et al. (2006), *J. Biol. Chem.* 281(10):6211-18).

The term "effective amount" or "therapeutically effective amount" refers to an amount sufficient to effect beneficial or desirable biological and/or clinical results. The therapeutically effective amount will vary depending on the meganuclease formulation or composition, the disease and its severity and the age, weight, physical condition and responsiveness of the subject to be treated. In specific embodiments, an effective amount of the engineered meganuclease or pharmaceutical compositions disclosed herein treating or preventing hypercholesterolemia or other cholesterol-related disorder and/or at least one symptom of dyslipidemia, atherosclerosis, cardiovascular disease (CVD), or coronary heart disease by reducing the level of total cholesterol or LDL cholesterol (i.e., serum LDL) in a subject.

The term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values 0 and 2 if the variable is inherently continuous.

2.1 Principle of the Invention

The present invention is based, in part, on the hypothesis that engineered meganucleases can be used to reduce the expression of PCSK9 and thereby increase the removal of fat and/or cholesterol from the blood. Decreasing expression of PCSK9 can increase the display of LDL receptors on the cell surface and thereby increase the removal of lipids from the bloodstream. Thus, by delivering an engineered meganuclease specific for a recognition sequence in the PCSK9 gene, the expression of PCSK9 can be reduced which can subsequently decrease the total cholesterol (e.g., serum LDL) in the blood of a subject. Accordingly, the methods and compositions disclosed herein find particular use in treating cholesterol-related disorders caused by an increase in PCSK9 expression compared to the level of PCSK9 expression in a proper control.

Thus, the present invention encompasses engineered meganucleases which recognize and cleave a recognition sequence within the PCSK9 gene. The present invention also encompasses methods for using such engineered meganucleases in a pharmaceutical composition and in methods for treating cholesterol-related disorders, such as hypercholesterolemia. Further, the invention encompasses pharmaceutical compositions comprising engineered meganuclease proteins, or nucleic acids encoding engineered meganucleases, and the use of such compositions for the treatment of cholesterol-related disorders, such as hypercholesterolemia.

2.2 Meganucleases for Recognizing and Cleaving Recognition Sequences within the PCSK9 Gene Site-specific nucleases can be used to introduce a break in the PCSK9 gene, and repair of such a break can result in permanent modification of the gene via NHEJ such that an active PCSK9 gene is no longer expressed. Thus, in one embodiment, the invention can be practiced using engineered recombinant meganucleases.

In preferred embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some examples, engineered meganucleases of the invention have been engineered to recognize and cleave the PCS 7-8 recognition sequence (SEQ ID NO: 4). The PCS 7-8 recognition sequence is positioned within the PCSK9 gene set forth in SEQ ID NO: 3. Such engineered meganucleases are collectively referred to herein as "PCS 7-8 meganucleases." Exemplary PCS 7-8 meganucleases are provided in SEQ ID NOs: 6-14.

Engineered meganucleases of the invention comprise a first subunit, comprising a first hypervariable (HVR1) region, and a second subunit, comprising a second hypervariable (HVR2) region. Further, the first subunit binds to a first recognition half-site in the recognition sequence (e.g., the PCS7 half-site), and the second subunit binds to a second recognition half-site in the recognition sequence (e.g., the PCS7 half-site). In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary PCS 7-8 meganucleases of the invention are provided in Table 1.

TABLE 1

Exemplary engineered meganucleases engineered to recognize and cleave the PCS 7-8 recognition sequence (SEQ ID NO: 4)

| Meganuclease | AA SEQ ID | PCS7 Subunit Residues | PCS7 Subunit SEQ ID | *PCS7 Subunit % | PCS8 Subunit Residues | PCS8 Subunit SEQ ID | *PCS8 Subunit % |
|---|---|---|---|---|---|---|---|
| PCS 7-8L.197 | 6 | 7-153 | 15 | 100 | 198-344 | 24 | 100 |
| PCS 7-8x.88 | 7 | 7-153 | 16 | 98.64 | 198-344 | 25 | 99.32 |
| PCS 7-8L.367 | 8 | 7-153 | 17 | 95.92 | 198-344 | 26 | 100 |
| PCS 7-8L.204 | 9 | 7-153 | 18 | 98.64 | 198-344 | 27 | 99.32 |
| PCS 7-8L.209 | 10 | 7-153 | 19 | 99.32 | 198-344 | 28 | 100 |
| PCS 7-8L.261 | 11 | 7-153 | 20 | 98.64 | 198-344 | 29 | 98.64 |
| PCS 7-8L.262 | 12 | 7-153 | 21 | 98.64 | 198-344 | 30 | 98.64 |

TABLE 1-continued

Exemplary engineered meganucleases engineered to recognize and cleave the PCS 7-8 recognition sequence (SEQ ID NO: 4)

| Meganuclease | AA SEQ ID | PCS7 Subunit Residues | PCS7 Subunit SEQ ID | *PCS7 Subunit % | PCS8 Subunit Residues | PCS8 Subunit SEQ ID | *PCS8 Subunit % |
|---|---|---|---|---|---|---|---|
| PCS 7-8L.268 | 13 | 7-153 | 22 | 99.32 | 198-344 | 31 | 100 |
| PCS 7-8x.66 | 14 | 7-153 | 23 | 93.2 | 198-344 | 32 | 99.32 |

*"PCS7 Subunit %" and "PCS8 Subunit %" represent the amino acid sequence identity between the PCS7-binding and PCS8-binding subunit regions of each meganuclease and the PCS7-binding and PCS8-binding subunit regions, respectively, of the PCS 7-8L.197 meganuclease.

2.3 Methods for Delivering and Expressing Endonucleases

Disclosed herein are methods for treating hypercholesterolemia and cardiovascular diseases in a subject. Likewise, methods are provided for reducing the symptoms of hypercholesterolemia and cardiovascular diseases in a subject comprising administering a pharmaceutical composition comprising a pharmaceutically acceptable carrier and an engineered meganuclease disclosed herein (or a nucleic acid encoding the engineered meganuclease). Further provided are methods for decreasing the expression and/or activity of PCSK9 in a subject comprising delivering an engineered meganuclease disclosed herein to a target cell in the subject. In the methods of the invention an engineered meganuclease disclosed herein can be delivered to and/or expressed from DNA/RNA in target cells.

Engineered meganucleases disclosed herein can be delivered into a cell in the form of protein or, preferably, as a nucleic acid encoding the engineered meganuclease. Such nucleic acid can be DNA (e.g., circular or linearized plasmid DNA or PCR products) or RNA (e.g., mRNA). For embodiments in which the engineered meganuclease coding sequence is delivered in DNA form, it should be operably linked to a promoter to facilitate transcription of the nuclease gene. Mammalian promoters suitable for the invention include constitutive promoters such as the cytomegalovirus early (CMV) promoter (Thomsen et al. (1984), *Proc Natl Acad Sci USA*. 81(3):659-63) or the SV40 early promoter (Benoist and Chambon (1981), *Nature* 290(5804):304-10) as well as inducible promoters such as the tetracycline-inducible promoter (Dingermann et al. (1992), *Mol Cell Biol*. 12(9):4038-45). An engineered meganuclease of the invention can also be operably linked to a synthetic promoter. Synthetic promoters can include, without limitation, the JeT promoter (WO 2002/012514). In specific embodiments, a nucleic acid sequence encoding an engineered meganuclease as disclosed herein can be operably linked to a liver-specific promoter or hepatocyte-specific promoter. Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In specific embodiments, a nucleic acid sequence encoding at least one engineered meganuclease is delivered on a recombinant DNA construct or expression cassette. For example, the recombinant DNA construct can comprise an expression cassette (i.e., "cassette") comprising a promoter and a nucleic acid sequence encoding an engineered meganuclease described herein. In other embodiments, the recombinant DNA construct comprises two or more cassettes, wherein each cassette comprises a promoter and a nucleic acid sequence encoding an engineered meganuclease described herein. In particular embodiments, the recombinant DNA construct can comprise two cassettes, three cassettes, four cassettes, or more.

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell.

In some embodiments, mRNA encoding an engineered meganuclease is delivered to a cell because this reduces the likelihood that the gene encoding the engineered meganuclease will integrate into the genome of the cell. Such mRNA encoding an engineered meganuclease can be produced using methods known in the art such as in vitro transcription. In some embodiments, the mRNA is capped using 7-methylguanosine, ARCA, CleanCap, or enzymatically capped using vaccinia capping enzyme or similar. In some embodiments, the mRNA may be polyadenylated. The mRNA may contain various 5' and 3' untranslated sequence elements to enhance expression the encoded engineered meganuclease and/or stability of the mRNA itself. The mRNA may contain nucleoside analogs such as pseudouridine, 5-methylcytidine, N6-methyladenosine, 5-methyluridine, or 2-thiouridine.

In particular embodiments, an mRNA encoding an engineered nuclease of the invention can be a polycistronic mRNA encoding two or more nucleases which are simultaneously expressed in a cell. In some embodiments, a polycistronic mRNA can encode two or more meganucleases described herein and at least one additional protein which induces a therapeutically beneficial effect in the cell. A polycistronic mRNA of the invention can comprise any element known in the art to allow for the translation of two or more genes from the same mRNA molecule including, but not limited to, an IRES element, a T2A element, a P2A element, an E2A element, and an F2A element. In particular embodiments, the polycistronic mRNA is a bicistronic mRNA encoding two meganucleases described herein, a tricistronic mRNA encoding three meganucleases described herein.

In another particular embodiment, a nucleic acid encoding an endonuclease of the invention can be delivered to a target cell as a single-stranded DNA template. The single-stranded DNA can further comprise a 5' and/or a 3' AAV inverted terminal repeat (ITR) upstream and/or downstream of the sequence encoding the engineered meganuclease. In other embodiments, the single-stranded DNA can further comprise a 5' and/or a 3' homology arm upstream and/or downstream of the sequence encoding the engineered meganuclease.

In another particular embodiment, genes encoding an endonuclease of the invention can be delivered to a target cell as a linearized DNA template. In some examples, a plasmid DNA encoding an endonuclease can be digested by one or more restriction enzymes such that the circular plasmid DNA is linearized prior to delivery to the target cell.

Purified nuclease proteins can be delivered to cells to cleave genomic DNA by a variety of different mechanisms known in the art, including those further detailed herein below.

The target tissue(s) for delivery of engineered meganucleases of the invention include, without limitation, cells of the liver, such as a hepatocyte cell or preferably a primary hepatocyte, more preferably a human hepatocyte or a human primary hepatocyte, a HepG2.2.15 or a HepG2-hNTCP cell. In particular embodiments the cells are cells of a primate hepatocyte, such as a primate primary hepatocyte. As discussed, meganucleases of the invention can be delivered as purified protein or as RNA or DNA encoding the meganuclease. In one embodiment, meganuclease proteins, or mRNA, or DNA vectors encoding endonucleases, are supplied to target cells (e.g., cells in the liver) via injection directly to the target tissue. Alternatively, meganuclease protein, mRNA, or DNA can be delivered systemically via the circulatory system.

In some embodiments, endonuclease proteins, or DNA/mRNA encoding meganucleases, are formulated for systemic administration, or administration to target tissues, in a pharmaceutically acceptable carrier in accordance with known techniques. See, e.g., Remington, *The Science And Practice of Pharmacy* (21$^{st}$ ed. 2005). In the manufacture of a pharmaceutical formulation according to the invention, proteins/RNA/mRNA are typically admixed with a pharmaceutically acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation.

In some embodiments, meganuclease proteins, or DNA/mRNA encoding the meganuclease, are coupled to a cell penetrating peptide or targeting ligand to facilitate cellular uptake. Examples of cell penetrating peptides known in the art include poly-arginine (Jearawiriyapaisarn et al. (2008), *Mol Ther.* 16:1624-9), TAT peptide from the HIV virus (Hudecz et al. (2005), *Med. Res. Rev.* 25: 679-736), MPG (Simeoni et al. (2003), *Nucleic Acids Res.* 31:2717-2724), Pep-1 (Deshayes et al. (2004), *Biochemistry* 43: 7698-7706, and HSV-1 VP-22 (Deshayes et al. (2005), *Cell Mol Life Sci.* 62:1839-49. In an alternative embodiment, meganuclease proteins, or DNA/mRNA encoding meganucleases, are coupled covalently or non-covalently to an antibody that recognizes a specific cell-surface receptor expressed on target cells such that the meganuclease protein/DNA/mRNA binds to and is internalized by the target cells. Alternatively, meganuclease protein/DNA/mRNA can be coupled covalently or non-covalently to the natural ligand (or a portion of the natural ligand) for such a cell-surface receptor. (McCall et al. (2014), *Tissue Barriers* 2(4):e944449; Dinda et al. (2013), *Curr Pharm Biotechnol.* 14:1264-74; Kang et al. (2014), *Curr Pharm Biotechnol.* 15(3):220-30; Qian et al. (2014), *Expert Opin Drug Metab Toxicol.* 10(11):1491-508).

In some embodiments, meganuclease proteins, or DNA/mRNA encoding meganucleases, are encapsulated within biodegradable hydrogels for injection or implantation within the desired region of the liver. Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008), *Trans Am Ophthalmol Soc.* 106:206-214).

In some embodiments, meganuclease proteins, or DNA/mRNA encoding meganucleases, are coupled covalently or, preferably, non-covalently to a nanoparticle or encapsulated within such a nanoparticle using methods known in the art (Sharma et al. (2014), *Biomed Res Int.* 2014:327950). A nanoparticle is a nanoscale delivery system whose length scale is <1 µm, preferably <100 nm. Such nanoparticles may be designed using a core composed of metal, lipid, polymer, or biological macromolecule, and multiple copies of the meganuclease proteins, mRNA, or DNA can be attached to or encapsulated with the nanoparticle core. This increases the copy number of the protein/mRNA/DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012), *Biomaterials* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins or DNA/mRNA encoding the meganucleases are encapsulated within liposomes or complexed using cationic lipids (see, e.g., LIPOFECTAMINE transfection reagent, Life Technologies Corp., Carlsbad, Calif.; Zuris et al. (2015), *Nat Biotechnol* 33: 73-80; Mishra et al. (2011), *J Drug Deliv.* 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011), *Ther Deliv* 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding engineered meganucleases, are combined with amphiphilic molecules that self-assemble into micelles (Tong et al. (2007), *J Gene Med* 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015), *Nanoscale* 7(9): 3845-56; Cheng et al. (2008), *J Pharm Sci* 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, genes encoding an meganuclease are delivered using a viral vector. Such vectors are known in the art and include retroviral vectors, lentiviral vectors, adenoviral vectors, and adeno-associated virus (AAV) vectors (reviewed in Vannucci et al. (2013), *New Microbiol* 36:1-22). In some embodiments, the viral vectors are injected directly into target tissues (e.g., liver tissue). In alternative embodiments, the viral vectors are delivered systemically via the circulatory system. It is known in the art that different AAV vectors tend to localize to different tissues. In liver target tissues, effective transduction of hepatocytes has been shown, for example, with AAV serotypes 2, 8, and 9 (Sands (2011), *Methods Mol Biol* 807:141-157; International Application Publication No. WO 2003/052051). AAV vectors can also be self-complementary such that they do not require second-strand DNA synthesis in the host cell (McCarty et al. (2001), *Gene Ther* 8:1248-54).

In one embodiment, a viral vector used for endonuclease gene delivery is a self-limiting viral vector. A self-limiting viral vector can have limited persistence time in a cell or organism due to the presence of a recognition sequence for an engineered meganuclease within the vector. Thus, a self-limiting viral vector can be engineered to provide coding for a promoter, an endonuclease described herein, and an endonuclease recognition site within the ITRs. The self-limiting viral vector delivers the endonuclease gene to a cell, tissue, or organism, such that the endonuclease is expressed and able to cut the genome of the cell at an endogenous recognition sequence within the genome. The delivered endonuclease will also find its target site within the self-limiting viral vector itself, and cut the vector at this target site. Once cut, the 5' and 3' ends of the viral genome will be exposed and degraded by exonucleases, thus killing the virus and ceasing production of the endonuclease.

If the endonuclease genes are delivered in DNA form (e.g., plasmid) and/or via a viral vector (e.g., AAV) may be operably linked to a promoter. In some embodiments, this can be a viral promoter such as endogenous promoters from the viral vector (e.g., the LTR of a lentiviral vector) or the well-known cytomegalovirus- or SV40 virus-early promoters. In a preferred embodiment, meganuclease genes are operably linked to a promoter that drives gene expression preferentially in the target cells. Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In particular embodiments, the viral vector comprises a cassette comprising a promoter and a nucleic acid sequence encoding an engineered meganuclease described herein. The viral vector could also comprise two or more cassettes, wherein each cassette comprises a promoter and a nucleic acid sequence encoding an engineered meganuclease described herein. In some embodiments, the viral vector comprises one cassette comprising a promoter and a polycistronic nucleic acid sequence, wherein the promoter drives expression of the polycistronic nucleic acid sequence to generate a polycistronic mRNA, such as polycistronic mRNA encoding an engineered meganuclease, described herein in a target cell.

Methods and compositions are provided for delivering a meganuclease disclosed herein to the liver of a subject having a cholesterol-related disorder, such as hypercholesterolemia, including autosomal dominant FH. In one embodiment, native hepatocytes which have been removed from the mammal can be transduced with a vector which encodes the engineered meganuclease. Alternatively, native hepatocytes of the subject can be transduced ex vivo with an adenoviral vector which encodes the engineered meganuclease and/or a molecule that stimulates liver regeneration, such as a hepatotoxin. Preferably the hepatotoxin is uPA, and has been modified to inhibit its secretion from the hepatocyte once expressed by the viral vector. In another embodiment the vector encodes tPA, which can stimulate hepatocyte regeneration de novo. The transduced hepatocytes which have been removed from the mammal can then be returned to the mammal, where conditions are provided which are conducive to expression of the engineered meganuclease. Typically the transduced hepatocytes can be returned to the patient by infusion through the spleen or portal vasculature, and administration may be single or multiple over a period of 1 to 5 or more days.

In an in vivo aspect of the methods of the invention, a retroviral, pseudotype or adenoviral associated vector is constructed which encodes the engineered meganuclease and is administered to the subject. Administration of a vector encoding the engineered meganuclease can occur with administration of an adenoviral vector that encodes a secretion-impaired hepatotoxin, or encodes tPA, which stimulates hepatocyte regeneration without acting as a hepatotoxin.

Appropriate doses will depend, among other factors, on the liposomal formulation used, the specifics of any AAV vector chosen (e.g., serotype, etc.), on the route of administration, on the subject being treated (i.e., age, weight, sex, and general condition of the subject), and the mode of administration. Thus, the appropriate dosage may vary from patient to patient. An appropriate effective amount can be readily determined by one of skill in the art. Dosage treatment may be a single dose schedule or a multiple dose schedule. Moreover, the subject may be administered as many doses as appropriate. One of skill in the art can readily determine an appropriate number of doses. The dosage may need to be adjusted to take into consideration an alternative route of administration, or balance the therapeutic benefit against any side effects.

Delivery of the engineered meganucleases disclosed herein, or nucleic acids encoding the engineered meganucleases disclosed herein, to a subject can treat or reduce the severity of a cholesterol-related disorder, such as hypercholesterolemia, including autosomal dominant FH. In particular embodiments, delivery of an engineered meganuclease or nucleic acid encoding an engineered meganuclease disclosed herein to a subject can reduce at least one symptom of a cholesterol-related disorder, such as hypercholesterolemia, including autosomal dominant FH. In some embodiments, the engineered meganuclease or nucleic acid encoding the engineered meganuclease is delivered to a subject in an effective amount. The subject to which the engineered meganucleases disclosed herein or nucleic acid encoding the engineered meganucleases disclosed herein is delivered can be any mammal. In particular embodiments, the subject is a domesticated animal (e.g., cows, sheep, cats, dogs, and horses), primate (e.g., humans and non-human primates such as monkeys), rabbits, and rodents (e.g., mice and rats). In certain embodiments, the subject is a non-human primate or a human. In some embodiments, the subject has a cholesterol-related disorder. For example, the subject can have hypercholesterolemia, familial hypercholesterolemia, or autosomal dominant familial hypercholesterolemia. In particular embodiments, the subject has a total cholesterol level over 170 mg/dL or 200 mg/dL, such as 170-200 mg/dL or 200-250 mg/dL, 200-300 mg/dL, 200-350 mg/dL, 200-400 mg/dL, 200-450 mg/dL, 200-500 mg/dL, or 200-600 mg/dL. In some embodiments, the subject has an LDL cholesterol level over 110 mg/dL or over 130 mg/dL, such as 110-120 mg/dL, 110-130 mg/dL, 130-150 mg/dL, 130-180 mg/dL, 130-200 mg/dL, 130-250 mg/dL, 130-300 mg/dL, 130-350 mg/dL, 130-400 mg/dL, 130-450 mg/dL, 130-500 mg/dL, or 130-600 mg/dL.

In particular embodiments, delivery of the meganucleases disclosed herein or nucleic acid encoding the engineered meganucleases disclosed herein to a subject can reduce expression of PCSK9 and/or reduce PCSK9 activity. For example, expression or activity of PCSK9 can be reduced by at least about 5%, 10%, 20%, 30%, 40%, 50%, 60%, 70%, 80%, 90%, 95%, or up to 100%, when compared to a control cell or baseline PCSK9 activity. In some embodiments, the expression and/or activity of PCSK9 is reduced by about 5-10%, 5-20%, 10-30%, 20-40%, 30-50%, 40-60%, 50-70%, 60-80%, 70-90%, or 80-100% when compared to a control cell or baseline PCSK9 activity. PCSK9 activity can be measured by any means known in the art as disclosed elsewhere herein. As used herein, a control cell can be any appropriate control such as a cell from the subject prior to delivery of a pharmaceutical composition, engineered meganuclease, or nucleic acid encoding an engineered meganuclease disclosed herein. In specific embodiments, the control cell is a liver cell or primary hepatocyte of the subject that is not delivered a pharmaceutical composition, engineered meganuclease, or nucleic acid encoding an engineered meganuclease disclosed herein. As used herein, a "baseline" level (such as baseline level for PCSK9 expression or activity or total or LDL cholesterol level) in a subject refers to the level before an administration of a pharmaceutical composition described herein to the individual. In certain embodiments, the baseline may be a mean or average of two or more measurements obtained before administration of a pharmaceutical composition described herein.

In some embodiments, delivery of the meganucleases disclosed herein, or nucleic acids encoding the engineered meganucleases disclosed herein, to a target cell in a subject can increase the display of LDL receptors on the surface of the cell or increase the level of LDL receptors. The level of LDL receptors can be measured by methods known in the art, such as measuring the level of LDL receptor or apolipoprotein B (APOB) receptor in the liver of a subject. For example, display or level of LDL receptors can increase by at least about 5%, 10%, 20%, 30%, 40%, 50%, 60%, 70%, 80%, 90%, 95%, 100%, 150%, 250%, 500%, 1000%, or more, after delivery of the meganucleases disclosed herein, or nucleic acids encoding the engineered meganucleases disclosed herein, to a target cell, when compared to a control cell or baseline level of LDL receptors on the cell surface.

Delivery of a pharmaceutical composition, engineered meganuclease, or nucleic acid encoding an engineered meganuclease disclosed herein to a target cell in a subject can reduce the total cholesterol level in the subject, when compared to the total cholesterol level in the subject prior to delivery. For example, the total cholesterol level can be reduced by at least about 5%, 10%, 20%, 30%, 40%, 50%, 60%, 70%, 80%, 90%, 95%, or up to 100%, when compared to the subject prior to treatment. In particular embodiments, the total cholesterol level in the subject delivered a pharmaceutical composition disclosed herein maintains a decrease compared to the total cholesterol level prior to delivery of the pharmaceutical composition for at least two weeks, at least one month, at least two months, or three months after the final dosing.

In particular embodiments, the total cholesterol level is reduced by about 5 mg/dL, 10 mg/dL, 15 mg/dL, 20 mg/dL, 25 mg/dL, 30 mg/dL, 40 mg/dL, 50 mg/dL, 60 mg/dL, 70 mg/dL, 80 mg/dL, 90 mg/dL, 100 mg/dL, 110 mg/dL, 5-15 mg/dL, 10-20 mg/dL, 10-30 mg/dL, 15-30 mg/dL, 20-30 mg/dL, 25-35 mg/dL, 25-40 mg/dL, 25-50 mg/dL, 40-60 mg/dL, 50-70 mg/dL, 60-80 mg/dL, 70-100 mg/dL, or more when compared to the cholesterol level prior to delivery of a pharmaceutical composition disclosed herein to a subject. In particular embodiments, the subject has a baseline total cholesterol level of 140 mg/dL, 150 mg/dL, 160 mg/dL, 170 mg/dL, 175 mg/dL, 180 mg/dL, 185 mg/dL, 190 mg/dL, 195 mg/dL, 200 mg/dL, 205 mg/dL, 210 mg/dL, 215 mg/dL, 220 mg/dL, 225 mg/dL, 230 mg/dL, 235 mg/dL, 240 mg/dL, 250 mg/dL, 260 mg/dL, 270 mg/dL, 280 mg/dL, 290 mg/dL, 300 mg/dL, or more. In some embodiments, the total cholesterol level is the serum cholesterol level or the total body cholesterol level.

Delivery of a pharmaceutical composition, engineered meganuclease, or nucleic acid encoding an engineered meganuclease disclosed herein to a target cell in a subject can reduce the LDL cholesterol level in the subject, when compared to the LDL cholesterol level in the subject prior to delivery. For example, the LDL cholesterol level can be reduced by at least about 5%, 10%, 20%, 30%, 40%, 50%, 60%, 70%, 80%, 90%, 95%, or up to 100%, when compared to when compared to the subject prior to treatment. In particular embodiments, the LDL cholesterol level in the subject delivered a pharmaceutical composition disclosed herein maintains a decrease compared to the total cholesterol level prior to delivery of the pharmaceutical composition for at least two weeks, at least one month, at least two months, or three months after the final dosing.

In particular embodiments, the LDL cholesterol level is reduced by about 5 mg/dL, 10 mg/dL, 15 mg/dL, 20 mg/dL, 25 mg/dL, 30 mg/dL, 40 mg/dL, 50 mg/dL, 60 mg/dL, 70 mg/dL, 80 mg/dL, 90 mg/dL, 5-15 mg/dL, 10-20 mg/dL, 10-30 mg/dL, 15-30 mg/dL, 20-30 mg/dL, 25-35 mg/dL, 25-40 mg/dL, 25-50 mg/dL, 40-60 mg/dL, 50-70 mg/dL, 60-80 mg/dL, 70-100 mg/dL or more when compared to the LDL cholesterol level prior to delivery of a pharmaceutical composition disclosed herein to a subject. In particular embodiments, the subject has a baseline LDL cholesterol level of 100 mg/dL, 110 mg/dL, 115 mg/dL, 120 mg/dL, 125 mg/dL, 130 mg/dL, 135 mg/dL, 140 mg/dL, 145 mg/dL, 150 mg/dL, 155 mg/dL, 160 mg/dL, 165 mg/dL, 170 mg/dL, 175 mg/dL, 180 mg/dL, 185 mg/dL, 190 mg/dL, 195 mg/dL, 200 mg/dL or more. In some embodiments, the LDL cholesterol level is the serum LDL cholesterol level or the total body LDL cholesterol level.

In some embodiments, the compositions and methods described herein can be effective to reduce atherosclerotic plaque size in a subject by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% or even higher as compared to an initial size of atherosclerotic plaque prior to delivery of a pharmaceutical composition disclosed herein to a subject. The atherosclerotic plaque size can be reduced by about 19%-24%, 14%-29%, 12%-35%, 10-40%, 8%-45%, 5%-50%, 2%-60%, or 1%-70%.

2.4 Pharmaceutical Compositions

In some embodiments, the invention provides a pharmaceutical composition comprising a pharmaceutically acceptable carrier and an engineered meganuclease of the invention, or a pharmaceutically acceptable carrier and a polynucleotide comprising a nucleic acid encoding an engineered meganuclease of the invention. In other embodiments, the invention provides a pharmaceutical composition comprising a pharmaceutically acceptable carrier and a cell of the invention which can be delivered to a target tissue where the cell expresses the engineered meganuclease as disclosed herein. Pharmaceutical compositions of the invention can be useful for treating a subject having cardiovascular diseases and hypercholesterolemia, including autosomal dominant FH or reducing the expression and/or activity of PCSK9.

Such pharmaceutical compositions can be prepared in accordance with known techniques. See, e.g., Remington, *The Science And Practice of Pharmacy* ($21^{st}$ ed. 2005). In the manufacture of a pharmaceutical formulation according to the invention, meganuclease polypeptides (or DNA/RNA encoding the same) are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

In particular embodiments of the invention, the pharmaceutical composition can comprise one or more mRNAs described herein encapsulated within lipid nanoparticles, which are described elsewhere herein. In particular embodiments, lipid nanoparticles can comprise one or more polycistronic mRNAs described herein, wherein each polycistronic mRNA encodes two or more engineered meganucleases of the invention. In particular embodiments, lipid nanoparticles can comprise a polycistronic mRNA encoding two, three, or four engineered meganucleases described herein. In other particular embodiments, lipid nanoparticles can comprise two or more polycistronic mRNAs described herein, each encoding two or more engineered meganucleases of the invention.

Some lipid nanoparticles contemplated for use in the invention comprise at least one cationic lipid, at least one non-cationic lipid, and at least one conjugated lipid. In more particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology.

Cationic lipids can include, for example, one or more of the following: palmitoyl-oleoyl-nor-arginine (PONA), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N-(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propan-aminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In preferred embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain preferred embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (*ATTA*)-lipid conjugate, a cationic-polymer-lipid conjugates (CPLs), or mixtures thereof. In one preferred embodiment, the nucleic acid-lipid particles comprise either a PEG-lipid conjugate or an *ATTA*-lipid conjugate. In certain embodiments, the PEG-lipid conjugate or *ATTA*-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-w-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In some embodiments, the lipid nanoparticles have a composition which specifically enhances delivery and uptake in the liver, and specifically within hepatocytes.

In some embodiments, the pharmaceutical composition comprises a pharmaceutically acceptable carrier and a recombinant DNA construct described herein which comprises a nucleic acid sequence encoding an engineered meganuclease of the invention. In particular embodiments, such recombinant DNA constructs can be encapsulated within lipid nanoparticles, or packaged within other delivery vehicles known in the art, which are suitable for delivery to the target cells (e.g., liver cells, and particularly hepatocytes).

In certain embodiments, the pharmaceutical composition comprises a pharmaceutically acceptable carrier and a viral vector described herein which comprises a nucleic acid sequence encoding an engineered meganuclease of the invention. In particular embodiments, the viral vector can be an AAV vector which is suitable for delivery to the target cells, particularly liver cells such as hepatocytes. Such AAV vectors can have capsids, for example, of AAV8, AAV2, AAV9, or other liver-targeting capsids known in the art. In certain embodiments, the AAV capsid is an AAV8 capsid, which comprises a cassette including a 5' inverted terminal repeat, a liver-specific human thyroxine binding globulin (TBG) promoter, an intron, a coding sequence for an engineered meganuclease of the invention, a woodchuck hepatitis virus (WHP) posttranscriptional regulatory element, and a 3' inverted terminal repeat.

In certain embodiments, methods are provided of treating a cholesterol-related disorder, such as hypercholesterolemia comprising administering a therapeutically effective amount of a pharmaceutical composition disclosed herein along with another therapeutic agent. In particular embodiments, a pharmaceutical composition disclosed herein is administered alone.

Pharmaceutical compositions of the invention can be administered in combination therapy, i.e., combined with other agents. In some embodiments, pharmaceutical compositions disclosed herein are delivered prior to the administration of at least one other therapeutic agent. A pharmaceutical composition disclosed herein can be delivered concurrent with the administration of at least one other therapeutic agent or can be delivered subsequent to the administration of at least one other therapeutic agent. In certain embodiments, the combination therapy comprises a pharmaceutical composition disclosed herein, in combination with at least one anti-cholesterol agent. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin. In certain embodiments, an agent can act to inhibit or stimulate its target (e.g., receptor or enzyme activation or inhibition), and thereby promote increased expression of LDLR or decrease PCSK9 expression or serum cholesterol levels.

Therapeutic agents (apart from the pharmaceutical compositions disclosed herein), include, but are not limited to, at least one other cholesterol-lowering (serum and/or total body cholesterol) agent or an agent. In some embodiments, the agent increases the expression of LDLR, have been observed to increase serum HDL levels, lower LDL levels or lower triglyceride levels. Exemplary agents include, but are not limited to, statins (atorvastatin, cerivastatin, fluvastatin, lovastatin, mevastatin, pitavastatin, pravastatin, rosuvastatin, simvastatin), Nicotinic acid (Niacin) (NIACOR, NIASPAN (slow release niacin), SLO-NIACIN (slow release niacin)), Fibric acid (LOPID (Gemfibrozil), TRICOR (fenofibrate), Bile acid sequestrants (QUESTRAN (cholestyramine), colesevelam (WELCHOL), COLESTID (colestipol)), Cholesterol absorption inhibitors (ZETIA (ezetimibe)), combining nicotinic acid with statin (ADVICOR (LOVASTATIN and NIASPAN), combining a statin with an absorption inhibitor (VYTORIN (ZOCOR and ZETIA) and/or lipid modifying agents. In some embodiments, the pharmaceutical composition disclosed herein is combined with PPAR gamma agonists, PPAR alpha/gamma agonists, squalene synthase inhibitors, CETP inhibitors, anti-hypertensives, anti-diabetic agents (such as sulphonyl ureas, insulin, GLP-1 analogs, DDPIV inhibitors), ApoB modulators, MTP inhibitors and/or arteriosclerosis obliterans treatments. In some embodiments, the pharmaceutical composition disclosed herein is combined with an agent that increases the level of LDLR protein in a subject, such as statins, certain cytokines like oncostatin M, estrogen, and/or certain herbal ingredients such as berberine. In some embodiments, the pharmaceutical composition disclosed herein is combined with an agent that increases serum cholesterol levels in a subject (such as certain anti-psychotic agents, certain HIV protease inhibitors, dietary factors such as high fructose, sucrose, cholesterol or certain fatty acids and certain nuclear receptor agonists and antagonists for RXR, RAR, LXR, FXR). In some embodiments, the pharmaceutical composition disclosed herein is combined with an agent that increases the level of PCSK9 in a subject, such as statins and/or insulin. The combination of the two can allow for the undesirable side-effects of other agents to be mitigated by the pharmaceutical composition disclosed herein.

In certain embodiments, a pharmaceutical composition disclosed herein can be administered prior to, concurrent with, and subsequent to treatment with a cholesterol-lowering (serum and/or total cholesterol) agent. In certain embodiments, a pharmaceutical composition disclosed herein can be administered prophylactically to prevent or mitigate the onset of hypercholesterolemia, heart disease, diabetes, and/or any of the cholesterol-related disorder. In certain embodiments, a pharmaceutical composition disclosed herein can be administered for the treatment of an existing hypercholesterolemia condition. In some embodiments, the pharmaceutical composition disclosed herein delays the onset of the disorder and/or symptoms associated with cholesterol-related disorders. In some embodiments, the pharmaceutical composition disclosed herein is provided to a subject lacking any symptoms of any one of the cholesterol-related disorder.

2.5 Methods for Producing Recombinant AAV Vectors

In some embodiments, the invention provides recombinant AAV vectors for use in the methods of the invention. Recombinant AAV vectors are typically produced in mammalian cell lines such as HEK-293. Because the viral cap and rep genes are removed from the vector to prevent its self-replication to make room for the therapeutic gene(s) to be delivered (e.g., the meganuclease gene), it is necessary to provide these in trans in the packaging cell line. In addition, it is necessary to provide the "helper" (e.g., adenoviral) components necessary to support replication (Cots D, Bosch A, Chillon M (2013) *Curr. Gene Ther.* 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the site-specific meganuclease is not expressed in the packaging cells. Because the viral genomes of the invention comprise a recognition sequence for the meganuclease, any meganuclease expressed in the packaging cell line will be capable of cleaving the viral genome before it can be packaged into viral particles. This will result in reduced packaging efficiency and/or the packaging of fragmented genomes. Several approaches can be used to prevent meganuclease expression in the packaging cells, including:

1. The meganuclease can be placed under the control of a tissue-specific promoter that is not active in the packaging cells. For example, if a viral vector is developed for delivery of (an) meganuclease gene(s) to muscle tissue, a muscle-specific promoter can be used. Examples of muscle-specific promoters include C5-12 (Liu et al. (2004), *Hum Gene Ther* 15:783-92), the muscle-specific creatine kinase (MCK) promoter (Yuasa et al. (2002), *Gene Ther* 9:1576-88), or the smooth muscle 22 (SM22) promoter (Haase et al.

(2013), *BMC Biotechnol* 13:49-54). Examples of CNS (neuron)-specific promoters include the NSE, Synapsin, and MeCP2 promoters (Lentz et al. (2012), *Neurobiol Dis* 48:179-88). Examples of liver-specific promoters include albumin promoters (such as Pa1b), human a1-antitrypsin (such as Pa1AT), and hemopexin (such as Phpx) (Kramer et al. (2003), *Mol Therapy* 7:375-85). Examples of eye-specific promoters include opsin, and corneal epithelium-specific K12 promoters (Martin et al. (2002), *Methods* 28:(2): 267-75) (Tong et al. (2007), *J Gene Med* 9:956-66). These promoters, or other tissue-specific promoters known in the art, are not highly-active in HEK-293 cells and, thus, will not expected to yield significant levels of meganuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5A12 (kidney), cholesterol regulation APOM (liver), ADPRHL1 (heart), and monogenic malformation syndromes TP73L (muscle). (Jacox et al. (2010), *PLoS One* 5(8):e12274).

2. Alternatively, the vector can be packaged in cells from a different species in which the meganuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao et al. (Gao et al. (2007), *J Biotechnol* 131(2): 138-43). A meganuclease under the control of a mammalian promoter is unlikely to be expressed in these cells (Airenne et al. (2013), *Mol Ther* 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a meganuclease. Because these introns are not spliced efficiently from pre-mRNA transcripts in insect cells, insect cells will not express a functional meganuclease and will package the full-length genome. In contrast, mammalian cells to which the resulting recombinant AAV particles are delivered will properly splice the pre-mRNA and will express functional meganuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen (2012), *Mol Ther Nucleic Acids* 1(11): e57).

3. The meganuclease gene can be operably linked to an inducible promoter such that a small-molecule inducer is required for meganuclease expression. Examples of inducible promoters include the Tet-On system (Clontech; Chen et al. (2015), *BMC Biotechnol* 15(1):4)) and the RheoSwitch system (Intrexon; Sowa et al. (2011), *Spine* 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the meganuclease gene under the control of a promoter that responds to the corresponding transcription factor, the meganuclease gene having (a) binding site(s) for the transcription factor; and 2) including the gene encoding the transcription factor in the packaged viral genome The latter step is necessary because the meganuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables meganuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

4. In another preferred embodiment, recombinant AAV particles are produced in a mammalian cell line that expresses a transcription repressor that prevents expression of the meganuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the meganuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or, most preferably, it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), *Gene* 183:137-42). The use of a non-human transcription repressor ensures that transcription of the meganuclease gene will be repressed only in the packaging cells expressing the repressor and not in target cells or tissues transduced with the resulting recombinant AAV vector.

2.6 Engineered Meganuclease Variants

Embodiments of the invention encompass the engineered meganucleases described herein, and variants thereof. Further embodiments of the invention encompass a polynucleotide comprising a nucleic acid sequence encoding the meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave a recognition sequence within the PCSK9 gene, for example, the PCS 7-8 recognition sequence (SEQ ID NO: 4). Such variants may result, for example, from human manipulation. Biologically active variants of a native polypeptide of the embodiments (e.g., SEQ ID NOs: 6-14), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985), *Proc Natl Acad Sci USA* 82:488-492; Kunkel et al. (1987), *Methods in Enzymol* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 95%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative to parental position 26.

A substantial number of amino acid modifications to the DNA recognition domain of the wild-type I-CreI meganuclease have previously been identified (e.g., U.S. Pat. No. 8,021,867) which, singly or in combination, result in engineered meganucleases with specificities altered at individual bases within the DNA recognition sequence half-site, such that the resulting rationally-designed meganucleases have half-site specificities different from the wild-type enzyme. Table 2 provides potential substitutions that can be made in a engineered meganuclease monomer or subunit to enhance specificity based on the base present at each half-site position (−1 through −9) of a recognition half-site.

TABLE 2

| | | | | Favored Sense-Strand Base | | | | | | |
|---|---|---|---|---|---|---|---|---|---|---|
| Posn. | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |

TABLE 2-continued

| | Favored Sense-Strand Base | | | | | | | | | |
|---|---|---|---|---|---|---|---|---|---|---|
| Posn. | A | C | G | T | A/T | A/C | A/G | C/T | G/T | A/G/T | A/C/G/T |
| −3 | Q68<br>C24*<br>I24* | E68<br>F68<br>K24*<br>R24* | R68 | M68<br>C68<br>L68<br>F68 | | H68 | | | Y68 | K68 | |
| −4 | A26*<br>Q77 | E77<br>K26* | R77<br>E26* | | | | | S77<br>Q26* | | | S26* |
| −5 | | E42 | R42 | | | K28* | C28*<br>Q42 | | | | M66<br>K66 |
| −6 | Q40<br>C28* | E40<br>R28* | R40 | C40<br>I40<br>V40<br>C79<br>I79<br>V79<br>Q28* | A40<br>A79<br>A28*<br>H28* | | | | | | S40<br>S28* |
| −7 | N30*<br>Q38 | E38<br>K30*<br>R30* | K38<br>R38<br>E30* | I38<br>L38 | | | C38 | | | | H38<br>N38<br>Q30* |
| −8 | F33<br>Y33 | E33<br>D33 | F33<br>H33 | L33<br>V33<br>I33<br>F33<br>C33 | | R32* | R33 | | | | |
| −9 | | E32<br>K32 | R32<br>K32 | L32<br>V32<br>A32<br>C32 | | | | D32<br>I32 | | | S32<br>N32<br>H32<br>Q32<br>T32 |

Bold entries are wild-type contact residues and do not constitute "modifications" as used herein.
An asterisk indicates that the residue contacts the base on the antisense strand.

For polynucleotides, a "variant" comprises a deletion and/or addition of one or more nucleotides at one or more sites within the native polynucleotide. One NOs: 6-14 are provided as SEQ ID NOs: 15-23, respectively. Each of SEQ ID NOs: 15-23 share at least 90% sequence identity to SEQ ID NO: 15, which is the PCS7-binding region of the meganuclease PCS 7-8L.197 (SEQ ID NO: 6). PCS8-binding regions of SEQ ID NOs: 6-14 are provided as SEQ ID NOs: 24-32, respectively. Each of SEQ ID NOs: 24-32 share at least 90% sequence identity to SEQ ID NO: 24, which is the PCS8-binding region of the meganuclease PCS 7-8L.197 (SEQ ID NO: 6).

2. Cleavage of PCSK9 Recognition Sequences in a CHO Cell Reporter Assay

Figure 3:
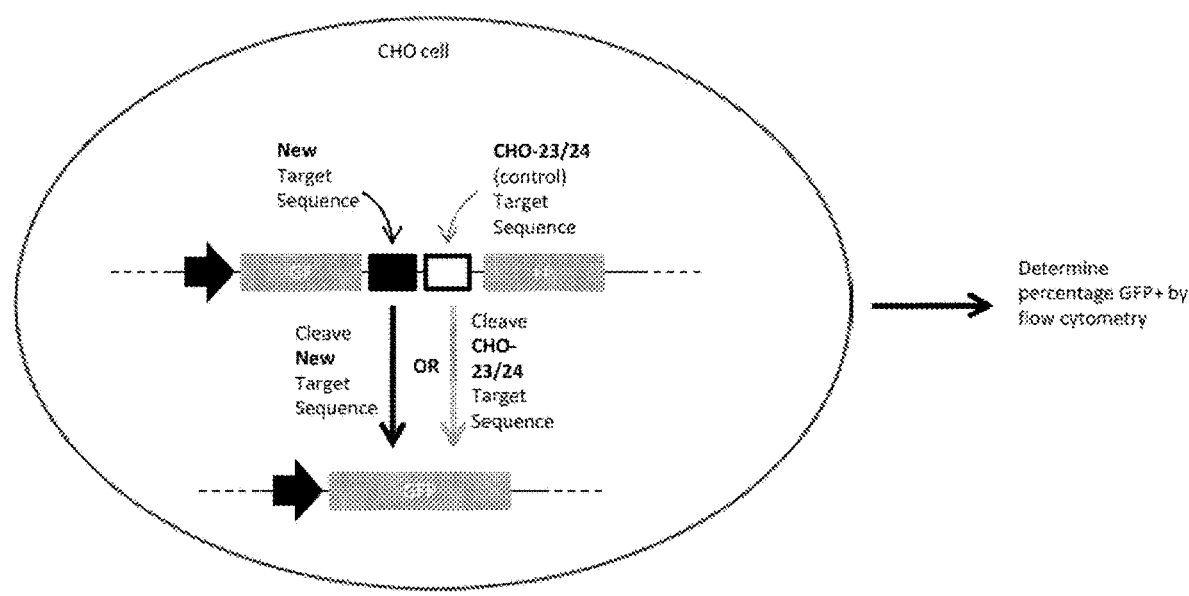
FIG. 3. Schematic of reporter assay in CHO (Chinese Hamster Ovary) cells for evaluating engineered meganucleases targeting the PCS 7-8 recognition sequence. For the engineered meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease of the invention (e.g., the PCS 7-8 recognition sequence); the recognition sequence for the CHO-23/24 meganuclease (WO 2012/167192); and the 3' 2/3 of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

To determine whether PCS 7-8 meganucleases could recognize and cleave their respective recognition sequence (SEQ ID NO: 4), each engineered meganuclease was evaluated using the CHO cell reporter assay previously described (see, WO2012/167192 and FIG. 3). To perform the assays, CHO cell reporter lines were produced which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the PCS 7-8 recognition sequence (SEQ ID NO: 4). The second recognition sequence inserted into the GFP gene was a CHO-23/24 recognition sequence, which is recognized and cleaved by a control meganuclease called "CHO-23/24". CHO reporter cells comprising the PCS 7-8 recognition sequence and the CHO-23/24 recognition sequence are referred to as "PCS 7-8 cells."

Figure 4:
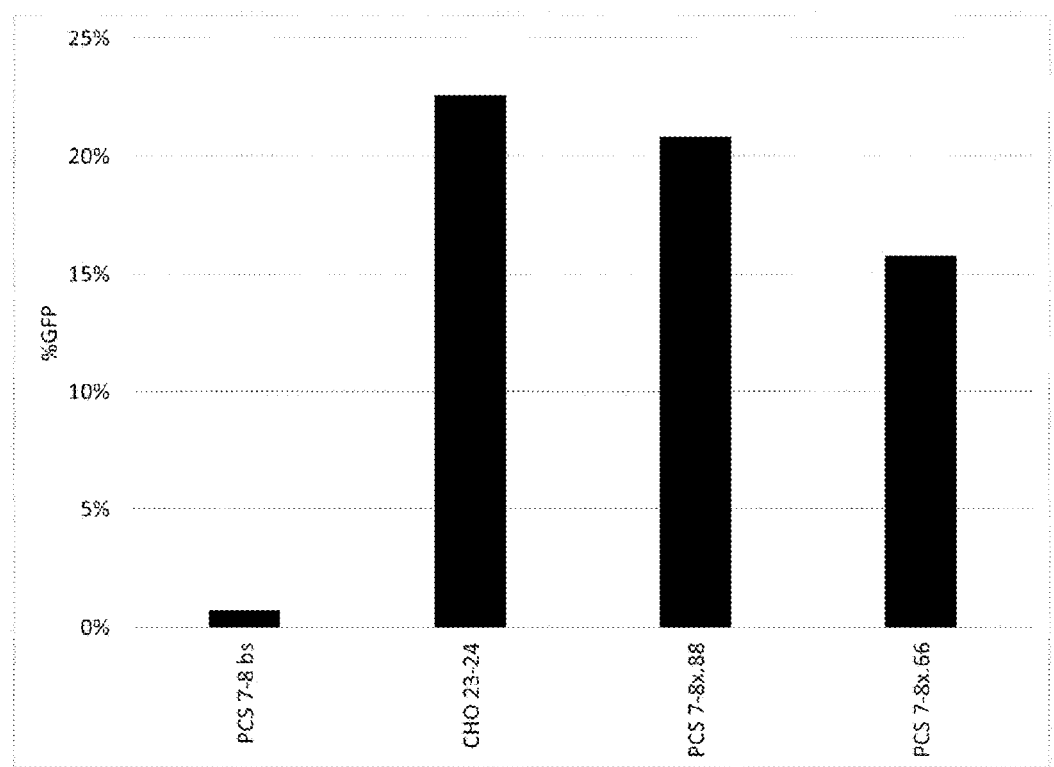
FIG. 4. Efficiency of engineered meganucleases for recognizing and cleaving recognition sequences in the PCSK9 gene in a CHO cell reporter assay. Engineered meganucleases set forth in SEQ ID NOs: 6-14 were engineered to target the PCS 7-8 recognition sequence (SEQ ID NO: 4), and were screened for efficacy in the CHO cell reporter assay. The results shown provide the percentage of GFP-expressing cells observed in each assay, which indicates the efficacy of each meganuclease for cleaving a target recognition sequence or the CHO-23/24 recognition sequence. A negative control (bs) was further included in each assay.
Figure 4:
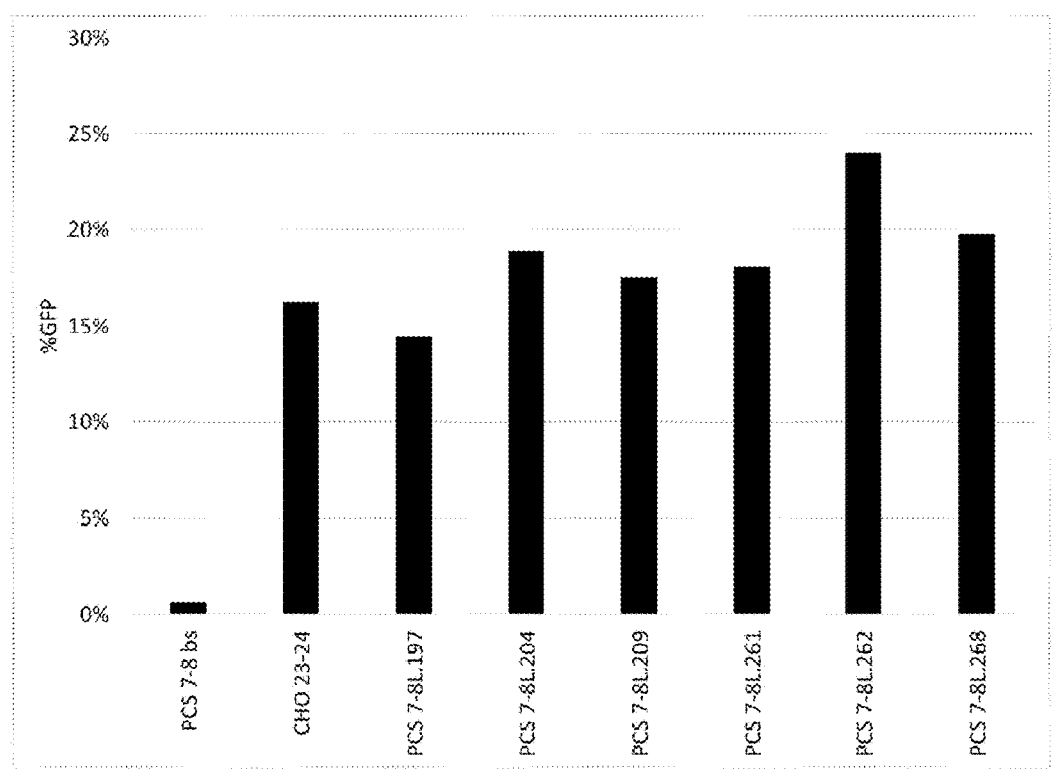
Figure 4:
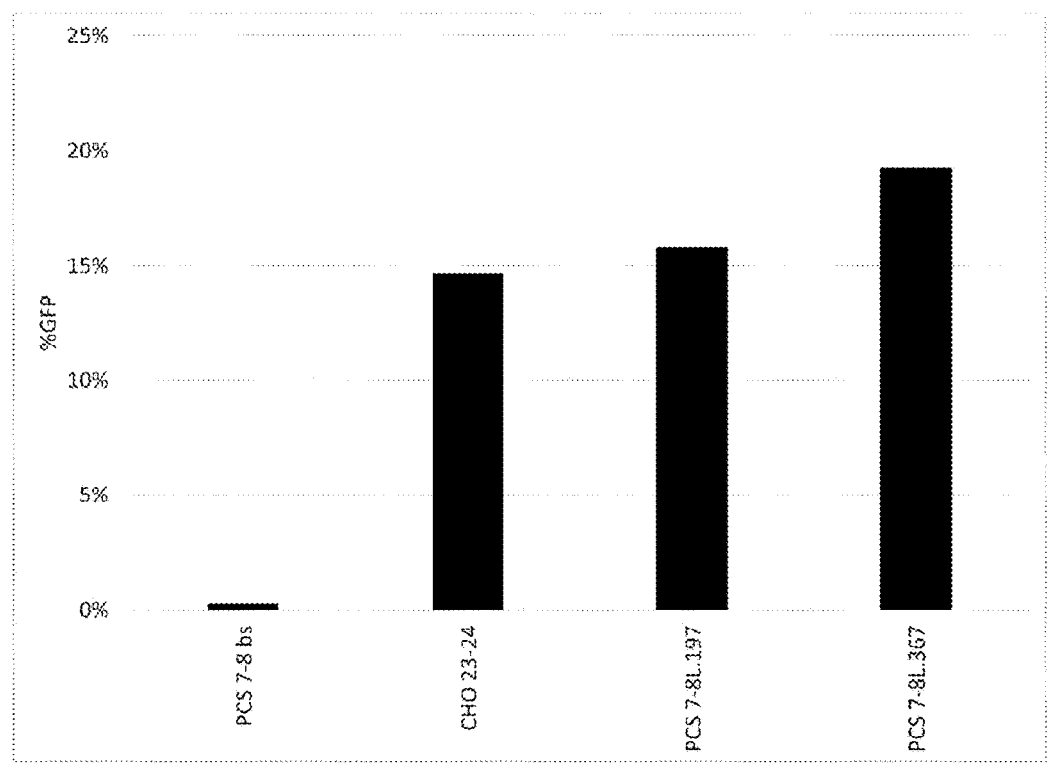

CHO reporter cells were transfected with plasmid DNA encoding their corresponding engineered meganucleases (e.g., PCS 7-8 cells were transfected with plasmid DNA encoding PCS 7-8 meganucleases) or encoding the CHO-23/34 meganuclease. In each assay, $4e^5$ CHO reporter cells were transfected with 50 ng of plasmid DNA in a 96-well plate using Lipofectamine 2000 (ThermoFisher) according to the manufacturer's instructions. At 48 hours post-transfection, cells were evaluated by flow cytometry to determine the percentage of GFP-positive cells compared to an untransfected negative control (PCS bs). As shown in FIGS. 4A-4C, all PCS 7-8 meganucleases were found to produce GFP-positive cells in cell lines comprising their corresponding recognition sequence at frequencies significantly exceeding the negative control.

The efficacy of PCS 7-8 meganucleases was also determined in a time-dependent manner after introduction of the meganucleases into CHO reporter cells. In this study, PCS 7-8 cells ($1.0 \times 10^6$) were electroporated with $1 \times 10^6$ copies of meganuclease mRNA per cell using a BioRad Gene Pulser Xcell according to the manufacturer's instructions. At the designated time points post-transfection, cells were evaluated by flow cytometry to determine the percentage of GFP-positive cells. A CHO-23/24 meganuclease was also included at each time point as a positive control.

Figure 5:
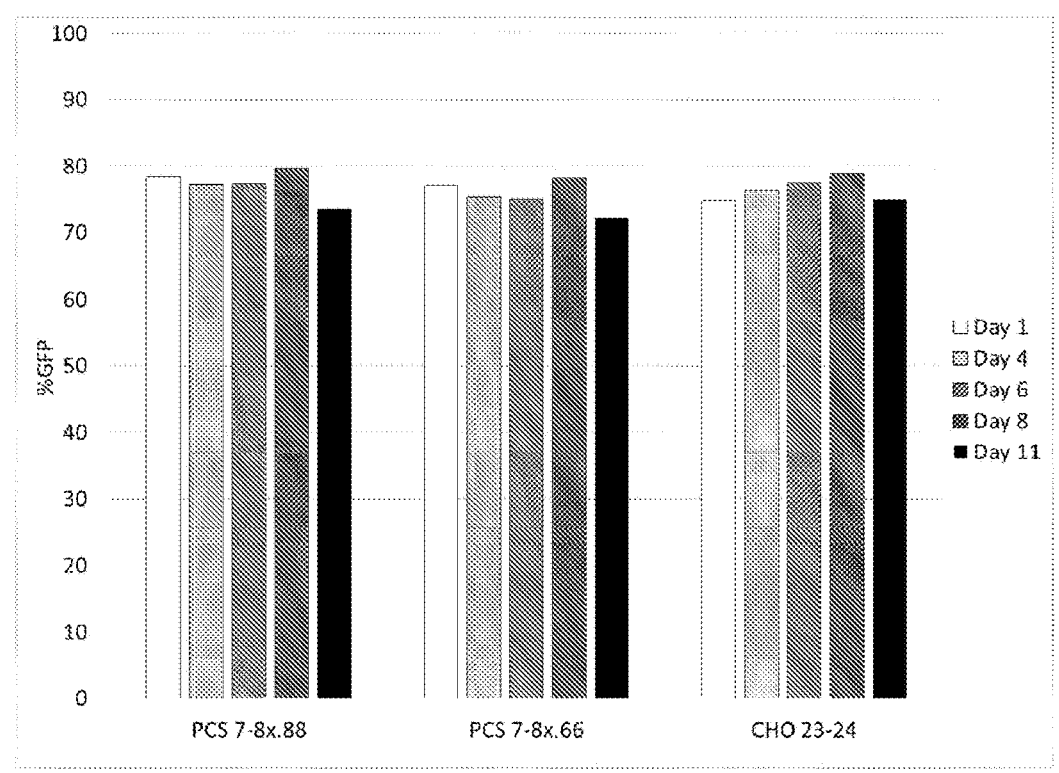
FIG. 5. Efficiency of engineered meganucleases for recognizing and cleaving recognition sequences in the human PCSK9 gene in a CHO cell reporter assay. Engineered meganucleases set forth in SEQ ID NOs: 6-14 were engineered to target the PCS 7-8 recognition sequence (SEQ ID NO: 4), and were screened for efficacy in the CHO cell reporter assay at multiple time points over 11 days after nucleofection. The results shown provide the percentage of GFP-expressing cells observed in each assay over the 11 day period of analysis, which indicates the efficacy of each meganuclease for cleaving a target recognition sequence or the CHO-23/24 recognition sequence as a function of time.
Figure 5:
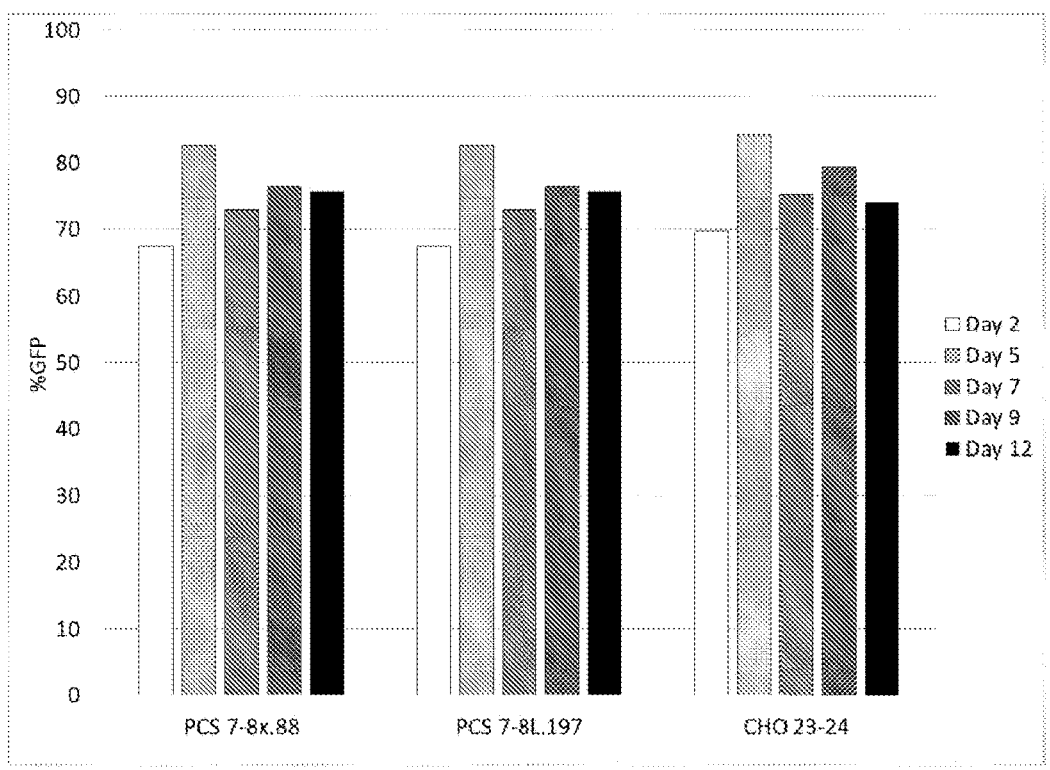
Figure 5:
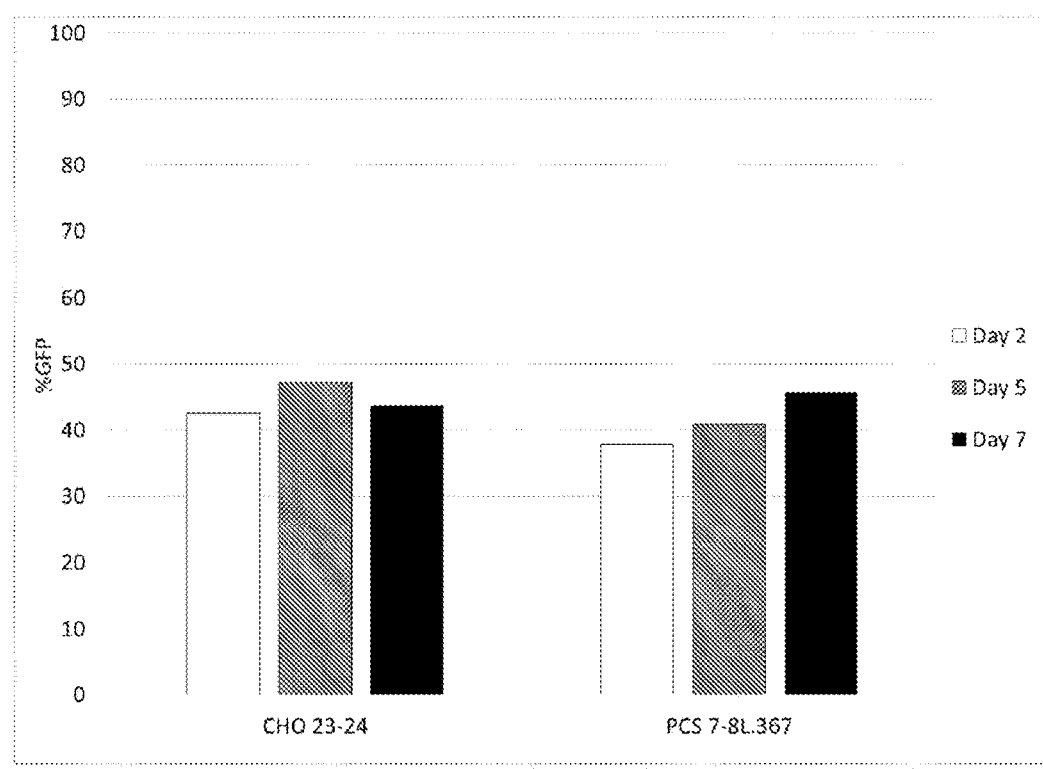

As shown in FIGS. 5A-5C, the % GFP produced by different PCS 7-8 meganucleases was consistent over the time course of the study, indicating persistent cleavage activity and a lack of any substantial toxicity in the cells.

3. Conclusions

These studies demonstrated that PCS 7-8 meganucleases encompassed by the invention can efficiently target and cleave their respective recognition sequences in cells, that this effect was consistent over time, and that the nucleases were non-toxic to the cells.

Example 2

Cleavage of PCS 7-8 Recognition Sequence in HEK293 Cells

1. Experimental Protocol and T7E Assay

This study demonstrated that PCS 7-8 meganucleases encompassed by the invention could cleave the PCS 7-8 recognition sequence in HEK293 cells.

Figure 6:
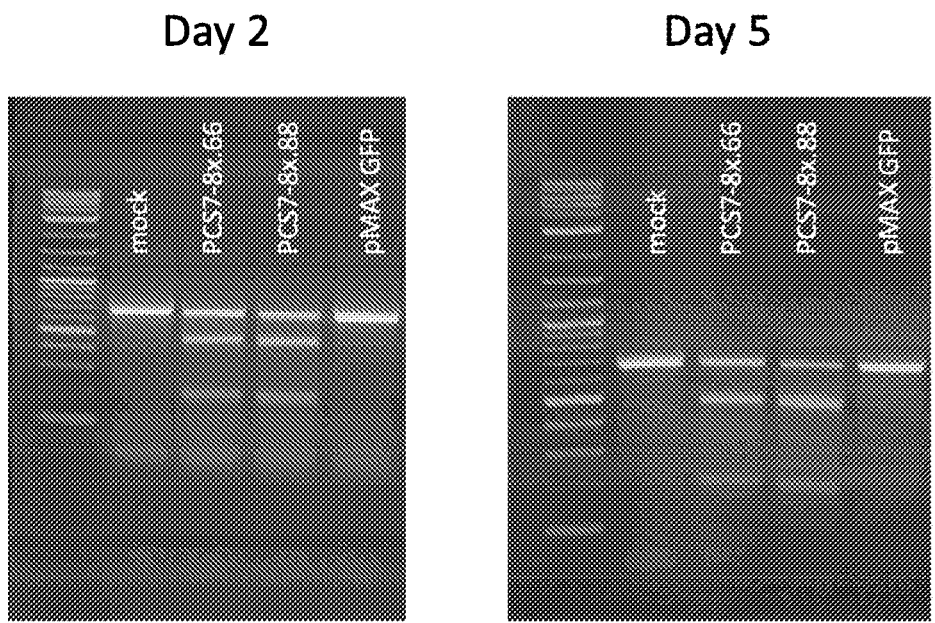
FIG. 6. T7 endonuclease I (T7E) assay. A T7E assay was performed to determine if PCS 7-8 meganucleases produced indels at their recognition site in HEK 293 cells. In the T7E assay, the PCS 7-8 locus was amplified by PCR using primers that flank the PCS 7-8 recognition sequence. If there were indels (random insertions or deletions) within the PCS 7-8 locus, the resulting PCR product would consist of a mix of wild-type alleles and mutant alleles. The PCR product was denatured and allowed to slowly reanneal. Slow reannealing allowed for the formation of heteroduplexes consisting of wild-type and mutant alleles, resulting in mismatched bases and/or bulges. The T7E1 enzyme cleaves at mismatch sites, resulting in cleavage products that can be visualized by gel electrophoresis. The PCS 7-8x.88 and PCS 7-8x.66 meganucleases were evaluated at day 2 and day 5 post-nucleofection.

$2e^6$ 293 cells were electroporated with 2.7 ugs of a given PCS meganuclease mRNA using a BioRad Gene Pulser Xcell according to the manufacturer's instructions. At 2 and 5 days post-transfection, genomic DNA (gDNA) was harvested from cells and a T7 endonuclease I (T7E) assay was performed to estimate genetic modification at the endogenous PCS 7-8 recognition sequence (FIG. 6). In the T7E assay, the PCS 7-8 locus was amplified by PCR using primers that flank the PCS 7-8 recognition sequence. If there were indels (random insertions or deletions) within the PCS 7-8 locus, the resulting PCR product would consist of a mix of wild-type alleles and mutant alleles. The PCR product was denatured and allowed to slowly reanneal. Slow reannealing allowed for the formation of heteroduplexes consisting of wild-type and mutant alleles, resulting in mismatched bases and/or bulges. The T7E1 enzyme cleaved at mismatch sites, resulting in cleavage products that can be visualized by gel electrophoresis.

2. Results

At days 2 and 5 post-transfection, lower molecular weight DNA fragments were observed in cells that received PCS 7-8x.66 and PCS 7-8x.88, while cells that were either mock transfected or transfected with mRNA encoding GFP control only displayed a full length PCR product (FIG. 6). These lower molecular weight DNA fragments are produced by T7 endonuclease I cleavage at mismatched DNA caused by the activity of the meganuclease on the PCS recognition site.

3. Conclusions

The T7 endonuclease I assay detected the presence of indels around the PCS 7-8 meganuclease recognition site in HEK293 cells treated with PCS 7-8 meganucleases, indicating cleavage of the target site and error-prone repair of the site by non-homologous end joining (NHEJ).

Example 3

Deep Sequencing to Observe Indels at PCS 7-8 Recognition Sequence

1. Deep Sequencing Protocol

In order to directly observe insertions or deletions at the intended PCS 7-8 meganuclease target site, a deep sequencing protocol was used. $2e^6$ HEK 293 cells were electroporated with 5 ug of PCS 7-8 meganuclease mRNA using a BioRad Gene Pulser Xcell according to the manufacturer's instructions. A mock electroporation was also performed with no mRNA. At 48 hours post-transfection, genomic DNA (gDNA) was harvested from cells. The PCS 7-8 locus was amplified by PCR using primers that flank the PCS 7-8 recognition sequence. This amplicon was run on an agarose gel for visual confirmation, extracted using a Macherey-Nagel Nucleospin Gel and PCR Clean-up kit, and sequencing libraries were prepared using the NEBNext Ultra II DNA Library Kit for Illumina from New England Biolabs. The paired-end sequencing libraries were read on an Illumina Miseq DNA sequencer. Sequencing data was analyzed using custom scripts. Reads with start or end points not within 25 bp of the full-length amplicon were removed. The percent of reads with indels was calculated by dividing the number of full-length reads having an indel that incorporated at least one of the middle 8 bp of the recognition sequence by the total number of full-length reads.

2. Results

As shown in Table 3, each of the PCS 7-8 meganucleases evaluated by deep sequencing showed at least a 100-fold increase in the percent indels at their intended recognition site as compared to the mock treatment.

TABLE 3

| Meganuclease | % Indels |
|---|---|
| Mock | 0.40% |
| PCS 7-8x.88 | 53.98% |
| PCS 7-8L.209 | 53.16% |
| PCS 7-8L.268 | 52.51% |
| PCS 7-8L.261 | 55.35% |
| PCS 7-8L.204 | 58.36% |
| PCS 7-8L.197 | 56.53% |
| PCS 7-8L.262 | 53.45% |

3. Conclusions

These experiments clearly demonstrate the ability of PCS 7-8 meganucleases of the invention to cleave the their intended target site (i.e., the PCS 7-8 recognition sequence) in HEK 293 cells and induce the appearance of indels via error-prone repair by non-homologous end joining.

Example 4

Gene editing of primate liver in vivo using PCS 7-8 meganucleases

1. Methods and Materials

Experiments were conducted to evaluate the ability of PCS 7-8 meganucleases to edit the PCS 7-8 recognition site in liver cells in vivo in a non-human primate model, and to determine the effect of such editing on serum levels of PCSK9 in the subjects.

The PCS 7-8x.88 meganuclease was introduced via a recombinant AAV vector. The AAV vector had an AAV8 capsid and comprised, from 5' to 3', a 5' inverted terminal repeat, a liver-specific human thyroxine binding globulin (TBG) promoter, an intron, a coding sequence for the PCS 7-8x.88 meganuclease, a woodchuck hepatitis virus (WHP) posttranscriptional regulatory element, and a 3' inverted terminal repeat. The vector is referred to as AAV8.TBG.PI.PCS7-8x.88.WPRE.bGH.

The AAV vector was prepared in a pharmaceutical composition and administered as a single infusion at day 0 to four different rhesus macaques, each weighing approximately 6.5 kg. Animal (male) RA1866 received a single dose of $3 \times 10^{13}$ GC/kg, representing the highest dose evaluated in these studies. Animal RA1857 (male) received a single dose of $6 \times 10^{12}$ genome copies (GC)/kg. Animal RA1829 (female) and animal RA2334 (male) each received a single dose of $2 \times 10^{12}$ genome copies (GC)/kg. Blood samples were collected at days −3 and 0, and at multiple time points through 168 days (low dose animals) or 280 days (high and middle dose animals) post-administration for analysis of serum PCSK9 protein levels by ELISA, analysis of total cholesterol, HDL, LDL, and triglycerides, and analysis of alanine aminotransferase (ALT) levels. Additionally, liver biopsy samples were obtained on day 17 post-administration for PCR analysis of insertions and deletions (indels) at the PCS 7-8 recognition sequence, and for analysis of PCS 7-8x.88 meganuclease expression in hepatic cells by in situ hybridization (ISH).

2. Changes in Serum PCSK9 Protein Levels

Serum PCSK9 protein levels were determined by ELISA at days −3, 0, and at multiple time points post-administration of the AAV vector. High and middle dose animals were followed for 280 days post-administration, while low dose animals were followed for 168 days.

Figure 7:
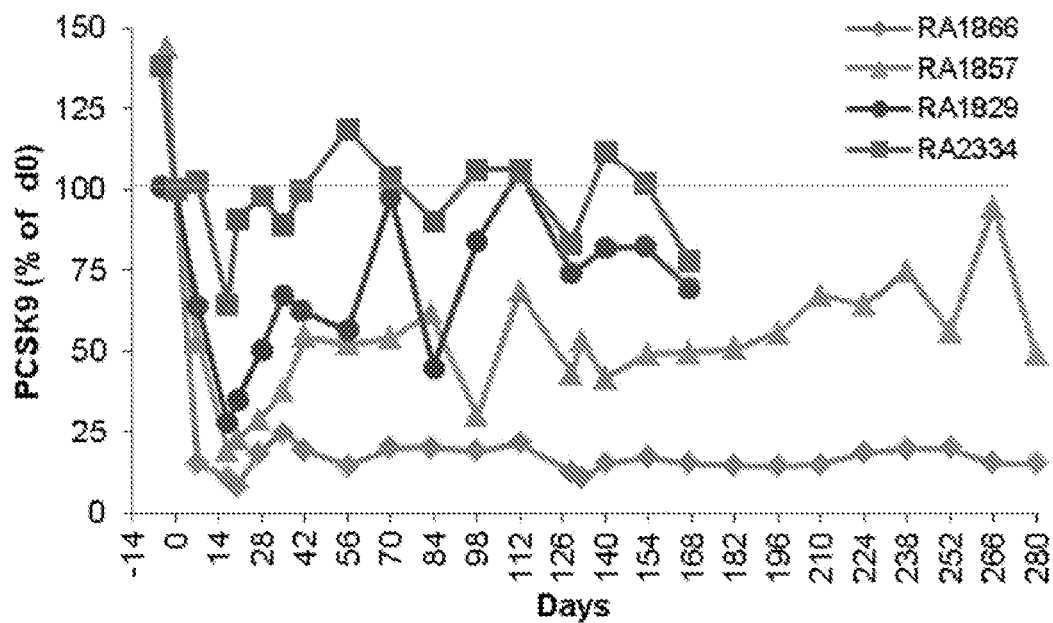
FIG. 7. Serum PCSK9 protein levels in non-human primates. An AAV vector, referred to as AAV8.TBG.PI.PCS7-8x.88.WPRE.bGH, was prepared and administered at three different doses to three male and 1 female rhesus macaques. Animal RA1866 (male) received a single dose of $3\times10^{13}$ genome copies (GC)/kg. Animal RA1857 (male) received a single dose of $6\times10^{12}$ GC/kg. Animals RA1829 (female) and RA2334 (male) each received a single dose of $2\times10^{12}$ GC/kg. Blood samples were collected at days −3, 0, and at multiple time points through day 168 (low dose animals) or day 280 (middle and high dose animals) post-administration for analysis of serum PCSK9 protein levels by ELISA.

As shown in FIG. 7, a single administration of the meganuclease AAV at day 0 induced a dramatic, dose-dependent decrease in serum PCSK9 levels in subjects RA1866, RA1857, and RA1829 by day 7, and in all groups by day 14. Subject RA1866, which received a higher dose of $3 \times 10^{13}$ GC/kg, exhibited a reduction of approximately 84% by day 7 and approximately 91% by day 20. Subject RA1857, which received a dose of $6 \times 10^{12}$ GC/kg, exhibited a reduction of approximately 46% by day 7 and approximately 77% by day 20. Subject RA1829, which received a dose of $2 \times 10^{12}$ GC/kg, exhibited a reduction of approximately 35% by day 7 and approximately 70% by day 20. Subject RA2334, which also received a dose of $2 \times 10^{12}$ GC/kg, exhibited a reduction of approximately 35% by day 14, which returned closer to baseline by day 20, where a reduction of approximately 10% was observed.

Further time points were evaluated to determine the persistence of protein inhibition throughout the course of the study. The dose-dependent reduction in serum PCSK9 levels continued to be observed through the final time points measured. In both low dose animals (RA1829 and RA2334), a reduction of approximately 25% continued to be observed on day 168. In the medium dose animal (RA1857), a reduction of approximately 50% continued to be observed at day 280. In the high dose animal (RA1866), a reduction of approximately 85% continued to be observed at day 280.

Overall, the reduction in serum PCSK9 levels throughout the course of observation appeared to be dose-dependent, with reductions persisting through the end of the study for each subject.

3. Changes in Serum Cholesterol, LDL, HDL, and Triglyceride Levels

The effect of PCS 7-8 meganuclease treatment on serum cholesterol, LDL, HDL, and triglyceride levels was also determined at days −3, 0, and at multiple time points post-administration of the AAV vector.

Figure 8:
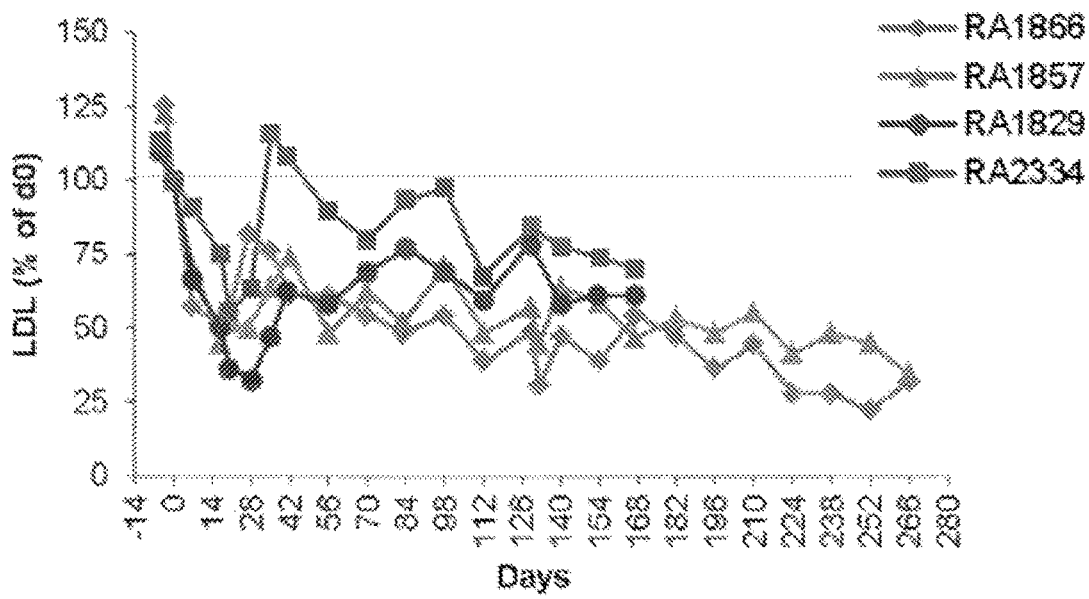
FIG. 8. Levels of total cholesterol, LDL, HDL, and triglycerides were measured at days −3, 0, and at multiple time points post-administration of the AAV encoding the PCS 7-8x.88 meganuclease.
Figure 8:
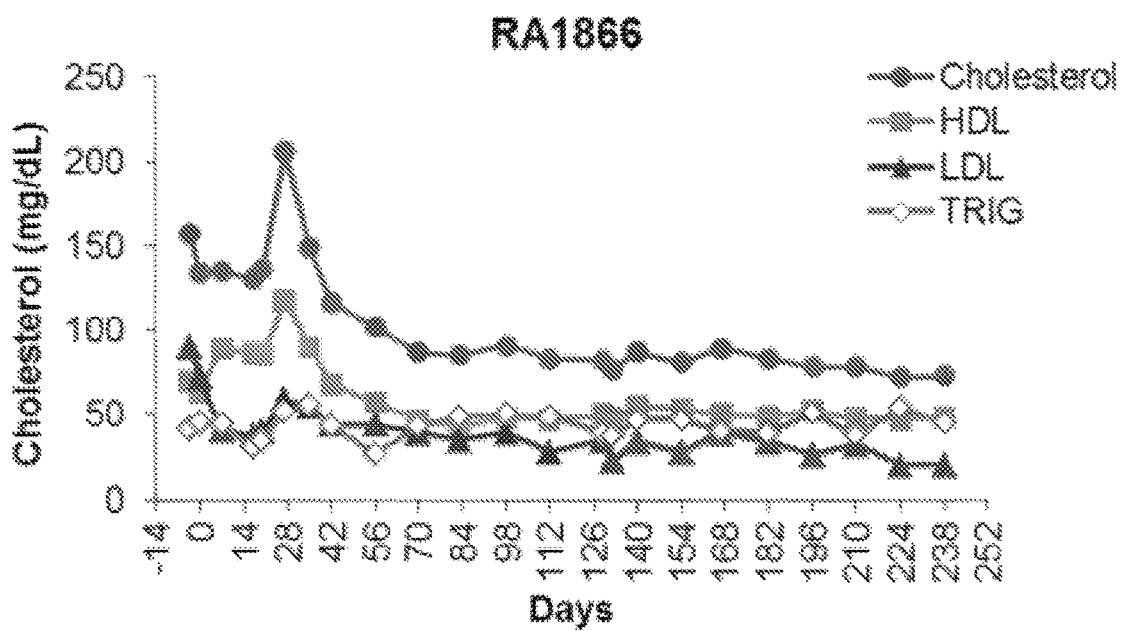
Figure 8:
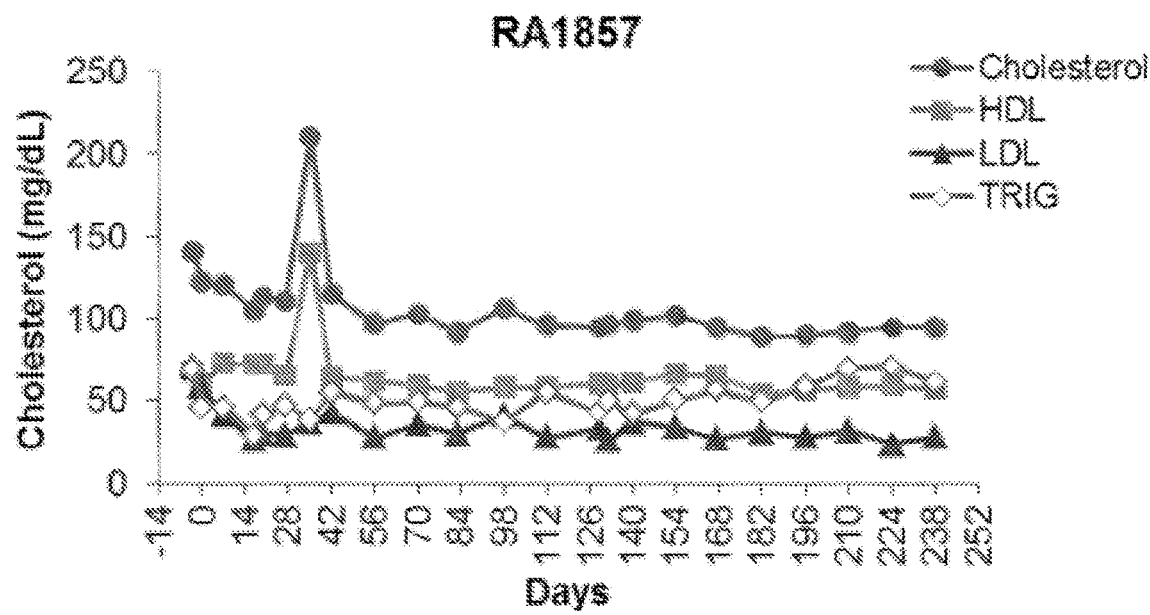
Figure 8:
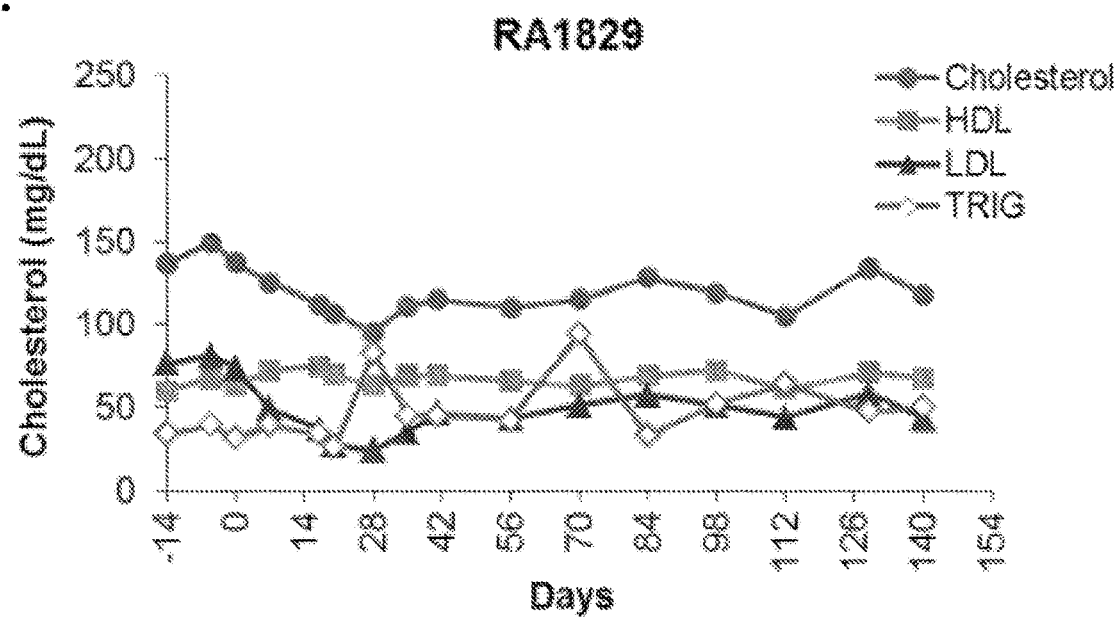
Figure 8:
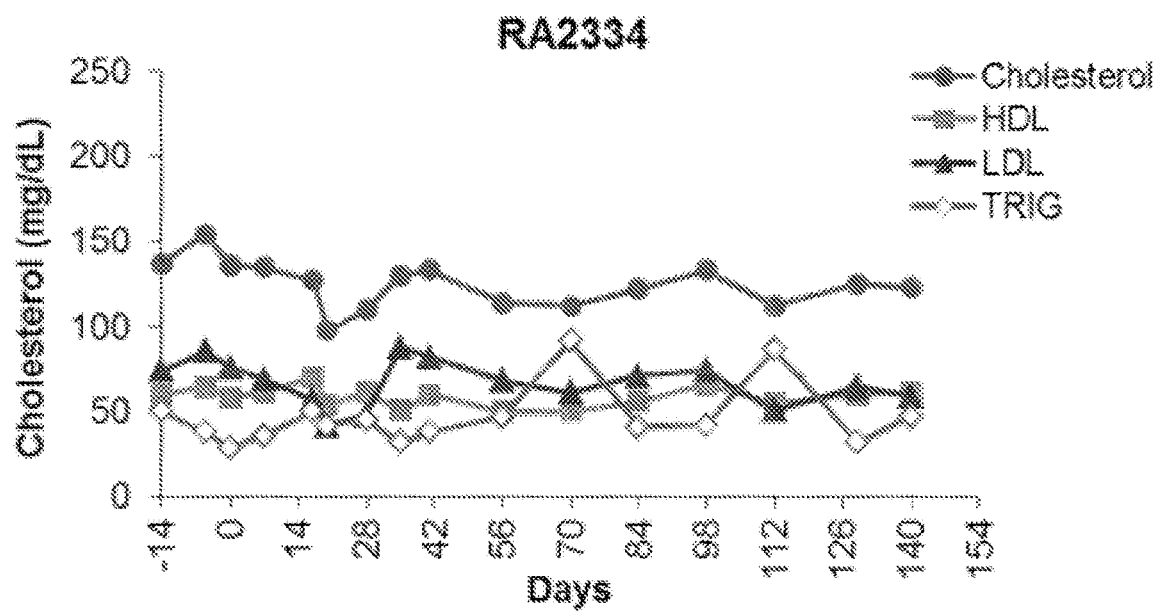

Significantly, total LDL levels were reduced in all four animals by treatment with the PCS 7-8 meganuclease (FIG. 8A). All four animals exhibited a substantial decrease in serum LDL by day 20, and reductions persisted throughout the course of the study in a dose-dependent manner. Animal RA2334 exhibited a reduction of approximately 25% through day 168, while the other low dose animal RA1829 exhibited a larger reduction of approximately 35% at the same time point. Animals RA1857 (middle dose) and RA1866 (highest dose) each exhibited a reduction of approximately 70% when measured at day 268 of the study.

Figure 9:
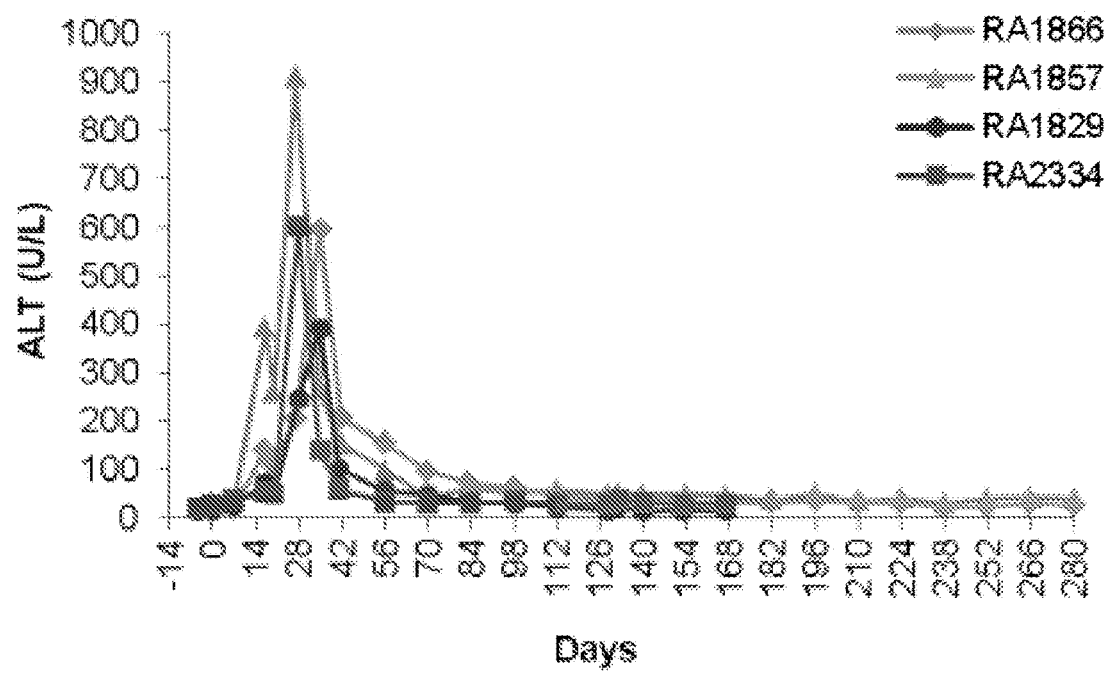
FIG. 9. Levels of alanine aminotransferase (ALT) were measured in each subject at days −3, 0, and at multiple time points post-administration of the AAV encoding the PCS 7-8x.88 meganuclease.

Notably, a transient increase in LDL levels was observed between days 28 and 42 of the study in each animal. This was consistent with changes observed in ALT levels at the same time points (FIG. 9), and may have resulted from an activation of T cells to the meganuclease or the vector capsid.

Changes in total cholesterol, HDL, LDL, and triglycerides during the course of the study are shown for each animal in FIGS. 8B-8E. As shown, total cholesterol levels are clearly reduced in the high (RA1866) and middle (RA1857) dose animals, whereas more modest effects are observed in the lower dose animals. HDL is also somewhat reduced in the high dose animal but relatively stable in the other three. Transient changes in triglyceride levels are observed during the time course of the study for each animal, but remain at approximately baseline levels at the last time point measured.

4. Meganuclease Expression and Gene Editing of Hepatic Cells In Vivo

Liver biopsies were taken at day 17 and examined for the presence of insertions or deletions (indels) at the PCS 7-8 recognition sequence. Indels were detected by the use of PCR primers flanking the recognition sequence, amplification of the intervening region of the genome, and sequencing of the resulting PCR products. A variety of indels, both insertions and deletions of different lengths, were detected at various frequencies at the PCS 7-8 recognition sequence. FIG. 10 provides the eight most frequently observed indels in subjects RA1857 and RA1866, and their respective frequencies. These eight indels comprised 73% of the indels observed in subject RA1857 and 66% of the indels observed in subject RA1866.

Figure 11:
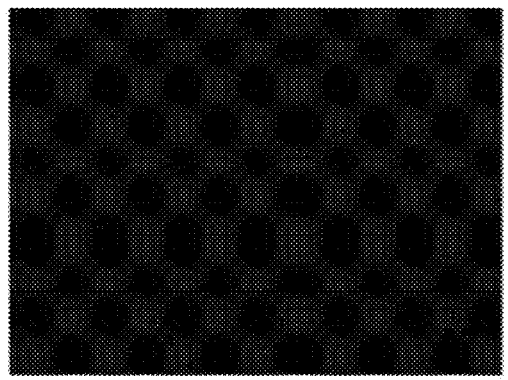
FIG. 11. In situ hybridization to detect PCS 7-8 meganuclease mRNA in hepatic cells in vivo. Liver biopsies obtained at day 17 and day 129 post-administration of the AAV8.TBG.PI.PCS7-8x.88.WPRE.bGH vector were examined by in situ hybridization (ISH). Fluorescence-labeled oligo probes were designed and bound to the PCS 7-8x.88 mRNA in biopsied hepatic cells from each subject.
Figure 11:
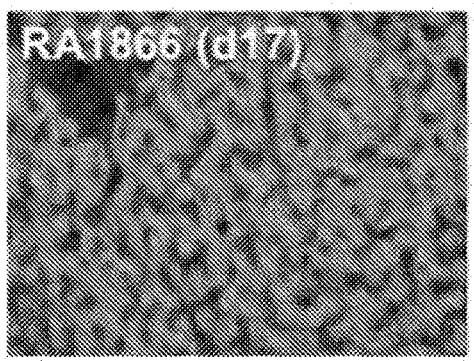
Figure 11:
Figure 11:
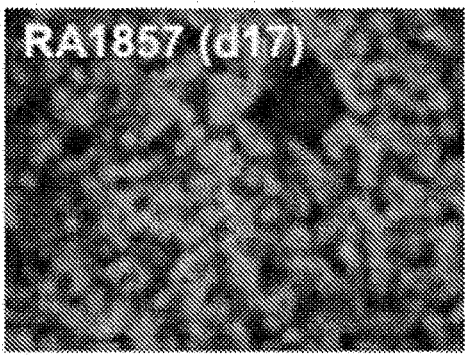
Figure 11:
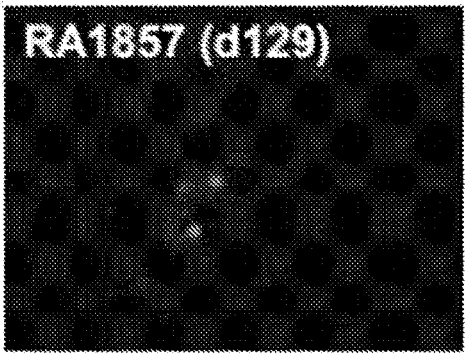
Figure 11:
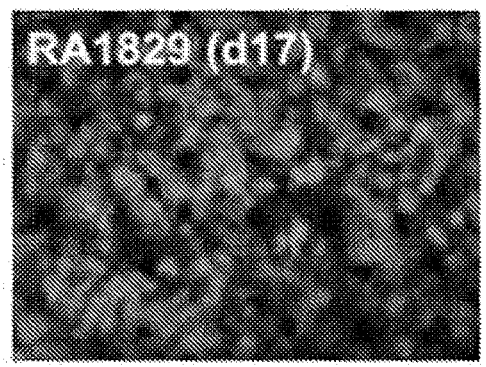
Figure 11:
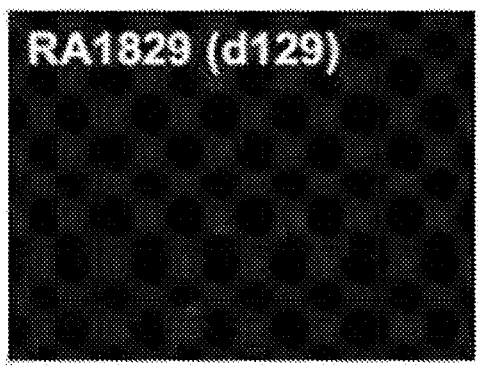
Figure 11:
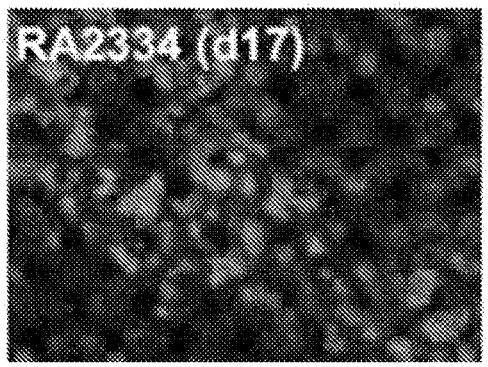
Figure 11:
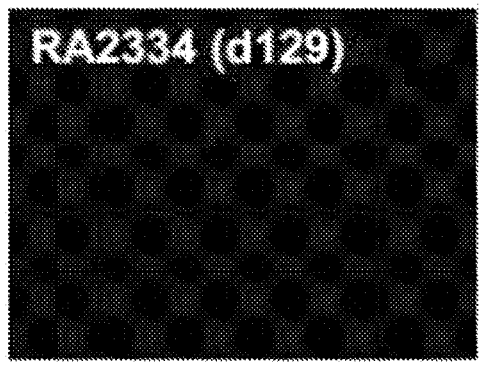

To confirm that the PCS 7-8x.88 meganuclease was indeed expressed in hepatic cells in vivo, liver biopsies obtained at day 17 and day 129 were examined by in situ hybridization (ISH). Fluorescence-labeled oligo probes were designed and bound to the PCS7-8x.88 mRNA in biopsied hepatic cells from each subject. A mock treatment of biopsied cells from another subject M11657 was performed as a control without oligo probes. As shown in FIG. 11, no fluorescence signal was observed in the mock treated cells (FIG. 11A). However, significant fluorescence was observed in hepatic cells of the treated subjects (FIG. 11B-E) at day 17. Thus, it was clear that PCS 7-8x.88 meganuclease mRNA was strongly expressed in the treated subjects during the early time points when indel formation was observed and reductions in serum PCSK9 and serum lipids were detected. FIG. 11 further shows that expression of the meganuclease mRNA was no longer observed at day 129 of the study when the second liver biopsy was obtained.

5. Treatment with PCS 7-8L.197 Meganuclease

Further studies were conducted to determine the effectiveness of the optimized, second-generation PCS 7-8L.197 meganuclease. The study protocol was similar to that previously described. The PCS 7-8L.197 meganuclease was introduced via a recombinant AAV vector. The AAV vector had an AAV8 capsid and comprised, from 5' to 3', a 5' inverted terminal repeat, a liver-specific human thyroxine binding globulin (TBG) promoter, an intron, a coding sequence for the PCS 7-8L.197 meganuclease, a woodchuck hepatitis virus (WHP) posttranscriptional regulatory element, and a 3' inverted terminal repeat. The AAV vector was prepared in a pharmaceutical composition and administered as a single infusion at day 0 to one male and one female rhesus macaque, each weighing approximately 6.5 kg, at a single dose of $6 \times 10^{12}$ genome copies (GC)/kg. Initial blood samples were collected at days 0 and 7 post-administration for analysis of serum PCSK9 protein levels by ELISA and analysis of total LDL levels.

Figure 12:
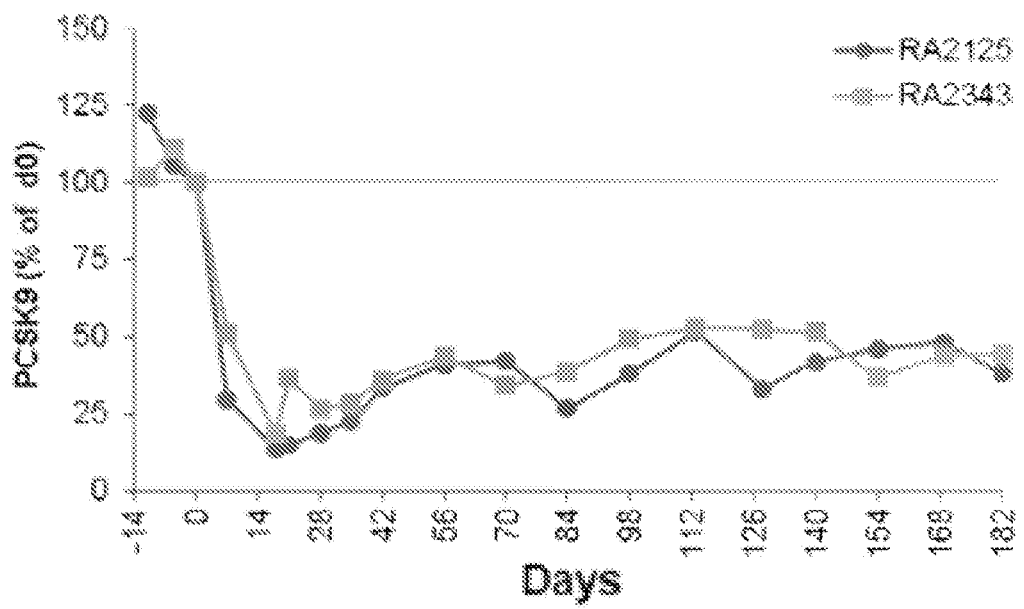
FIG. 12. Serum PCSK9 protein levels and serum LDL in non-human primates. An AAV vector, referred to as AAV8.TBG.PI.PCS7-8L.197.WPRE.bGH, was prepared and administered at a dose of $6\times10^{12}$ gene copies/kg to one male and one female rhesus macaque (subjects RA2125 and RA2343). Blood samples were collected prior to administration, and at multiple time points post-administration for analysis of serum PCSK9 protein levels by ELISA FIG. 13. Levels of total cholesterol, LDL, HDL, and triglycerides were measured prior to administration, and at multiple time points post-administration of the AAV encoding the PCS 7-8L.197 meganuclease.

As shown in FIG. 12, PCSK9 serum levels were quickly and dramatically reduced in both subjects by day 7 of the study. In subject RA2125, PCSK9 levels were reduced from approximately 180 ng/mL on day 0 to approximately 55 ng/mL on day 7 (~70% decrease). In subject RA2343, PCSK9 levels were reduced from approximately 245 ng/mL on day 0 to approximately 125 ng/mL on day 7 (~49% decrease). The reduction in PCSK9 levels persisted through day 182 post-administration of the meganuclease AAV, with each subject continuing to exhibit a decrease of approximately 60%.

Figure 13:
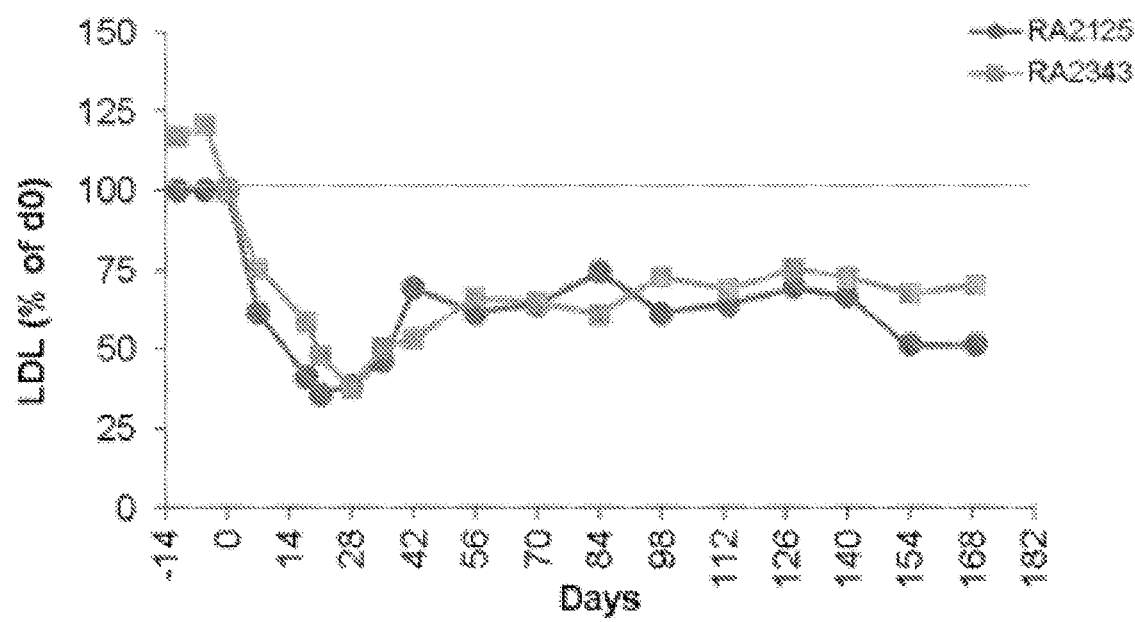
FIG. 13A shows LDL levels measured over time in each subject.
FIG. 13B shows total cholesterol, HDL, LDL, and triglyceride levels in subject RA2125.
FIG. 13C shows total cholesterol, HDL, LDL, and triglyceride levels in subject RA2343.
Figure 13:
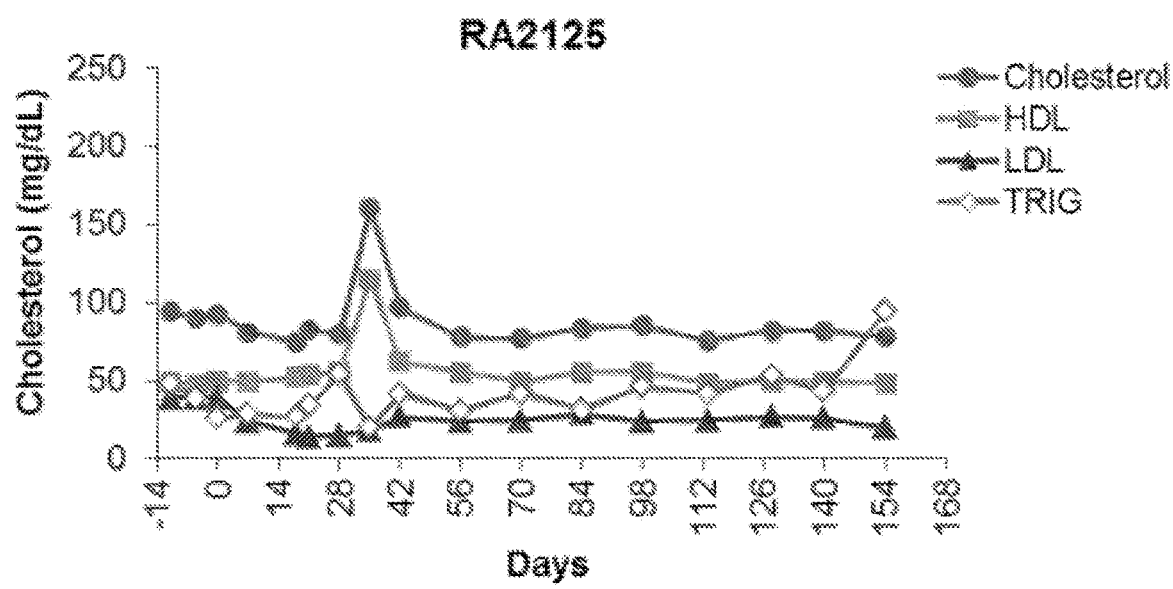
Figure 13:
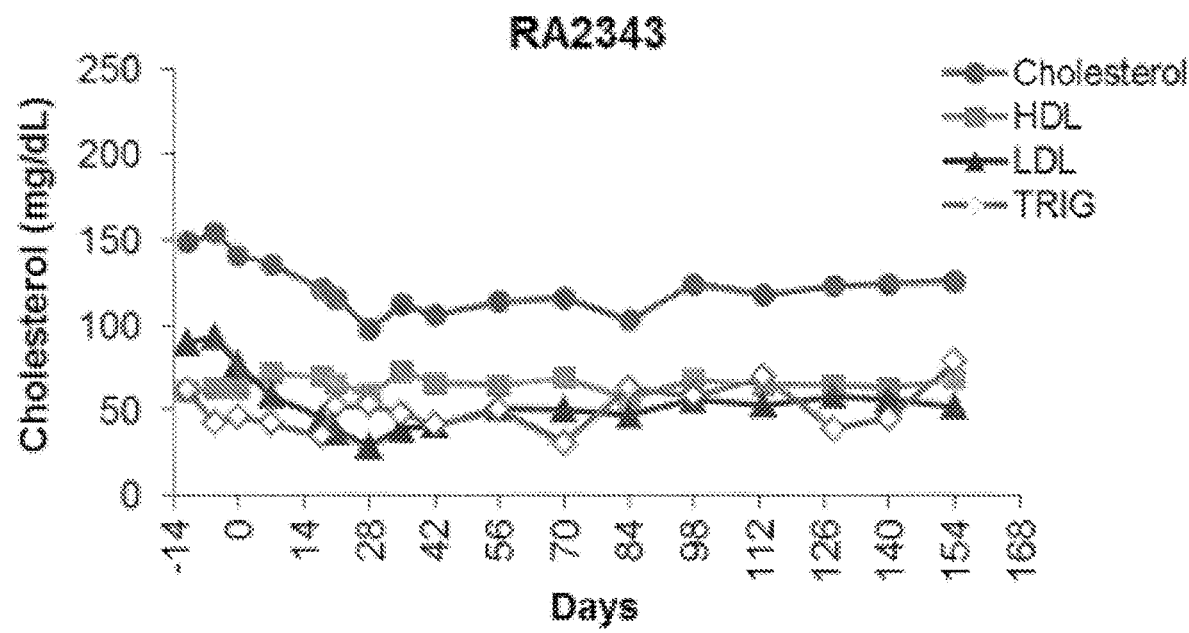

FIG. 13A shows that the reduction in serum PCSK9 levels was accompanied by substantial reductions in serum LDL levels within 7 days of treatment. In subject RA2125, serum LDL levels decreased from approximately 40 mg/dL on day 0 to approximately 25 mg/dL at day 7 (~38% decrease). In subject RA2343, serum LDL levels decreased from approximately 75 mg/dL at day 0 to approximately 55 mg/dL on day 7 (~27% decrease). Serum LDL levels continued to decrease through days 21 and 28, with reductions of approximately 65% compared to baseline. A reduction in serum LDL persisted until day 168 of the study, at which time subjects RA2125 and RA2343 exhibited largely stable reductions of approximately 35% and 50%, respectively.

Figure 14:
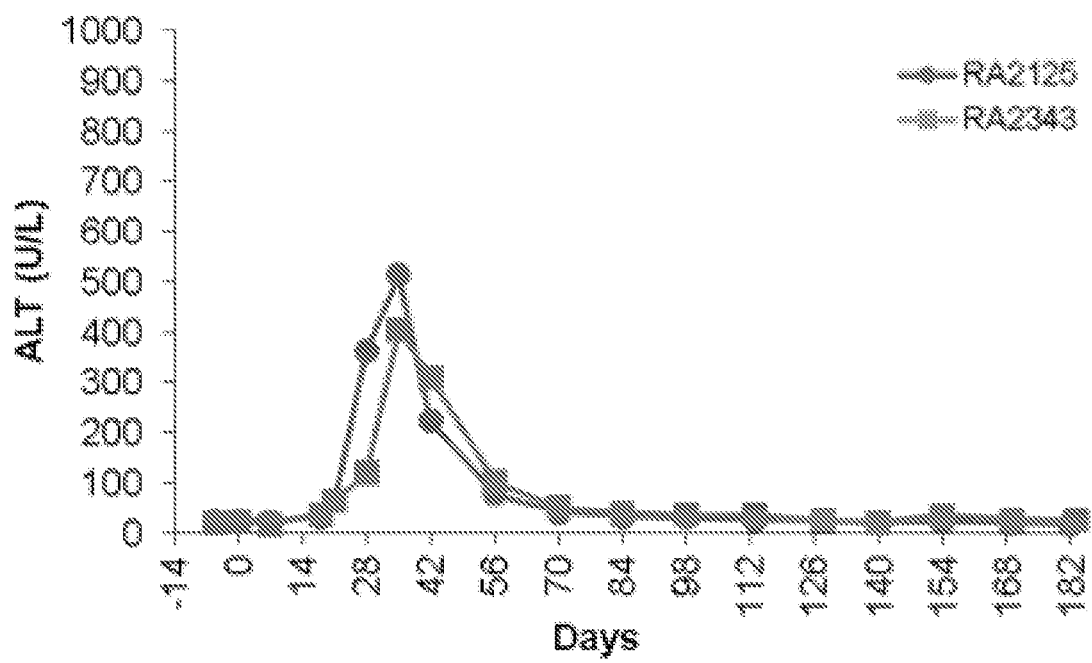
FIG. 14. Levels of alanine aminotransferase (ALT) were measured in each subject prior to administration and at multiple time points post-administration of the AAV encoding the PCS 7-8L.197 meganuclease.

Changes in total cholesterol, HDL, LDL, and triglycerides during the course of the study are shown for each animal in FIGS. 13B and 13C. As shown, total cholesterol levels are modestly reduced throughout the study in each subject, more so in subject RA2343. HDL and triglyceride levels are essentially unchanged throughout the course of the study in each subject. Similar to administration of the PCS 7-8x.88 AAV, a transient increase in serum lipids is observed in subject RA2125 between days 28 and 42, which coincides with an elevation of ALT (FIG. 14) and may result from T cell activation in response to the meganuclease or AAV capsids.

Figure 15:
FIG. 15. In situ hybridization to detect PCS 7-8 meganuclease mRNA in hepatic cells in vivo. Liver biopsies obtained at day 18 and day 128 post-administration of the AAV8.TBG.PI.PCS7-8L.197.WPRE.bGH vector were examined by in situ hybridization (ISH). Fluorescence-labeled oligo probes were designed and bound to the PCS 7-8L.197 mRNA in biopsied hepatic cells from each subject.
Figure 15:
Figure 15:
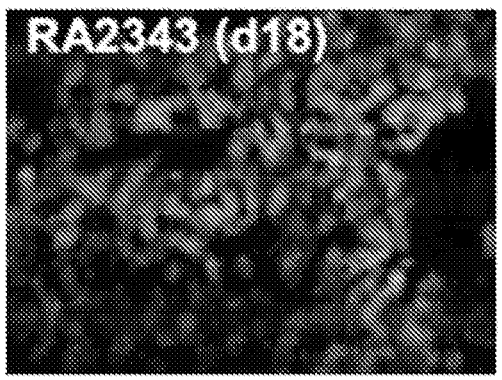
Figure 15:
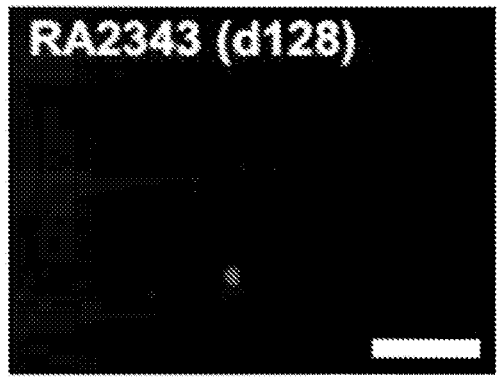

To confirm that the PCS 7-8L.197 meganuclease was expressed in hepatic cells in vivo, liver biopsies obtained at day 18 and day 129 were examined by in situ hybridization (ISH). Fluorescence-labeled oligo probes were designed and bound to the PCS 7-8L.197 mRNA in biopsied hepatic cells from each subject. As shown in FIG. 15, significant fluorescence was observed in hepatic cells of the treated subjects at day 18. Thus, it was clear that PCS7-8L.197 meganuclease mRNA was strongly expressed in the treated subjects during the early time points when reductions in serum PCSK9 and serum lipids were detected. FIG. 15 further shows that expression of the meganuclease mRNA was no longer observed at day 128 of the study when the second liver biopsy was obtained.

6. Molecular Assessment of On-Target Genome Editing

DNA isolated from liver biopsy samples was characterized for on-target editing at the designated rhPCSK9 exon 7 target site by deep sequencing of amplicons generated by anchored multiplex PCR sequencing (AMP-seq). AMP amplicons were generated using nested, locus-specific primers, in which the forward primer hybridizes to a fixed location 50 bp upstream of the targeted meganuclease cleavage site and the 3' end of the amplicon is defined by the DNA fragment length after random shearing of genomic DNA prior to amplification.

Figure 16:
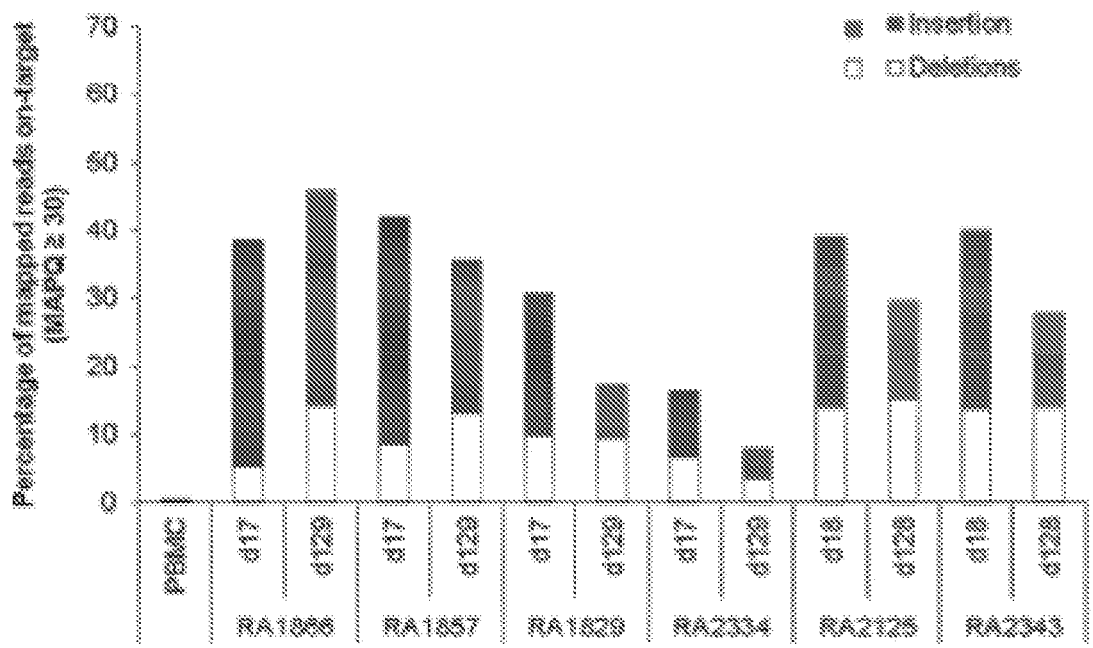
FIG. 16. Indel analysis on rhPCSK9 targeted locus in each subject by anchored multiplex PCR (AMP-seq).

In all liver samples, the frequency of short insertions and deletions observed by AMP sequencing was found to be higher than that observed in the negative control (i.e., PBMC samples from naïve animals) (FIG. 16). For the PCS 7-8x.88 meganuclease, the frequency of indels detected by AMP-seq at d129 was 46% at high dose and diminished in proportion to dose to 13% (mean, n=2) at low dose. Considering that only primary hepatocytes are selectively edited due to the use of the AAV8 serotype and the TBG promoter, AMP-seq likely underestimates the total frequency of on-target genome editing due to the presence of un-edited contaminating non-parenchymal cells present within liver biopsy samples. The overall number of editing events decreased slightly between the two time points (i.e., d17 and d129) in all animals except at high dose, where there was an increase. The total number of insertions exceeded the total number of deletions within each sample, although to varying degrees over time. The frequency of deletions were found to increase over time for both high- and mid-dose animals, and decreased over time in low-dose animals, while insertions were consistently reduced over time for each sample analyzed. Similar on-target molecular analysis of samples obtained from subjects treated with PCS 7-8L.197 AAV demonstrated a spectrum and frequency of indels like that observed with subject RA1857, which received the middle dose of AAV.

7. Conclusions

It was clear from these studies that PCS 7-8 meganucleases were successfully expressed in primate hepatic cells in vivo, as observed by ISH, and subsequently produced a cleavage site at the PCS 7-8 recognition sequence. Error-prone, non-homologous end joining at the cleavage site then resulted in numerous indels, as observed by PCR analysis and AMP-seq analysis of the site, which inhibited PCSK9 protein expression, as observed by ELISA. These studies are the first reported observation of gene editing in primate liver known to the inventors. Moreover, this is the first observation of gene editing of the PCSK9 gene in primates, which was accompanied by a substantial and persistent reduction in serum PCSK9 protein levels, serum LDL levels, and total cholesterol levels. The inventors acknowledge that the doses of AAV administered in these experiments were relatively high, and further experiments will be conducted at substantially lower doses, and with additional PCS 7-8 meganucleases, to determine both efficacy and safety profiles. Further analysis of total serum cholesterol levels, serum LDL levels, and hepatic cell LDL levels, will also be performed for pre-clinical validation of this method for lowering cholesterol.

---

The invention claimed is:

1. An engineered meganuclease that binds and cleaves a recognition sequence consisting of SEQ ID NO: 4 within a proprotein convertase subtilisin/kexin type 9 (PCSK9) gene, wherein said engineered meganuclease comprises the amino acid sequence of SEQ ID NO: 6.

2. A polynucleotide comprising a nucleic acid sequence encoding an engineered meganuclease that binds and cleaves a recognition sequence consisting of SEQ ID NO: 4 within a PCSK9 gene, wherein said engineered meganuclease comprises the amino acid sequence of SEQ ID NO: 6.

3. The polynucleotide of claim 2, wherein said polynucleotide is an mRNA.

4. A recombinant DNA construct comprising a nucleic acid sequence encoding an engineered meganuclease that binds and cleaves a recognition sequence consisting of SEQ ID NO: 4 within a PCSK9 gene, wherein said engineered meganuclease comprises the amino acid sequence of SEQ ID NO: 6.

5. A viral vector comprising a nucleic acid sequence encoding an engineered meganuclease that binds and cleaves a recognition sequence consisting of SEQ ID NO: 4 within a PCSK9 gene, wherein said engineered meganuclease comprises the amino acid sequence of SEQ ID NO: 6.

6. The viral vector of claim 5, wherein said viral vector is a recombinant AAV vector.

7. The viral vector of claim 6, wherein said recombinant AAV vector is serotype 8.

8. The viral vector of claim 6, wherein said nucleic acid sequence encoding said engineered meganuclease is operably linked to a liver-specific promoter.

* * * * *